United States Patent [19]

Yelton et al.

[11] Patent Number: 5,728,821
[45] Date of Patent: Mar. 17, 1998

[54] MUTANT BR96 ANTIBODIES REACTIVE WITH HUMAN CARCINOMAS

[75] Inventors: Dale Yelton, Seattle, Wash.; Scott Glaser, San Diego; William Huse, Del Mar, both of Calif.; Mae Joanne Rosok, Seattle, Wash.

[73] Assignee: Bristol-Myers Squibb Company, Princeton, N.J.

[21] Appl. No.: 285,936

[22] Filed: Aug. 4, 1994

[51] Int. Cl.[6] .......................... C07H 21/04; C12P 21/08
[52] U.S. Cl. ...................... 536/23.53; 435/240.2; 435/172.2; 435/70.21; 530/387.3; 530/388.8; 424/141.1; 424/155.1
[58] Field of Search ................ 536/23.53; 435/320.1, 435/240.2, 172.2, 70.21

[56] References Cited

U.S. PATENT DOCUMENTS

| | | |
|---|---|---|
| 4,474,893 | 10/1984 | Reading . |
| 4,507,391 | 3/1985 | Pukel et al. . |
| 4,579,827 | 4/1986 | Sakamoto et al. . |
| 4,612,282 | 9/1986 | Schlom et al. . |
| 4,676,980 | 6/1987 | Segal . |
| 4,708,930 | 11/1987 | Kortright et al. . |
| 4,713,351 | 12/1987 | Knauf et al. . |
| 4,713,352 | 12/1987 | Bander et al. . |
| 4,737,579 | 4/1988 | Hellström et al. . |
| 4,753,894 | 6/1988 | Frankel et al. . |
| 5,491,088 | 2/1996 | Hellstrom et al. ................. 435/344.1 |

FOREIGN PATENT DOCUMENTS

WO 89/05309 of 0000 WIPO .

OTHER PUBLICATIONS

Glaser et al., J. Immunol. 149:3903–3913, 1992.
Bajorath, Bioconjugate Chem 5(3):213–219, 1994.
McAndrew et al. J Cellular Biochem Suppl. 18(D):192, 1994.
Nisonoff et al., "The Antibody Molecule," Academic Press, New York (1975) (Exhibit 12).
Hellström et al., "Antitumor Effects of L6, an IgG2a Antibody that Reacts with Most Human Carcinomas", Proc. Natl. Acad. Sci. USA, 83:7059–7063 (1986) (Exhibit 13).
Drebin et al., "Monoclonal Antibodies Specific for the Neu Oncogene Product Directly Mediate Anti–tumor Effects in Vivo", Oncogene, 2:387–394 (1988) (Exhibit 14).
Papsidero, "Recent Progress in the Immunological Monitoring of Carcinomas Using Monoclonal Antibodies", Semin. Surg. Oncol. 1, 171–81 (1985) (Exhibit 15).
Schlom et al., "Potential Clinical Utility of Monoclonal Antibodies in the Management of Human Carcinomas", Important Adv. Oncol., pp. 170–192 (1985) (Exhibit 16).
Allum et al., "Monoclonal Antibodies in the Diagnosis and Treatment of Malignant Conditions", Surg. Ann. 18 41–64 (1986) (Exhibit 17).
Houghton et al., "Monoclonal Antibodies: Potential Applications to the Treatment of Cancer", Semin. Oncol., 13 (No. 2), pp. 165–179 (1986) (Exhibit 18).

Fink et al., "Monoclonal Antibodies as Diagnostic Reagents for the Identification and Characterization of Human Tumor Antigens", Prog. Clin. Pathol. 9, 121–33 (1984) (Exhibit 19).
Johnston, "Applications of Monoclonal Antibodies in Clinical Cytology as Exemplified by Studies with Monoclonal Antibody B72.3", Acta. Cytol. 1, 537–56 (1987) (Exhibit 20).
Young et al., "Production of Monoclonal Antibodies specific for two Distinct Steric Portions of the Glycolipid Anglio–N–Riosylceramide (Asialo $GM_2$)", J. Exp. Med. 150, 1008–19 (1979) (Exhibit 21).
Kneip et al., "Gangliotriaosylceramide (Asialo $GM_2$) A Glycosphingolipid Marker for Cell Lines Derived from Patients with Hodgkin's Disease", J. Immuniol. 131, 1591–94 (1983) (Exhibit 22).
Rosen et al., "Analysis of Human Small Cell Lung Cancer Differentiation Antigens Using a Panel of Rat Monoclonal Antibodies", Cancer Res. 44, 2052–61 (1984) (Exhibit 23).
Varki et al., "Antigens Associated with a Human Lung Adenocarcinoma Defined by Monoclonal Antibodies", Cancer Res. 44, 681–85 (1984) (Exhibit 24).
Embleton et al., "Antibody Targeting of Anti–Cancer Agents", Monoclonal Antibodies for Cancer Detection and Therapy, pp. 317–344 (1984) (Exhibit 25).
Domingo et al., "Transferrin Receptor as a Target for Antibody–Drug Conjugates", Meth. Enzymol. 112, 238–47 (1985) (Exhibit 26).
Köhler and Milstein, "Continuous Cultures of Fused Cells Secreting Antibody of Predefined Specificity", Nature 256, 495–97 (1975) (Exhibit 27).
Oi et al., "Immunoglobulin Gene Expression in Transformed Lymphoid Cells", Proc. Natl. Acad. Sci. USA, 80:825 (1983) (Exhibit 28).
Potter et al., "Enhancer–dependent Expression of Human K Immunoglobulin Genes Introduced into Mouse Pre–B Lymphocytes by Electroporation", Proc. Natl. Acad. Sci. USA, 81:7161 (Exhibit 29).
Morirson et al., "Chimeric Human Antibody Molecules: Mouse Antigen–Binding Domains with Human Constant Region Domains", Proc. Natl. Acad. Sci. USA, 81:6581 (1984) (Exhibit 30).
Sahagan et al., "A Genetically Engineered Murine/Human Antibody Retains Specificity for Human Tumor–Associated Antigen", J. Immunol., 137:1066 (1986) (Exhibit 31).

(List continued on next page.)

Primary Examiner—Lila Feisee
Assistant Examiner—Susan Ungar
Attorney, Agent, or Firm—Merchant, Gould, Smith, Edell, Welter & Schmidt

[57] ABSTRACT

The present invention provides mutant BR96 polypeptides (and nucleotide sequences encoding them) having a variable region comprising an amino acid sequence derived from the variable region of BR96.

21 Claims, 23 Drawing Sheets

OTHER PUBLICATIONS

Sun et al., "Chimeric Antibody with Human Constant Regions and Mouse Variable Regions Directed Against Carcinoma–Associated Antigen 17–1A", *Proc. Natl. Acad. Sci.*, 84:214 (1987) (Exhibit 32).

Boulianne et al., "Production of Functional Chimaeric Mouse/Human Antibody", *Nature*, 312:643 (1984) (Exhibit 33).

Sharon et al., "Expression of a $V_H C_K$ Chimeric Protein in Mouse Myeloma Cells", *Nature*, 309:364 (1984) (Exhibit 34).

Tan et al., "A Human–Mouse Chimeric Immunoglobulin Gene With a Human Variable Region is Expressed in Mouse Myeloma Cells", *J. Immunol.*, 135:3564–3567 (1985) (Exhibit 35).

Folger et al., "Patterns of Integration of DNA Microinjected into Cultured Mammalian Cells: Evidence for Homologous Recombination Between Injected Plasmid DNA Molecules", *Symp. Quant. Biol.*, 49:123–138 (1984) (Exhibit 36).

Folger et al., "Patterns of Integration of DNA Microinjected Into Cultured Mammalian Cells: Evidence for Homologous Recombination Between Injected Plasmid DNA Molecules", *Mol. Cell Biol.*, 2:1372–1387 (1982) (Exhibit 37).

Kucherlapati, "Homologous Recombination Between Plasmids in Mammalian Cells Can Be Enhanced by Treatment of Input DNA", *Proc. Natl. Acad. Sci. USA*, 81:3153–3157 (1984) (Exhibit 38).

Lin et al., "Recombination in Mouse L Cells Between DNA Introduced Into Cells and Homologous Chromosomal Sequences", *Proc. Natl. Acad. Sci. USA*, 82:1391–1395 (1985) (Exhibit 39).

de Saint Vincent et al., "Homologous Recombination in Mammalian Cells Mediates Formation of a Functional Gene From Two Overlapping Gene Fragments", *Proc. Natl. Acad. Sci. USA*, 80:2002–2006 (1983) (Exhibit 40).

Shaul et al., "Homologous Recombination Between a Defective Virus and a Chromosomal Sequence in Mammalian Cells", *Proc. Natl. Acad. Sci. USA*, 82:3781–3784 (1985) (Exhibit 41).

Thomas et al., "High Frequency Targeting of Genes to Specific Sites in the Mammalian Genome", *Cell*, 44:419–428 (1986) (Exhibit 42).

Smithies et al., "Insertion of DNA Sequences Into the Human Chromosomal B–Globin Locus by Homologous Recombination", *Nature*, 317:230–234 (1985) (Exhibit 43).

Smith et al., "Homologous Recombination Between Defective Neo Genes in Mouse 3T6 Cells", *Symp. Quant. Biol.*, 49:171–181 (1984) (Exhibit 44).

Song et al., "Accurate Modification of a Chromosomal Plasmid by Homologous Recombination in Human Cells", *Proc. Natl. Acad. Sci. USA*, 84:6820–6824 (1987) (Exhibit 45).

Rubinitz and Subramani "Extrachromosomal and Chromosomal Gene Conversion in Mammalian Cells", *Mol. Cell Biol.*, 6:1608–1614 (1986) (Exhibit 46).

Liskay, "Evidence for Intrachromosomal Gene Conversion in Cultured Mouse Cells", *Cell*, 35:157–165 (1983) (Exhibit 47).

Fell et al., "Homologous Recombination in Hybridoma Cells: Heavy Chain Chimeric Antibody Produced by Gene Targeting", *Proc. Natl. Acad. Sci. USA*, 86:8507–8511 (1989) (Exhibit 48).

Hellström et al., in "Covalently Modified Antigens and Antibodies in Diagnosis and Therapy", Quash & Rodwell, Eds., Marcel Dekkar, Inc., (Publ) (1988) (Exhibit 49).

Hellström et al., "Strong Antitumor Activities of IgG3 Antibodies to a Human Melanoma–Associated Ganglioside", *Proc. Natl. Acad. Sci. USA*, 82:1499–1502 (1985) (Exhibit 50).

Nudelman et al., "Characterization of a Human Melanoma–Associated Ganglioside Antigen Defined by a Monoclonal Antibody, 4.2", *J. Biol. Chem.*, 257:(1); 12752–56 (1982) (Exhibit 51).

Hakamori, "Tumor–Associated Carbohydrate Antigens", *Ann. Rev. Immunol.*, 2:103–26 (1984) (Exhibit 52).

Abe et al., "The Monoclonal Antibody Directed to Difucosylated Type 2 Chain (Fuc 1–2Gal 1–4 Fuc 1 –3 GlycNAc; Y Determinant", *J. Biol. Chem.*, 258:11793–97 (1983) (Exhibit 53).

Lloyd et al., "Mouse Monoclonal Antibody F–3 Recognizes the Difucosyl Type–2 Blood Group Structure", *Immunogenetics*, 17:537 (1988) (Exhibit 54).

Brown et al., "A Monoclonal Antibody Against Human Colonic Adenoma Recognizes Difucosylated Type–2–Blood–Group Chains", *Biosci. Reports*, 3:163 (1983) (Exhibit 55).

Hellström et al., "Monoclonal Mouse Antibodies Raised Against Human Lung Carcinoma", *Cancer Res.* 46, 3917–23 (1986) (Exhibit 56).

Abe et al., "Differential Expression of Difucosyl Type 2 Chain (Ley) Defined by Monoclonal Antibody AH6 in Different Locations of Colonic Epithelia, Various Histological Types of Colonic Polyps and Adenocarcinomas", *Cancer Res.*, 46:2639–2644 (1986) (Exhibit 57).

Brown et al., "Structural Characterization of Human Melanoma–Associated Antigen P97 with Monoclonal Antibodies", *J. Immunol.* 127, 539–46 (1981) (Exhibit 58).

Brown et al., "Protein Antigens of Normal and Malignant Human Cell sidentified by Immunoprecipitation with Monoclonal Antibodies", *J. Biol. Chem.* 255, 4980–83 (1980) (Exhibit 59).

Yeh et al., "Cell Surface Antigens of Human Melanoma Identified by Monoclonal Antibody", *Proc. Natl. Acad. Sci. USA* 76, 2927–31 (1979) (Exhibit 60).

Yeh et al., "A Cell Surface Antigen Which is Present in the Ganglioside Fraction and Shared by Human Melanomas", *Int. J. Cancer* 29, 269–75 (1982) (Exhibit 61).

Zola et al., "Techniques for the Production and Characterization of Monoclonal Hybridoma Antibodies" in Monoclonal Hybridoma Antibodies: Techniques and Applications, Hurrell (Ed), pp. 51–52, CRC Press (1982) (Exhibit 62).

Rousseaux et al., "Optimal Conditions for the Preparation of Proteolytic Fragments from Monoclonal IgG of Different Rat IgG Subclasses", *Meth. Enzymol.* 121, 663–69 (1986) (Exhibit 63).

Bagshawe, "Tumour Markers—Where do We Go From Here?", *Br. J. Cancer.* 48, 167–73 (1983) (Exhibit 64).

Thammana et al., "Immunoglobulin Heavy Chain Class Switch from IgM to IgG in a Hybridoma", *Eur. J. Immunol.* 13, 614 (1983) (Exhibit 65).

Spira et al., "The Identification of Monoclonal Class Switch Variants by Sub–Selection and ELISA Assay", *J. Immunol. Meth.* 74, 307–15 (1984) (Exhibit 66).

Neuberger et al., "Recombinant Antibodies Possessing Novel Efector Functions", *Nature*, 312:604–608 (1984) (Exhibit 67).

Oi et al., "Chimeric Antibodies", *Biotechniques* 4, 214–21 (1986) (Exhibit 68).

Nepom et al., "Anti-idotypic Antibodies and the Induction of Specific Tumor Immunity", *Cancer and Metastasis Rev.* 6, 489–502 (1987) (Exhibit 69).

Ciocca et al., "Immunohistochemical Techniques Using Monoclonal Antibodies", *Meth. Enzymol.* 121, 562–79 (1986) (Exhibit 70).

Kimball (ED), "*Introduction to Immunology*", (2nd Ed.), pp. 113–117 (1986) (Exhibit 71).

Uotila et al., "Two-site Sandwich Enzyme Immunoassay with Monoclonal Antibodies to Human Alpha-Fetoprotein", *J. Immunol. Meht.* 42, 11 (1981) (Exhibit 72).

Sikora et al. (Eds.), *Monoclonal Antibodies*, pp. 32–52 (1984) (Exhibit 73).

Wensel & Meares, "Bifunctional Chelating Agents for Binding Metal Ions to Proteins", *Radioimmunoimaging and Radioimmunotherapy* (1983) (Exhibit 74).

Colcher et al., "Use of Monoclonal Antibodies as Radiopharmaceuticals for the Localization of Human Carcinoma Xenografts in Athymic Mice", *Meth. Enzymol.* 121, 802–16 (1986) (Exhibit 75).

Bradwell et al., "Developments in Antibody Imaging", *Monoclonal Antibodies for Cancer Detection and Therapy*, pp. 65–85 (1985) (Exhibit 76).

Arnon et al., "Monoclonal Antibodies for Immunotargeting of Drugs in Cancer Therapy in Monoclonal Antibodies and Cancer Therapy", *Monoclonal Antibodies and Cancer Therapy*, pp. 243–256 (1985) (Exhibit 77).

Hellström et al., "Antibodies for Drug Delivery", *Controlled Drug Delivery*, pp. 623–653 (1987) (Exhibit 78).

Thorpe, "Antibody Carriers of Cytotoxic Agents in Cancer Therapy: A Review in Monoclonal Antibodies '84: Biological and Clinical Applications", *Monoclonal Antibodies '84: Biological and Clinical Applications*, pp. 475–506 (1985) (Exhibit 79).

Thorpe et al., "The Preparation and Cytotoxic Properties of Antibody-Toxin Conjugates", *Immunol. Rev.* 62, 119–58 (1982) (Exhibit 80).

Order, "Analysis, Results and Future Prospective of the Therapeutic Use of Radiolabeled Antibody in Cancer Therapy", *Monoclonal Antibodies for Cancer Detection and Therapy*, pp. 203–216 (1985) (Exhibit 81).

Senter et al., "Antitumor Effects of Antibody-Alkaline Phosphatase Conjugates in Combination with Etoposide Phosphate" *Proc. Natl. Acad. Sci. USA* 85, 4842–46 (1988) (Exhibit 82).

Senter, "Enhancement of the In Vitro and In Vivo Antitumor Activities of Phosphorylated Mitomycin C and Etoposide Derivatives by Monoclonal Antibody-Alkaline Phosphatase Conjugates", *Cancer Res.*, 49:5789–5792 (1989) (Exhibit 83).

Ramsay et al., "Bone Marrow Purging Using Monoclonal Antibodies", *J. Clin. Immunol.* 8, 81–88 (1988) (Exhibit 84).

Kohler and Milstein, "Derivation of Specific Antibody-Producing Tissue Culture and Tumor Lines by Cell Fusion", *Eur. J. Immunol.*, 6:511–19 (1976) (Exhibit 85).

Douillard et al., "Enzyme-Linked Immunosorbent Assay for Screening Monoclonal Antibody Production Using Enzyme--Labeled Second Antibody", *Meth. Enzymol.* 92, 168–72 (1983) (Exhibit 86).

Sternberger, "The Unlabeled Antibody Perioxidas-Antiperoxidase (PAP) Method", *Immunochemistry*, pp. 104–169 (1979) (Exhibit 87).

Garrigues et al., "Detection of a Human Melanoma-Associated Antigen, p97 in Histological Sections of Primary Human Melanomas", *Int. J. Cancer* 29, 511–15 (1982) (Exhibit 88).

Hellström et al., "Monoclonal Antibodies to Two Determinants of Melanoma-Antigen p97 Act Synergistically in Complement-Dependent Cytotoxicity", *J. Immunol.*, 127, 157–60 (1981) (Exhibit 89).

Brown et al., "Quantitative Analysis of Melanoma-Associated Antigen p97 in Normal and Neoplastic Tissues", *Proc. Natl. Acad. Sci. USA* 78, 539–43 (1981) (Exhibit 90).

Blakey et al., "Effect of Chemical Deglycosylation of Ricin A Chain on the In Vivo Fate and Cytotoxic Acitivty of An Immunotoxin Composed of Ricin A Chain and Anti-Thy 1.1. Antibody", *Cancer Res.*, 47, 947–52 (1987) (Exhibit 91).

Lambert et al., "Purified Immunotoxins That Are Reactive with Human Lymphoid Cells", *J. Biol. Chem.* 260, 12035–41 (1985) (Exhibit 92).

Knowles et al., "Purification of Immunotoxins Containing Ricin A-Chain and Abrin A-Chain Using Blue Sepharose C1-6B", *Anal. Biochem.* 160, 440–43 (1987) (Exhibit 93).

Krishan, "Rapid Flow Cytofluorometric Analysis of Mammalian Cell Cycle by Propidium Iodie Staining", *J. Cell, Biol.*, 66:188 (1975) (Exhibit 94).

Yeh et al., "Propidium Iodide as a Nuclear Marker in Immunofluorescence. II. Use with Cellular Identification and Viability Studies", *J. Immunol. Methods*, 43:269 (1981) (Exhibit 95).

Linsley et al., "Identification and Characterization of Cellular Receptors for Growth Regulator, Oncostatin M", *J. Biol. Chem.*, 264-4282-4289 (1974) (Exhibit 96).

Cerrotini et al., "Cell-Mediated Cytotoxicity, Allograft Rejection, and Tumor Immunity", *Adv. Immunol.* 18, 67–132 (1974) (Exhibit 97).

Hellström et al., "Lymphocyte-Dependent Antibodies to Antigen 3.1. A Cell-Surface Antigen Express by a Subgroup of Human Melanomas", *Int. J. Cancer* 27, 281–85 (1981) (Exhibit 98).

Hellström et al., "Antibody Dependent Cellular Cytotoxicity to Human Melanoma Antigens", *Monoclonal Antibodies and Cancer Therapy* 27, 149–64 (1985) (Exhibit 99).

Lamoyi, "Preparation of F(ab') Fragments from Mouse IgG of Various Subclasses", *Meth. Enzymol.*, 121:652–663 (1986) (Exhibit 100).

Hellström et al., "Epitope Mapping and Use of Anti-Idiotypic Antibodies to the L6 Monoclonal Anticarcinoma Antibody", *Cancer Res.*, 50:2449–2454 (1990) (Exhibit 101).

Coffino et al., "Cloning of Mouse Myeloma Cells and Detection of Rare Variants", *J. Cell Physiol.*, 79: (3)429–440 (1972) (Exhibit 102).

Senter, "Activation of Prodrugs by Antibody-Enzyme Conjugates: A New Approach to Cancer Therapy", *FASEB J.*, 4:188–193 (1990) (Exhibit 103).

Bara et al., "Ectopic Expression of the Y (Le$_y$) Antigen Defined by Monoclonal Antibody 12–4LE in Distal Colonic Adenocarcinomas", *Int. J. Cancer*, 41:583–689 (1988) (Exhibit 104).

Brady et al., "Therapeutic and Diagnostic Uses of Modified Monoclonal Antibodies", *I. J. Radiation Oncology Biol. Phys.*, 13(10):1535–1544 (1987) (Exhibit 105).

Drebin et al., "Down-Modulation of an Oncogene Protein Product and Reversion of the Transformed Phenotype by Monoclonal Antibodies", *Cell*, 41:695–706 (1985) (Exhibit 106).

Drebin et al., "Inhibition of tumor growth by a monoclonal antibody reactive with an oncogene-encoded tumor antigen", *Proc. Natl. Acad. Sci. USA*, 83:9129–9133 (1986) (Exhibit 107).

Goding in *Monoclonal Antibodies: Principles and Practices*, pp. 118–125, Academic Press Inc. London (1983) (Exhibit 108).

Hellström et al., "Highly Tumor–reactive, Internalizing, Mouse Monoclonal Antibodies to Le$^y$–related Cell Surface Antigens", *Cancer Research*, 50:2183–2190 (1990) (Exhibit 109).

Kannagi et al., "New Globoseries Glycosphingolipiids in Human Teratocarcinoma Reactive with the Monoclonal Antibody Directed to a Developmentally Regulated Antigen, Stage–specific Embryonic Antigen 3", *J. Biol. Chem.* 258 (14):8934–8942 (1983) (Exhibit 110).

Kim et al., "Expression of Le$^y$ and Extended Le$^y$ Blood Group–Related Antigens in Human Malignant, Premalignant and Nonmalignant Colonic Tissues", *Cancer Res.*, 46:5985–5992 (1986) (Exhibit 111).

Morrison, "Transfectomas Provide Novel Chimeric Antibodies", *Science*, 229:1202–1207 (1985) (Exhibit 112).

Drebin et al., "Monoclonal Antibodies Reactive with Distinct Domains of the neu Oncogene-Encoded p185 Molecules Exert Synergistic and Anti–Tumor Effects in vivo", *Oncogene*, 2:275–277 (1988) (Exhibit 113).

Pastan and FitzGerald, "Recombinant Toxins for Cancer Treatment", *Science*, 254:1173–1177 (1991) (Exhibit 114).

FitzGerald and Pastan, "Redirecting Pseudomonas Exotoinx", *Seminars in Cell Biology*, 2:31–37 (1991) (Exhibit 115).

Vitetta et al., "Redesigning Nature's Poisons to Create Anti–Tumor Reagents", *Science* 238:1098–1104 (1987) (Exhibit 116).

Iglewski et al., "NAD–Dependent Inhibition of Protein Synthesis by *Pseudomonas aeruginosa* Toxin", *Proc. Natl. Acad. Sci. USA*, 72:2284–2288 (1975) (Exhibit 117).

Allured et al., "Structure of Exotoxin A of *Pseudomonas neruginosa* at 3.0–Angstrom Resolution," *Proc. Natl. Acad. Sci. USA*, 83:1320–1324 (1986) (Exhibit 118).

Hwang et al., "Functional Domains of Pseudomonas Exotoxin Identified by Deletion Analysis of the Gene Expressed in *E. coli*", *Cell*, 48:129–136 (1987) (Exhibit 119).

Siegall et al., "Functional Analysis of Domains II, Ib, and III of Pseudomonas Exotoxin", *J. Biol. Chem.*, 264:14256–14261 (1989) (Exhibit 120).

Kondo et al., "Activity of Immunotoxins Constructed with Modified Pseudomonas Exotoxin A Lacking the Cell Recognition Domain", *J. Biol. Chem.*, 263:9470–9475 (1988) (Exhibit 121).

Batra et al., "Antitumor Activity in Mice of an Immunotoxin Made with Anti–Transferrin Receptor and A Recombinant Form of Pseudomonas Exotoxin", *Proc. Natl. Acad. Sci. USA*, 86:8545–8549 (1989) (Exhibit 122).

Pai et al., "Anti–Tumor Activities of Immunotoxins Made of Monoclonal Antibody B3 and Various Forms of Pseudomonas Exotoxin", *Proc. Natl. Acad. Sci. USA*, 88:3358–3362 (1992) (Exhibit 123).

Covell et al., "Pharmacokinetics of Monoclonal Immunoglobulin $G_1$, $F(ab')_2$, and Fab' in Mice", *Cancer Research*, 46:3969–3978 (1986) (Exhibit 124).

Chaudhary et al., "A Recombinant Immunotoxin Consisting of Two Antibody Variable Domains Fused to Pseudomonas Exotoxin", *Nature*, 339–394 (1989) (Exhibit 125).

Siegall et al., "Cytotoxic Activity of an Interluekin 6–Pseudomonas Exotoxin Fusion Protein on Human Myeloma Cells", *Proc. Natl. Acad. Sci. USA*, 85:9738–9742 (1988) (Exhibit 126).

Kahn et al., "Monoclonal Antiidiotypic Antibodies Related to the p97 Human Melanoma Antigen", *Cancer Res.*, 49:3157–3162 (1989) (Exhibit 127).

Kabat et al., in Sequences of Proteins of Immunological Interest, Fourth Edition, U.S. Dept. of Health and Human Services, Washington, DC (1987) (Exhibit 128).

Crowl et al., "Versatile Expression Vectors for High–Level Synthesis of Cloned Gene Products in *Escherichia coli*", *Gene*, 38:31–38 (1985) (Exhibit 129).

Studier et al., "Use of Bacteriophage T7 RNA Polymerase to Direct Selective High–Level Expression of Cloned Genes", *J. Mol. Biol.*, 189:113–130 (1986) (Exhibit 130).

Brennan et al., "Preparation of Bispecific Antibodies by Chemical Recombination of Monoclonal Immunoglobulin $G_1$ Fragments", *Science*, 229(05):81–83 (1985) (Exhibit 131).

Schreiber, et al., "An Unmodified Anticarcinoma Antibody, BR96, Localizes to and Inhibits the Outgrowth of Human Tumors in Nude Mice", *Cancer Research*, 52:3262–3266 (1992) (Exhibit 132).

Siegall, et al., "In Vitro and In Vivo Characterization of BR96 sFv–PE40", *Journal of Immunology*, 152:2377–2384 (1994) (Exhibit 133).

Friedman, et al., "BR96 sFv–PE40, a Potent Single–Chain Immunotoxin That Selectively Kills Carcinoma Cells", *Cancer Research*, 53:334–339 (1993) (Exhibit 134).

Willner, et al., "6–Maleimidocaproyl)hydrazone of Doxorubicin–A New Derivative for the Preparation of Immunoconjugates of Doxorubicin", *Bioconjugate Chem.*, 4:521–527 (1993) (Exhibit 135).

Yarnold, et al., "Chimerization of Antitumor Antibodies via Homologous Recombination Conversion Vectors", *Cancer Research*, 54:506–512 (1994) (Exhibit 136).

Friedman, et al., "Antitumor Activity of the Single–Chain Immunotoxin BR96 sFv–PE40 Against Established Breast and Lung Tumor Xenografts", *Journal of Immunology*, 150:3054–3061 (1993) (Exhibit 137).

Zhao, et al., "Determination of Immunoreactivity of Doxorubicin Antibody Immunoconjugates by a Ley Competitive RIA", *Bioconjugate Chem.*, 3:549–553 (1992) (Exhibit 138).

Abraham, et al., "The Influence of Periodate Oxidation on Monoclonal Antibody Avidity and Immunoreactivity", *Journal of Immunological Methods* 144:77–86 (1991) (Exhibit 139).

Chang, et al., "Crystallization and Preliminary X–ray Analysis of the Monoclonal Anti–tumor Antibody BR96 and its Complex with the Lewis Y Determinant", *J. Mol. Biol.* (1994) 235:372–376 (Exhibit 140).

FIG. 1A

```
           10              20              30              40
            *               *               *               *
GAA GTG AAT CTG GTG GAG TCT GGG GGA GGC TTA GTG CAG CCT GGA GGG
Glu Val Asn Leu Val Glu Ser Gly Gly Gly Leu Val Gln Pro Gly Gly>

50              60              70              80              90
  *               *               *               *               *
TCC CTG AAA GTC TCC TGT GTA ACC TCT GGA TTC ACT TTC AGT GAC TAT
Ser Leu Lys Val Ser Cys Val Thr Ser Gly Phe Thr Phe Ser Asp Tyr>

100             110             120             130             140
     *               *               *               *               *
TAC ATG TAT TGG GTT CGC CAG ACT CCA GAG AAG AGG CTG GAG TGG GTC
Tyr Met Tyr Trp Val Arg Gln Thr Pro Glu Lys Arg Leu Glu Trp Val>

150             160             170             180             190
         *               *               *               *               *
GCA TAC ATT AGT CAA GGT GGT GAT ATA ACC GAC TAT CCA GAC ACT GTA
Ala Tyr Ile Ser Gln Gly Gly Asp Ile Thr Asp Tyr Pro Asp Thr Val>

200             210             220             230             240
             *               *               *               *               *
AAG GGT CGA TTC ACC ATC TCC AGA GAC AAT GCC AAG AAC ACC CTG TAC
Lys Gly Arg Phe Thr Ile Ser Arg Asp Asn Ala Lys Asn Thr Leu Tyr>

250             260             270             280
                 *               *               *               *
CTG CAA ATG AGC CGT CTG AAG TCT GAG GAC ACA GCC ATG TAT TAC TGT
Leu Gln Met Ser Arg Leu Lys Ser Glu Asp Thr Ala Met Tyr Tyr Cys>

290             300             310             320             330
 *               *               *               *               *
GCA AGA GGC CTG GAC GAC GGG GCC TGG TTT GCT TAC TGG GGC CAA GGG
Ala Arg Gly Leu Asp Asp Gly Ala Trp Phe Ala Tyr Trp Gly Gln Gly>

340             350
     *               *
ACT CTG GTC ACG GTC TCT GTA
Thr Leu Val Thr Val Ser Val>
```

FIG. 1B

```
              10                  20                  30                  40
               *                   *                   *                   *
GAT GTT TTG ATG ACC CAA ATT CCA GTC TCC CTG CCT GTC AGT CTT GGA
Asp Val Leu Met Thr Gln Ile Pro Val Ser Leu Pro Val Ser Leu Gly>

50                  60                  70                  80                  90
       *                   *                   *                   *                   *
GAT CAA GCG TCC ATC TCT TGC AGA TCT AGT CAG ATC ATT GTA CAT AAT
Asp Gln Ala Ser Ile Ser Cys Arg Ser Ser Gln Ile Ile Val His Asn>

100                 110                 120                 130                 140
       *                   *                   *                   *                   *
AAT GGC AAC ACC TAT TTA GAA TGG TAC CTG CAG AAA CCA GGC CAG TCT
Asn Gly Asn Thr Tyr Leu Glu Trp Tyr Leu Gln Lys Pro Gly Gln Ser>

150                 160                 170                 180                 190
       *                   *                   *                   *                   *
CCA CAG CTC CTG ATC TAC AAA GTT TCC AAC CGA TTT TCT GGG GTC CCA
Pro Gln Leu Leu Ile Tyr Lys Val Ser Asn Arg Phe Ser Gly Val Pro>

200                 210                 220                 230                 240
       *                   *                   *                   *                   *
GAC AGG TTC AGC GGC AGT GGA TCA GGG ACA GAT TTC ACA CTC AAG ATC
Asp Arg Phe Ser Gly Ser Gly Ser Gly Thr Asp Phe Thr Leu Lys Ile>

250                 260                 270                 280
       *                   *                   *                   *
AGC AGA GTG GAG GCT GAG GAT CTG GGA GTT TAT TAC TGC TTT CAA GGT
Ser Arg Val Glu Ala Glu Asp Leu Gly Val Tyr Tyr Cys Phe Gln Gly>

290                 300                 310                 320                 330
       *                   *                   *                   *                   *
TCA CAT GTT CCA TTC ACG TTC GGC TCG GGG ACA AAG TTG GAA ATA AAA
Ser His Val Pro Phe Thr Phe Gly Ser Gly Thr Lys Leu Glu Ile Lys>

340
       *
CGG GCT
Arg Ala>
```

FIG. 2

```
              10              20              30              40
              *               *               *               *
GAA GTG AAT CTG GTG GAG TCT GGG GGA GGC TTA GTG CAG CCT GGA GGG
Glu Val Asn Leu Val Glu Ser Gly Gly Gly Leu Val Gln Pro Gly Gly>

50              60              70              80              90
      *               *               *               *               *
TCC CTG AAA GTC TCC TGT GTA ACC TCT GGA TTC ACT TTC AGT GAC TAT
Ser Leu Lys Val Ser Cys Val Thr Ser Gly Phe Thr Phe Ser Asp Tyr>

100             110             120             130             140
      *               *               *               *               *
TAC ATG TAT TGG GTT CGC CAG ACT CCA GAG AAG AGG CTG GAG TGG GTC
Tyr Met Tyr Trp Val Arg Gln Thr Pro Glu Lys Arg Leu Glu Trp Val>

150             160             170             180             190
      *               *               *               *               *
GCA TAC ATT AGT CAA GGT GGT GAT ATA ACC GAC TAT CCA GAC ACT GTA
Ala Tyr Ile Ser Gln Gly Gly Asp Ile Thr Asp Tyr Pro Asp Thr Val>

200             210             220             230             240
      *               *               *               *               *
AAG GGT CGA TTC ACC ATC TCC AGA GAC AAT GCC AAG AAC ACC CTG TAC
Lys Gly Arg Phe Thr Ile Ser Arg Asp Asn Ala Lys Asn Thr Leu Tyr>

250             260             270             280
              *               *               *               *
CTG CAA ATG AGC CGT CTG AAG TCT GAG GAC ACA GCC ATG TAT TAC TGT
Leu Gln Met Ser Arg Leu Lys Ser Glu Asp Thr Ala Met Tyr Tyr Cys>

290             300             310             320             330
  *               *               *               *               *
GCA AGA GGC CTG GCG GAC GGG GCC TGG TTT GCT TAC TGG GGC CAA GGG
Ala Arg Gly Leu Ala Asp Gly Ala Trp Phe Ala Tyr Trp Gly Gln Gly>

340             350
      *               *
ACT CTG GTC ACG GTC TCT GTA
Thr Leu Val Thr Val Ser Val>
```

FIG. 3

```
          10              20              30              40
           *               *               *               *
GAA GTG AAT CTG GTG GAG TCT GGG GGA GGC TTA GTG CAG CCT GGA GGG
Glu Val Asn Leu Val Glu Ser Gly Gly Gly Leu Val Gln Pro Gly Gly>

50              60              70              80              90
   *               *               *               *               *
TCC CTG AAA GTC TCC TGT GTA ACC TCT GGA TTC ACT TTC AGT GAC TAT
Ser Leu Lys Val Ser Cys Val Thr Ser Gly Phe Thr Phe Ser Asp Tyr>

100             110             120             130             140
      *               *               *               *               *
TAC ATG TAT TGG GTT CGC CAG ACT CCA GAG AAG AGG CTG GAG TGG GTC
Tyr Met Tyr Trp Val Arg Gln Thr Pro Glu Lys Arg Leu Glu Trp Val>

150             160             170             180             190
      *               *               *               *               *
GCA TAC ATT AGT CAA GAT GGT GAT ATA ACC GAC TAT CCA GAC ACT GTA
Ala Tyr Ile Ser Gln Asp Gly Asp Ile Thr Asp Tyr Pro Asp Thr Val>

200             210             220             230             240
      *               *               *               *               *
AAG GGT CGA TTC ACC ATC TCC AGA GAC AAT GCC AAG AAC ACC CTG TAC
Lys Gly Arg Phe Thr Ile Ser Arg Asp Asn Ala Lys Asn Thr Leu Tyr>

250             260             270             280
      *               *               *               *
CTG CAA ATG AGC CGT CTG AAG TCT GAG GAC ACA GCC ATG TAT TAC TGT
Leu Gln Met Ser Arg Leu Lys Ser Glu Asp Thr Ala Met Tyr Tyr Cys>

290             300             310             320             330
 *               *               *               *               *
GCA AGA GGC CTG GAC GAC GGG GCC TGG TTT GCT TAC TGG GGC CAA GGG
Ala Arg Gly Leu Asp Asp Gly Ala Trp Phe Ala Tyr Trp Gly Gln Gly>

340             350
    *               *
ACT CTG GTC ACG GTC TCT GTA
Thr Leu Val Thr Val Ser Val>
```

FIG. 4

```
              10              20              30              40
               *               *               *               *
GAA GTG AAT CTG GTG GAG TCT GGG GGA GGC TTA GTG CAG CCT GGA GGG
Glu Val Asn Leu Val Glu Ser Gly Gly Gly Leu Val Gln Pro Gly Gly>

50              60              70              80              90
       *               *               *               *               *
TCC CTG AAA GTC TCC TGT GTA ACC TCT GGA TTC CCG TTC GCG TCG TAT
Ser Leu Lys Val Ser Cys Val Thr Ser Gly Phe Pro Phe Ala Ser Tyr>

100             110             120             130             140
       *               *               *               *               *
TAC ATG TAT TGG GTT CGC CAG ACT CCA GAG AAG AGG CTG GAG TGG GTC
Tyr Met Tyr Trp Val Arg Gln Thr Pro Glu Lys Arg Leu Glu Trp Val>

150             160             170             180             190
       *               *               *               *               *
GCA TAC ATT AGT CAA GGT GGT GAT ATA ACC GAC TAT CCA GAC ACT GTA
Ala Tyr Ile Ser Gln Gly Gly Asp Ile Thr Asp Tyr Pro Asp Thr Val>

200             210             220             230             240
       *               *               *               *               *
AAG GGT CGA TTC ACC ATC TCC AGA GAC AAT GCC AAG AAC ACC CTG TAC
Lys Gly Arg Phe Thr Ile Ser Arg Asp Asn Ala Lys Asn Thr Leu Tyr>

250             260             270             280
       *               *               *               *
CTG CAA ATG AGC CGT CTG AAG TCT GAG GAC ACA GCC ATG TAT TAC TGT
Leu Gln Met Ser Arg Leu Lys Ser Glu Asp Thr Ala Met Tyr Tyr Cys>

290             300             310             320             330
 *               *               *               *               *
GCA AGA GGC CTG GCG GAC GGG GCC TGG TTT GCT TAC TGG GGC CAA GGG
Ala Arg Gly Leu Ala Asp Gly Ala Trp Phe Ala Tyr Trp Gly Gln Gly>

340             350
       *               *
ACT CTG GTC ACG GTC TCT GTA
Thr Leu Val Thr Val Ser Val>
```

FIG. 5

```
         10              20              30              40
          *               *               *               *
GAA GTG AAT CTG GTG GAG TCT GGG GGA GGC TTA GTG CAG CCT GGA GGG
Glu Val Asn Leu Val Glu Ser Gly Gly Gly Leu Val Gln Pro Gly Gly>

50              60              70              80              90
    *               *               *               *               *
TCC CTG AAA GTC TCC TGT GTA ACC TCT GGA TTC ACT TTC AGT GAC TAT
Ser Leu Lys Val Ser Cys Val Thr Ser Gly Phe Thr Phe Ser Asp Tyr>

100             110             120             130             140
      *               *               *               *               *
TAC ATG TAT TGG GTT CGC CAG ACT CCA GAG AAG AGG CTG GAG TGG GTC
Tyr Met Tyr Trp Val Arg Gln Thr Pro Glu Lys Arg Leu Glu Trp Val>

150             160             170             180             190
      *               *               *               *               *
GCA TAC ATT AGT CAA GAT GGT GAT ATA ACC GAC TAT CCA GAC ACT GTA
Ala Tyr Ile Ser Gln Asp Gly Asp Ile Thr Asp Tyr Pro Asp Thr Val>

200             210             220             230             240
      *               *               *               *               *
AAG GGT CGA TTC ACC ATC TCC AGA GAC AAT GCC AAG AAC ACC CTG TAC
Lys Gly Arg Phe Thr Ile Ser Arg Asp Asn Ala Lys Asn Thr Leu Tyr>

250             260             270             280
          *               *               *               *
CTG CAA ATG AGC CGT CTG AAG TCT GAG GAC ACA GCC ATG TAT TAC TGT
Leu Gln Met Ser Arg Leu Lys Ser Glu Asp Thr Ala Met Tyr Tyr Cys>

290             300             310             320             330
 *               *               *               *               *
GCA AGA GGC CTG GCG GAC GGG GCC TGG TTT GCT TAC TGG GGC CAA GGG
Ala Arg Gly Leu Ala Asp Gly Ala Trp Phe Ala Tyr Trp Gly Gln Gly>

340             350
    *               *
ACT CTG GTC ACG GTC TCT GTA
Thr Leu Val Thr Val Ser Val>
```

MUTANT BR96 ANTIBODIES REACTIVE WITH HUMAN CARCINOMAS

Throughout this application various publications are referenced. The disclosures of these publications in their entireties are used in this application in order to more fully describe the state of the art to which this invention pertains.

TECHNICAL FIELD OF THE INVENTION

The present invention relates to mutant BR96 antibodies and functional equivalents thereof which exhibit higher and improved affinity to its target, i.e., a BR96 antigen, than BR96. Mutant BR96 differs from BR96 in its nucleotide sequence and/or amino acid sequence in the complementarity determining regions (CDRs) of the molecule at one or more positions.

BACKGROUND OF THE INVENTION

Monoclonal antibodies and derivatives thereof have revolutionized immunology. Conventional antibodies, produced by immunization of an antibody-forming animal with an antigen, are a mixture of different antibodies, each with slightly different properties. However, monoclonal antibodies are uniform within themselves and have identical properties relative to each other including identical binding specificity.

The challenge and the goal of many scientists has been to manipulate either the antibody protein or the gene from which it is encoded so as to produce molecules with desired properties such as having increased affinity or specificity for cancer or other diseased cells that would be useful either in screening for cancer or other diseases or in their treatment. Although much progress has been made there is still more work that needs to be done in the development of monoclonal antibodies and derivatives thereof to achieve this goal.

The BR96 antibody is a monoclonal antibody that was established by using human breast carcinoma cells as an immunogen (Hellström et al., "Highly Tumor-Reactive Internalizing Mouse Monoclonal Antibodies to Le$^Y$-related Cell Surface Antigen" Cancer Res. 50:2183–2190 (1990)). BR96 exhibits high tumor selectivity.

A hybridoma which produced the murine BR96 antibody, was deposited on Feb. 22, 1989 with the American Type Culture Collection (ATCC), 12301 Parklawn Drive, Rockville, Md. 20852 and was identified as a BR96 hybridoma (ATCC Accession No.: HB 10036). A BR96 hybridoma which produced the human Gamma 1 kappa chimeric form of BR96, i.e., ChiBR96, was deposited on May 23, 1990, with the ATCC, 12301 Parklawn Drive, Rockville, Md. 20852 and was identified as a ChiBR96 hybridoma (ATCC Accession No.: HB 10460).

BR96 recognizes a carbohydrate antigen related to the Lewis Y (Le$^Y$) antigen which is abundantly expressed on carcinomas of the colon, breast, ovary, lung and pancreas and other carcinomas and, to a lesser extent, on some differentiated epithelial cells.

Because of its broad recognition of human carcinomas and a favorable ratio of tumor cell binding over a few normal tissues (i.e., gut epithelium and the pancreas), BR96 has been developed as a therapeutic antibody for cancer. BR96 is internalized after binding to tumor cells in vitro whereupon much of it is degraded in lysosomes (Garrigues, J., Garrigues, U., Hellström, I., and Hellström, K. E. Le$^Y$ specific antibody with potent anti-tumor activity is internalized and degraded in lysosomes. Am. J. Pathol., 142:607–621, 1993).

Preclinical studies of BR96 conjugated to doxorubicin through a hydrazone linkage labile to acidic pH have shown dramatic therapeutic effects in models of nude mice implanted with human tumor xenografts (Trail, P. A., Willner, D., Lasch, S. J., Henderson, A. J., Casazza, A. M., Firestone, R. A., Hellström, I., and Hellström, K. E. Cure of xenografted human carcinomas by BR96-doxorubicin immunoconjugates. Science, 261:212–215, 1993). The BR96-doxorubicin conjugate is in phase 1 clinical trials for therapy of malignancies of the breast, lung, colon, pancreas, ovary, and other carcinomas.

BR96 mediates antibody-dependent cellular cytotoxicity (ADCC), complement-dependent cytotoxicity (CDC), and is internalized. Surprisingly, BR96, in the absence of effector cells or complement, inhibits tumor cell DNA synthesis (G. J. Schreiber et al., "An Unmodified Anticarcinoma Antibody, BR96, Localizes To and Inhibits Outgrowths of Human Tumors in Nude Mice", Cancer Research 52:3262–3266 (1992)).

BR96 is apparently cytotoxic by altering membrane permeability (Garrigues et al., "Le$^Y$ Specific Antibody With Potent Anti-Tumor Activities Internalized and Degraded in Lysosomes" American Journal of Pathology 142(2):607–622 (February 1993)). Sensitivity to BR96 is related to the level of antigen expression on the cell surface (Garrigues et al. (February 1993)). A higher level of antigen expression increases the sensitivity to BR96.

The in vivo antitumor effects of BR96 were compared with those of its F(ab')$_2$ fragments, a mouse-human chimeric form, and an IgG1 class switched variant of the original BR96 (G. J. Schreiber et al., (1992)). The chimeric form of BR96 gave the strongest antitumor effects, followed by murine IgG3, while limited effects were seen with the IgG1 and with F(ab')$_2$ of BR96 (G. J. Schreiber et al., (1992)).

BR96 in several functional forms exhibited significant antitumor effects when tested in the unmodified form in nude mice xenografted into human lung adenocarcinoma.

Other monoclonal antibodies recognizing Lewis Y antigens have been described (Brown, A., Feizi, T., Gooi, H. C., Embleton, M. J., Picard, J. K. and Baldwin, R. W. A monoclonal antibody against human colonic adenoma recognizes difucosylated type-2-blood-group chains. Biosci. Rep., 3:163–170, 1983; Lloyd, K. O., Larson, G., Stromberg, N., Thurin, J., and Karlsson, K. A. Mouse monoclonal antibody F-3 recognizes the difucosyl type-2-blood group structure. Immunogenetics, 17:537–541, 1983; Kim, Y. S., Yuan, M., Izkowitz, S. H., Sun, Q., Kaizu, T., Palekar, A., Trump, B. F., and Hakomori, S. Expression of Le$^Y$ blood-group-related antigens in human malignant, premalignant, and nonmalignant colonic tissue. Cancer Res., 46:5985–5992, 1986; Hellström, I., Morn, D., Linsley, P., Brown, J. P., Brankoran, V., and Hellström, K. E. Monoclonal mouse antibodies raised against human lung carcinoma. Cancer Res. 46:3917–3923, 1986; Ernst, C. S., Shen, T-W., Litwin, S., Herlyn, M., Koprowski, H., and Sears, H. F. Multiparameter evaluation of the expression in situ of normal and tumor-associated antigens in human colorectal carcinoma. J. Natl. Cancer Inst., 77:387–395, 1986; Abe, K., Hakomori, S., and Ohshiba, S. Differential expression of difucosyl type 2 chain (le$^Y$) defined by monoclonal antibody AH6 in different locations of colonic epithelia, various histological types of colonic polyps, and adenocarcinomas. Cancer Res., 46:2639–2644, 1986; Brown, A., Ellis, I. O., Embleton, M. J., Baldwin, R. W., Turner, D. R. and Hardcastle, J. D. Immunohistochemical localization of Y hapten and the structurally related H type-2 blood-group antigens on large-bowel tumors and normal adult tissues. Int. J. Cancer, 33:727–736, 1984; Abe, K., McKibbin, J. M., and Hakomori, S. The monoclonal antibody directed to difucosylated type 2 chain (Fucα1→2Galβ1→4 (Fucα1→3)GlcNAc; Y determinant). J. Biol. Chem., 258:11793–11797, 1983; Blaineau, C., LePendu, J., Arnaud, D., Connan, F., and Avner, P. The glycosidic antigen recognized by a novel monoclonal antibody, 75.12, is developmentally regulated on mouse embryonal carcinoma cells. EMBO J., 2:2217–2222, 1983; Pour, P. M., Tempero, V. E., Cordon-Cardo, C., and Bosl, G. J. Expression of blood group-related antigens ABH, Lewis A, Lewis B, Lewis X, Lewis Y, and CA 19-9 in pancreatic cancer cells in comparison with the patient's blood group type. Cancer Res., 48:5422–5426, 1988; Motzer, R. J., Reuter, V. E., Cordon-Cardo, C., and Bosl, G. J. Blood group-related antigens in human germ cell tumors. Cancer Res. 48:5342–5347, 1988).

BR96 and mutant BR96 are different from these antibodies. Although BR96, like other antitumor monoclonal antibodies, binds to some normal cells, their selectivity for tumor, as established by immunohistology on frozen sections is higher than that of most other monoclonal antibodies that we have tested. BR96 is toxic to antigen-positive tumor cells, and whole BR96 mediates both ADCC and CDC (G. J. Schreiber et al., "An Unmodified Anticarcinoma Antibody, BR96, Localizes To and Inhibits Outgrowths of Human Tumors in Nude Mice", Cancer Research 52:3262–3266 (1992).

There is a need for variants of BR96 (i.e., mutant BR96) that exhibit further improved characteristics such as improved specificity for cancer cells, greater binding affinity, greater half-life in serum, or more efficient tumor cell killings. Improved variants of antibodies have been attained through genetic engineering means.

Generally, in order to genetically engineer an antibody molecule or fragment thereof or to create antibody molecules exhibiting enhanced affinities than that of parent antibodies, the following steps are required (1) isolating and cloning the heavy and/or light chain genes from a hybridoma into a vector such as a plasmid, (2) modifying the antibody genes, and (3) transfecting the modified genes into cells that can express them efficiently.

Antibody genes can be modified in a variety of ways. For example, an efficient and quick way to generate a library of mutations in a CDR of an antibody is by codon-based mutagenesis (Glaser, S. M., et al., 1992, J. Immunol. 149:3903–3913). Codon-based oligonucleotide synthesis may yield a vast number of sequences related to the parent phage and corresponding to a selected number of target codons within a CDR so as to produce heavy and light chain libraries.

SUMMARY OF THE INVENTION

The present invention provides mutant BR96 polypeptides (and nucleotide sequences encoding them) having a variable region comprising an amino acid sequence substantially homologous to the variable region of BR96 except for the changes specified herein, such changes increasing the affinity of mutant BR96 to a BR96 antigen.

In one embodiment, the mutant BR96 polypeptide is designated mutant BR96 H3-36. Mutant BR96 H3-36 comprises a variable region having an amino acid sequence which is identical to BR96 except that in mutant BR96 H3-36 the amino acid at position 101 of the heavy chain of CDR3 is alanine. In contrast, the amino acid at position 101 of BR96 is aspartic acid.

In another embodiment, the mutant BR96 polypeptide is designated mutant BR96 H2-60. Mutant BR96 H2-60 comprises a variable region having an amino acid sequence which is identical to BR96 except that in mutant BR96 H2-60 the amino acid at position 54 of the heavy chain of CDR2 is aspartic acid. In contrast, the amino acid at position 54 of BR96 is glycine.

In another embodiment, the mutant BR96 polypeptide is designated mutant BR96 H1-4-3. Mutant BR96 H1-4-3 comprises a variable region having an amino acid sequence which is identical to BR96 except that the amino acid at position 28 is proline (i.e., encoded by CCG) instead of threonine (ACT) in BR96. Moreover, the amino acid at position 30 is alanine (GCG) instead of serine (AGT) in BR96. Further, the amino acid at position 31 is serine (TCG) instead of aspartic acid (GAC). Additionally, the amino acid at position 101 is alanine (GCG). As used herein a sequential numbering system is used when referring to amino acid positions in BR96 and mutant BR96 beginning with amino acid position number 1.

BRIEF DESCRIPTION OF THE FIGURES

FIGS. 1A and 1B are a DNA and amino acid sequence for the variable heavy (SEQ ID NO:1 and SEQ ID NO:2, respectively) and light chains (SEQ ID NO:3 and SEQ ID NO:4, respectively) of BR96.

FIG. 2 is a DNA (SEQ ID NO:5) and amino acid sequence (SEQ ID NO:6) for the variable region of the heavy chain of mutant BR96 H3-36.

FIG. 3 is the DNA (SEQ ID NO:7) and amino acid sequence (SEQ ID NO:8) for the variable region of the heavy chain of mutant BR96 H2-60.

FIG. 4 is a DNA (SEQ ID NO:9) and amino acid sequence (SEQ ID NO:10) for the variable region of the heavy chain of mutant BR96 H1-4-3.

FIG. 5 is a DNA (SEQ ID NO:11) and amino acid sequence (SEQ ID NO:12) for the variable region of the heavy chain of mutant BR96 H2+H3.

DETAILED DESCRIPTION OF THE INVENTION

Definitions

Figure 6:
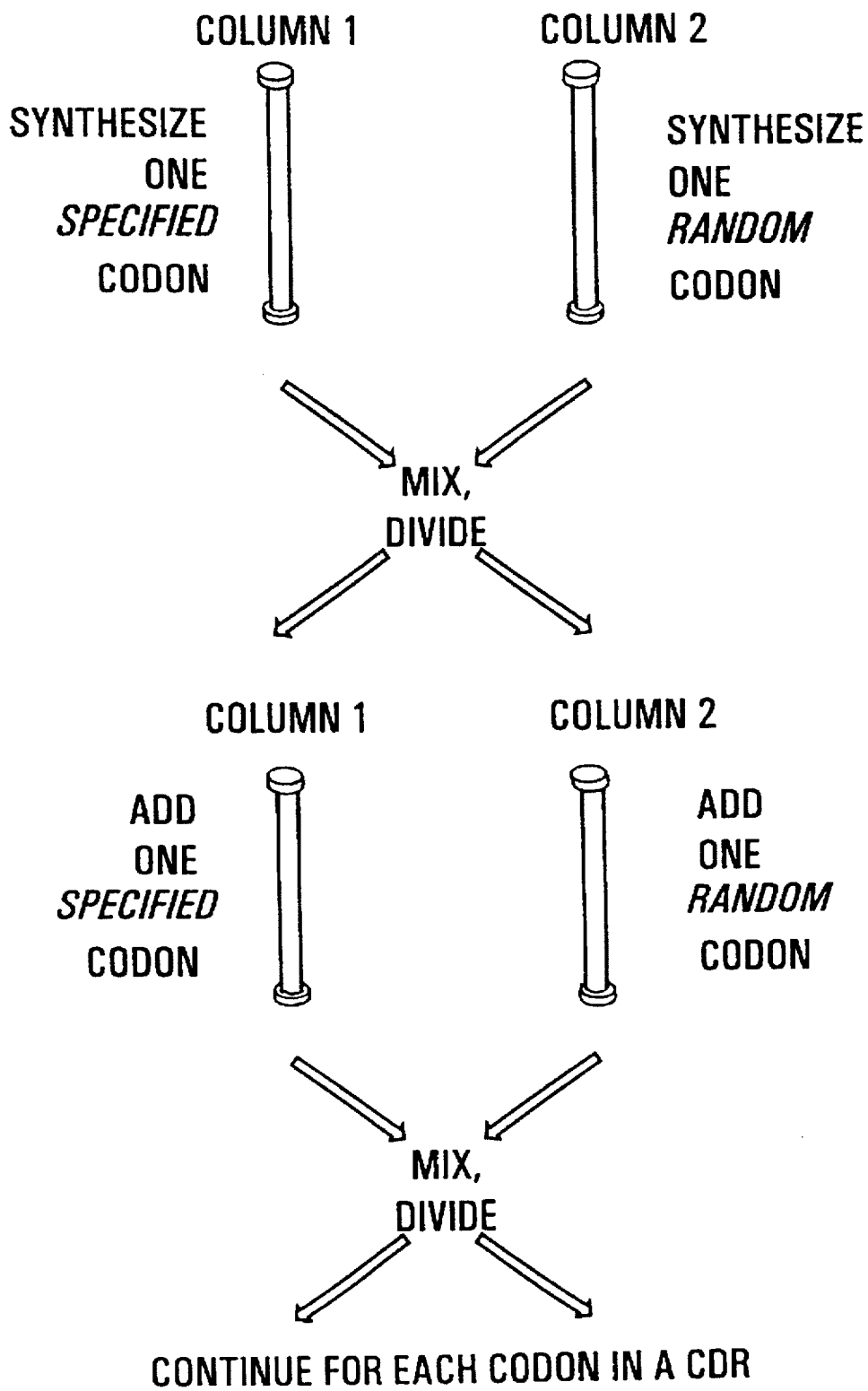
FIG. 6 is a schematic diagram of synthesizing oligonucleotides with CDR mutations (Glaser, S.M., et al., 1992, J. Immunol. 149:3903–3913).

As used herein a "polypeptide" includes protein molecules such as an antibody (e.g., a polyclonal or monoclonal antibody; a bispecific antibody or heteroantibody) and/or functional equivalents thereof such as Fv, Fab, F(ab')$_2$ or variable heavy and/or light chains having an antigen binding site which are produced by proteolytic digests or through recombinant means. A polypeptide may comprise a single amino acid chain. Alternatively, a polypeptide may comprise at least two amino acid chains, associated covalently or noncovalently.

As used herein the term "CDR" means a portion of a polypeptide which is a hypervariable region and/or a region containing amino acids which maintain conformation of the binding loops (also known as CDR loops) of the polypeptide which defines specificity and affinity to an antigen or target.

As used herein the term "BR96" refers to the whole monoclonal antibody disclosed in U.S. Pat. No. 5,491,088, issued Feb. 13, 1996 which comprises both heavy and light chains of the constant regions of any species and fragments thereof possessing equivalent binding specificity, including Fab, F(ab')$_2$, Fv and sFv molecules.

As used herein the term "mutant BR96" means a whole antibody and/or any fragments thereof containing at least the antigen-binding region of the mutant antibody such as Fab, F(ab')$_2$, Fv (including single chain Fv) and fusion proteins and including at least one amino acid change, i.e., by deletion, insertion, or substitution, with respect to the corresponding region of BR96.

As used herein the term "fragment" includes functional derivatives of antibodies and not whole antibodies. Further, the term fragment is not limited to molecules which are obtained through proteolytic cleavage but includes molecules that are produced through recombinant engineering methods.

As used herein "substantially purified" means free of contaminants or isolated from other amino acid residues any of which would inhibit or adversely affect antigen binding.

As used herein "Fab" includes a Fab' molecule and means a monovalent molecule having at least a light chain (V$_L$ and C$_L$) and two amino-terminal heavy chain domains (V$_H$ and C$_{H1}$).

As used herein "F(ab')$_2$" means a divalent molecule composed of two linked Fab' molecules.

As used herein "Fv" means a monovalent molecule made up of a heavy-chain variable domain noncovalently linked to a light-chain variable domain.

As used herein "sFv" means a molecule comprising the variable domain of the light chain (V$_L$) and the variable domain of the heavy chain (V$_H$) attached by a linker peptide(s). The sFv may be generated by any means, e.g., by genetic engineering.

As used herein "Fd" means a molecule having the variable region of the heavy chain (V$_H$) of an immunoglobulin and the amino terminal portion of the constant region of the heavy chain (CH$_1$) of an immunoglobulin.

As used herein a "heteroantibody" means a molecule wherein at least two antibodies are cross-linked together by whatever means, e.g., with reagents such as SPDP or iminothiolane that couple lysine or arginine residues together. Generally, heteroantibodies have at least four antigen-binding sites, two binding sites of each specificity.

As used herein a "bispecific" means a molecule which contains an antigen binding site from two or more antibodies.

As used herein the term "substantially homologous" means an amino acid homology which permits recognition and binding to a BR96 antigen.

As used herein, "treating" means to (1) provide tumor regression so that the tumor is not palpable for a period of time (standard tumor measurement procedures may be followed A. B. Miller et al. "Reporting results of cancer treatment" Cancer 47:207–214 (1981); (2) stabilize the disease; or (3) provide any clinically beneficial effects.

As used herein, "mutation" means a single mutation or multiple mutations by whatever means.

In order that the invention herein described may be more fully understood, the following description is set forth.

The Polypeptide of the Invention

The present invention is directed to mutant BR96 in various forms, i.e., whole antibody, F(ab')$_2$, Fab, Fv, Fc, Fd, or any molecule having at least the antigen binding region of mutant BR96 or having the antigen-binding region which competitively inhibits the immunospecific binding of mutant BR96 to its target antigen.

Mutant BR96 has a variable region substantially homologous to the variable region of BR96. However, there are important differences between them. The differences provide mutant BR96 with an enhanced binding affinity and avidity in comparison to BR96.

The differences between BR96 and mutant BR96 are as follows.

In CDR1 of the heavy chain of BR96, threonine is located at amino acid position 28. Additionally, in CDR1, serine and aspartic acid are located at amino acid positions 30 and 31, respectively. In CDR2 of the heavy chain of BR96, glycine is located at amino acid position 54. Further, in CDR3 of the heavy chain of BR96, aspartic acid is located at amino acid position 101.

In contrast to BR96, mutant BR96 H3-36 Fab (FIG. 2) comprises alanine at position 101 in CDR3 of the heavy chain of mutant BR96 (Table 1).

Further, in contrast to BR96, in CDR1 of the heavy chain of mutant BR96 H1-4-3 (FIG. 4) proline is located at position 28, alanine is located at position 30, serine is located at position 31 and alanine is located at position 101 (Table 1).

Mutant BR96 H2-60 comprises aspartic acid at amino acid 54 in CDR2 of the heavy chain. In contrast, BR96 comprises glycine at the corresponding position.

Mutant BR96 H2+H3 comprises aspartic acid at amino acid 54 in CDR2 and alanine at amino acid position 101 of CDR3 both of the heavy chain. In contrast, BR96 comprises glycine and aspartic acid, respectively, at the corresponding positions.

Functional equivalents or derivatives of mutant BR96 H3-36, H2+H3, and H1-4-3 include any molecule which (1) has an amino acid sequence substantially homologous to the variable region of BR96; (2) is capable of exhibiting increased affinity and enhanced specificity for a BR96 antigen; and/or (3) has at least a single amino acid difference with BR96 at position 101 of the variable region of the heavy chain of BR96.

Additionally, functional equivalents or derivatives of mutant BR96 H2-60 and H2+H3 include any molecule which (1) has an amino acid sequence substantially homologous to the variable region of BR96; (2) is capable of

TABLE 1

| CDR H1 | 26 | 27 | 28 | 29 | 30 | 31 | 32 | 33 |
|---|---|---|---|---|---|---|---|---|
| BR96 | GGA | TTC | ACT | TTC | AGT | GAC | TAT | TAC |
|  | Gly | Phe | Thr | Phe | Ser | Asp | Tyr | Tyr |
| H3-36 | GGA | TTC | ACT | TTC | AGT | GAC | TAT | TAC |
|  | Gly | Phe | Thr | Phe | Ser | Asp | Tyr | Tyr |
| H2-60 | GGA | TTC | ACT | TTC | AGT | GAC | TAT | TAC |
|  | Gly | Phe | Thr | Phe | Ser | Asp | Tyr | Tyr |
| H2+H3 | GGA | TTC | ACT | TTC | AGT | GAC | TAT | TAC |
|  | Gly | Phe | Thr | Phe | Ser | Asp | Tyr | Tyr |
| H1 | GGA | TTC | CCG | TTC | GCG | TCG | TAT | TAC |
|  | Gly | Phe | Pro | Phe | Ala | Ser | Tyr | Tyr |
| H1-4-3 | GGA | TTC | CCG | TTC | GCG | TCG | TAT | TAC |
|  | Gly | Phe | Pro | Phe | Ala | Ser | Tyr | Tyr |

| CDR H2 | 52 | 53 | 54 | 55 | 56 | 57 | 58 | 59 |
|---|---|---|---|---|---|---|---|---|
| BR96 | AGT | CAA | GGT | GGT | GAT | ATA | ACC | GAC |
|  | Ser | Gln | Gly | Gly | Asp | Ile | Thr | Asp |
| H3-36 | AGT | CAA | GGT | GGG | GAT | ATA | ACC | GAC |
|  | Ser | Gln | Gly | Gly | Asp | Ile | Thr | Asp |
| H2-60 | AGT | CAA | GAT | GGT | GAT | ATA | ACC | GAC |
|  | Ser | Gln | Asp | Gly | Asp | Ile | Thr | Asp |
| H2+H3 | AGT | CAA | GAT | GGT | GAT | ATA | ACC | GAC |
|  | Ser | Gln | Asp | Gly | Asp | Ile | Thr | Asp |
| H1 | AGT | CAA | GGT | GGT | GAT | ATA. | ACC | GAC |
|  | Ser | Gln | Gly | Gly | Asp | Ile | Thr | Asp |
| H1-4-3 | AGT | CAA | GGT | GGT | GAT | ATA | ACC | GAC |
|  | Ser | Gln | Gly | Gly | Asp | Ile | Thr | Asp |

| CDR H3 | 99 | 100 | 101 | 102 | 103 | 104 | 105 |
|---|---|---|---|---|---|---|---|
| BR96 | GGC | CTG | GAC | GAC | GGG | GCC | TGG |
|  | Gly | Leu | Asp | Asp | Gly | Ala | Trp |
| H3-36 | GGC | CTG | GCG | GAC | GGG | GCC | TGG |
|  | Gly | Leu | Ala | Asp | Gly | Ala | Trp |
| H2-60 | GGC | CTG | GAC | GAC | GGG | GCC | TGG |
|  | Gly | Leu | Asp | Asp | Gly | Ala | Trp |
| H2+H3 | GGC | CTG | GCG | GAC | GGG | GCC | TGG |
|  | Gly | Leu | Ala | Asp | Gly | Ata | Trp |
| H1 | GGC | CTG | GAC | GAC | GGG | GCC | TGG |
|  | Gly | Leu | Asp | Asp | Gly | Ala | Trp |
| H1-4-3 | GGC | CTG | GCG | GAC | GGG | GCC | TGG |
|  | Gly | Leu | Ala | Asp | Gly | Ala | Trp | exhibiting increased affinity and enhanced specificity for a BR96 antigen; and/or (3) has at least a single amino acid difference with BR96 at position 54 of the variable region of the heavy chain of BR96.

Mutant BR96 molecules having more than a single amino acid mutation as compared to BR96 are encompassed within this invention.

Depending on its form, mutant BR96 may be a monofunctional antibody, such as a monoclonal antibody, or bifunctional antibody, such as a bispecific antibody or a heteroantibody. The uses of mutant BR96, i.e., as a therapeutic or diagnostic agent, will determine the different forms of mutant BR96 which is made.

For example, antibody fragments may be desirable in one instance so as to circumvent nonspecific binding to Fc receptors on cells (a potentially advantageous characteristic in a number of medical applications such as diagnostic imaging with labeled antibodies). In other instances, specific Fc effector functions may be desired.

In this regard it is possible to reintroduce each mutation singly and in combination into an expression system, e.g., a mammalian expression system.

Several options exists for antibody expression. Immunoexpression libraries can be combined with transfectoma technology, i.e., the genes for the Fab molecules derived from the immunoglobulin gene expression library can be connected to the desired constant-region exons. These recombinant genes can then be transfected and expressed in a transfectoma that would secrete the whole antibody molecule.

Once produced, the polypeptide of the invention (e.g., mutant BR96 and/or functional equivalents thereof) may be modified, i.e., by amino acid modifications within the molecule, so as to produce derivative molecules. Such derivative molecules would retain the functional property of the polypeptide, namely, the molecule having such substitutions will still permit the binding of the polypeptide to the BR96 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

In one embodiment of the present invention, the polypeptide is substantially pure, i.e., free of other amino acid residues which would inhibit or diminish binding of the polypeptide to its target.

Nucleic Acid Molecules Encoding the Present Invention

The nucleotide and the amino acid sequences of the antigen binding site or the variable region of both the heavy and light chains of BR96 are known. By standard sequencing techniques the entire nucleotide and amino acid sequence of BR96 is discernable.

The nucleic acid sequence of the variable region of mutant BR96 is substantially homologous to that of BR96.

In BR96, threonine at amino acid position 28 is encoded by the codon ACT. Additionally, serine and aspartic acid at amino acid positions 30 and 31 are encoded by codons AGT and GAC, respectively. Further, aspartic acid at amino acid position 101 is encoded by codon GAC.

Mutant BR96 H3-36 comprises alanine at position 101 and is encoded by the codon GCG. Other codons which encode alanine are encompassed by the present invention, namely, GCT, GCC, or GCA. Further, in other embodiments of mutant BR96 polypeptide, amino acid position 101 of CDR3 of the heavy chain may contain an amino acid selected from the group consisting of alanine, arginine, serine, glycine, tyrosine, and valine. This is illustrated as follows.

| Clone | Binding Phenotype | Codon | Amino acid |
| --- | --- | --- | --- |
| 1 | high | GTT/GCT | Ala/Val |
| 7 | high | CGT | Arg |
| 8 | high | TCT | Ser |
| 9 | high | CGT | Arg |
| 10 | high | TCT | Ser |
| 13 | high | GGG | Gly |
| 14 | high | GGT | Gly |
| 15 | high | GCT | Ala |
| 16 | high | CGT | Arg |
| 20 | high | TCT | Ser |
| 24 | high | GCG | Ala |
| 28 | high | TAT | Tyr |
| 30 | high | AGT | Ser |
| 31 | high | GTG | Val |
| 32 | high | TCT | Ser |
| 33 | high | CGG | Arg |
| 34 | high | GTG | Val |

Mutant BR96 H1-4-3 comprises proline at position 28, alanine at position 30, and serine at position 31 encoded by codons CCG, GCG, and TCG, respectively (Table 1). Additionally, in contrast to BR96, alanine at position 101 is encoded by the codon GCG. Other codons encoding proline (CCT, CCC, CCA), alanine (GCT, GCC, GCA), and serine (TCT, TCC, TCA, AGT, AGC) are encompassed in this invention.

Mutant BR96 H2-60 comprises aspartic acid at position 54 of the heavy chain of CDR2 encoded by codon GAT or GAC (Table 1).

Additionally, mutant BR96 H2+H3 comprises aspartic acid at position 54 of the heavy chain of CDR2 encoded by codon GAT or GAC (Table 1). Further, it comprises alanine at position 101 of CDR3 of the heavy chain encoded by codon GCG, GCT, GCC, or GCA.

The nucleic acid of the invention at least encodes the variable domain of mutant BR96 comprising the antigen binding site.

The nucleic acid may be deoxyribonucleic acid (DNA), e.g., complementary DNA (cDNA), or ribonucleic acid (RNA). DNA is preferred.

Fusion Proteins

Similarly, a fusion protein comprising at least the antigen-binding region of the mutant BR96 antibody joined to at least a functionally active portion of a second protein having anti-tumor activity, e.g., a toxin, lymphokine, or oncostatin can be used to treat human carcinoma in vivo. Furthermore, recombinant techniques known in the art can be used to construct bispecific antibodies with a binding specificity for two different antigens, one of the antigens being that with which the monoclonal antibody BR96 produced by hybridoma ATCC HB10036 binds (U.S. Pat. No. 4,474,893 (incorporated by reference)) while the other binding specificity of the antibody is that of a molecule other than BR96. Bispecific antibodies including the variable region of mutant BR96 may be constructed using this methodology.

Anti-ID Antibodies of the Mutant BR96 Antibody

An anti-idiotypic antibody of BR96 has been produced. The protocol for producing anti-idiotypes is well known (Farid and Lo (1985)

Anti-idiotypic antibodies as probes for receptor structure and function. Endocr. Rev. 6:1–23). These protocols may be used to produce anti-id antibodies of mutant BR96.

Further, anti-idiotypic antibodies of the mutant BR96 antibodies may be used therapeutically in active tumor immunization and tumor therapy (e.g., Hellstrom et al., "Immunological Approaches To Tumor Therapy: Monoclonal Antibodies, Tumor Vaccines, And Anti-Idiotypes", in *Covalently Modified Antigens And Antibodies In Diagnosis And Therapy*, supra at pp. 35–41).

Immunoconjugates

Immunoconjugates have been constructed using chemotherapeutic agents such as methotrexate and chlorambucil (Smyth et al., "Specific Targeting of Chlorambucil to Tumors With the Use of Monoclonal Antibodies", J. Natl. Cancer Inst., 76:503–510 (1986), in a variety of anthracyclines including doxorubicin (DOX) (Yang and Reisfeld "Doxorubicin Conjugated with a Monoclonal Antibody Directed to a Human Melanoma-Associated Proteoglycan Suppresses Growth of Established Tumor xenografts in Nude Mice PNAS (USA)" 85:1189–1193 (1988), Daunomycin (Arnon and Sela "In Vitro and in vivo Efficacy of Conjugates of Daunomycin With Anti-Tumor Antibodies" Immunol. Rev., 65:5–27 (1982) and morpholinodoxorubicin (Mueller et al., "Antibody Conjugates With Morpholinodoxorubicin and Acid-Cleavable Linkers", Bioconjugate Chem., 1:325–330 (1990).

BR96 conjugated to doxorubicin has been shown to be effective in therapy of certain cancers or carcinomas (Trail, P. A., Willner, D., Lasch, S. J., Henderson, A. J., Casazza, A. M., Firestone, R. A., Hellström, I., and Hellström, K. E. Cure of xenografted human carcinomas by BR96-doxorubicin immunoconjugates. Science, 261:212–215, 1993).

In accordance with the practice of the invention, mutant BR96 may be used in forms including native mutant IgG, reduced mutant IgG, mutant F(ab')$_2$, sFv, fusion proteins, and mutant Fab.

Suitable therapeutic agents for the immunoconjugate includes Pseudomonas exotoxin A (PE) in either the native PE or LysPE40 form. LysPE40 is a truncated form containing a genetically modified amino terminus that includes a lysine residue for conjugation purposes. Doxorubicin is also a suitable therapeutic agent.

Genetic engineering techniques known in the art are used as described herein to prepare recombinant immunotoxins produced by fusing antigen binding regions of mutant BR96 to a cytotoxic agent at the DNA level and producing the cytotoxic molecule as a chimeric protein.

These fusion proteins combine the specificity of the cell binding portion of the immunoglobuin molecule with the cytotoxic potential of the toxin. In a preferred embodiment, a single-chain immunotoxin molecule, mutant BR96 sFV-PE40 may be prepared consisting of the cloned heavy or light chain Fv portions from mutant BR96, linked to PE40.

This single chain immunotoxin is cloned and expressed, and shown to possess cytotoxic activity towards carcinoma cell lines that express a BR96 antigen on their surface.

Single chain immunotoxins such as mutant BR96 sFv-PE40 are expressed as a single molecule. They have advantages over conjugates produced by protein fusions of toxins to immunoglobulins. Single chain immunotoxins are more readily produced because no fusion step is required after the production of the recombinant immunoglobulin fragment. Additionally, they generate a population of homogenous molecules, i.e., single peptides composed of the same amino acid residues. Moreover, because of the toxin or drug, the conjugate is more potent than non-conjugated mutant BR96.

The techniques for cloning and expressing DNA sequences encoding the amino acid sequences corresponding to the single-chain immunotoxin mutant BR96 sFv-PE40, e.g., synthesis of oligonucleotides, PCR, transforming cells, constructing vectors, expression systems, and the like are well-established in the art, and most practitioners are familiar with the standard resource materials for specific conditions and procedures (e.g., Sambrook et al., eds., Molecular Cloning, A Laboratory Manual, 2nd Edition, Cold Spring Harbor Laboratory Press (1989)).

Details of the construction of the (1) single-chain recombinant immunotoxin of the invention are provided in Examples 3 and 4, and (2) mutant BR96 sFv-PE40 fusion protein are provided in Example 5, infra.

Briefly, for example, to construct the single chain mutant BR96 construct, polymerase chain reaction (PCR) (Mullis et al., U.S. Pat. Nos. 4,683,195 and 4,683,202; Mullis and Faloona, *Methods Enzymol.* 154:335–350 (1987)) is used to amplify an approximately 550 bp mutant BR96 sFv sequence. The PCR is carried out using primers whose sequence is deduced from the BR96 sequence and which will sepecifically amplify the sFv region. The primers additionally carry recognition sites for restriction enzymes to be used for subsequent cloning of the PCR product. The restriction enzymes that are chosen are those that do not recognize a sequence in the sequence to be amplified.

After PCR amplification, the approximately 550 bp fragment is digested with restriction enzymes recognizing sites in the primers and ligated using standard procedures into a fragment from a vector, e.g., pMS8 (Covell et al., *Cancer Res.* 46:3969–3978 (1986)) encoding the PE40 gene to form an intermediate vector.

A fragment from mutant BR96 Fv is then subcloned into the intermediate vector to form a plasmid encoding the mutant BR96 sFv-PE40 gene fusion. The construction is confirmed by DNA sequence analysis using known procedures (Sanger et al., *Proc. Natl. Acad. Sci. USA* 74:5463 (1977) and Messing et al. *Nucleic Acids Res.* 9:309 (1981)).

Expression and Purification of Mutant BR96

The DNA sequences encoding mutant BR96 may be propagated and expressed in a variety of systems as set forth below. The DNA may be excised from the intermediate vector by suitable restriction enzymes and ligated into suitable expression vectors for such expression.

Depending on the host cell used, mutant BR96 is cloned into the appropriate vector. Transformation or transfection is performed using standard techniques appropriate for the particular host cell.

Expression of Mutant BR96 in Prokaryotic Cells

Expression of mutant BR96 in prokaryotic cells is preferred for some purposes. Examples of mutant BR96 includes Fab, sFv, sFv-fusion proteins including sFv-toxins.

Prokaryotes most frequently are represented by various strains of bacteria. The bacteria may be a gram positive or a gram negative. Typically, gram-negative bacteria such as E. coli are preferred. Other microbial strains may also be used.

Sequences encoding mutant BR96 have been inserted into a vector designed for expressing foreign sequences in procaryotic cells such as E. coli. These vectors will include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived $P_L$ promoter and N-gene ribosome binding site (Shimatake et al., Nature 292:128 (1981)). Such vectors will also include origins of replication and selectable markers, such as a beta-lactamase or neomycin phosphotransferase gene conferring resistance to antibiotics so that the vectors can replicate in bacteria and cells carrying the plasmids can be selected for when grown in the presence of ampicillin or kanamycin.

The expression plasmid can be introduced into prokaryotic cells via a variety of standard methods, including but not limited to $CaCl_2$-shock (see Cohen, Proc. Natl. Acad. Sci. USA (1972) 69:2110, and Sambrook et al. (eds.), Molecular Cloning: A Laboratory Manual, 2nd Edition, Cold Spring Harbor Press, (1989)) and electroporation.

Expression of Mutant BR96 in Eukaryotic Cells

In accordance with the practice of the invention, eukaryotic cells are also suitable host cells.

Examples of eukaryotic cells include any animal cell, whether primary or immortalized, yeast (e.g., Saccharomyces cerevisiae, Schizosaccharomyces pombe, and Pichia pastoris), and plant cells. Myeloma, COS and CHO cells are examples of animal cells that may be used as hosts. Exemplary plant cells include tobacco (whole plants or tobacco callus), corn, soybean, and rice cells. Corn, soybean, and rice seeds are also acceptable.

Sequences encoding the mutant BR96 will be inserted into a vector designed for expressing foreign sequences in a eukaryotic host. The regulatory elements of the vector will vary according to the particular eukaryotic host.

Commonly used eukaryotic control sequences include promoters and control sequences compatible with mammalian cells such as, for example, CMV promoter (CDM8 vector) and arian sarcoma virus (ASV) (πLN vector). Other commonly used promoters include the early and late promoters from Simian Virus 40 (SV 40) (Fiefs, et al., Nature 273:113 (1973)), or other viral promoters such as those derived from polyoma, Adenovirus 2, and bovine papilloma virus. An inducible promoter, such as hMTII (Karin, et al., Nature 299:797-802 (1982)) may also be used.

Vectors for expressing mutant BR96 in eukaryotes may also carry sequences called enhancer regions. These are important in optimizing gene expression and are found either upstream or downstream of the promoter region.

Sequences encoding mutant BR96 may integrate into the genome of the eukaryotic host cell and replicate as the host genome replicates. Alternatively, the vector carrying mutant BR96 may contain origins of replication allowing for extrachromosomal replication.

For expressing the sequences in Saccharomyces cerevisiae, the origin of replication from the endogenous yeast plasmid, the 2µ circle could be used. (Broach, Meth. Enz. 101:307 (1983). Alternatively, sequences from the yeast genome capable of promoting autonomous replication could be used (see, for example, Stinchcomb et s.al., Nature 282:39 (1979)); Tschemper et al., Gene 10:157 (1980); and Clarke et al., Meth. Enz. 101:300 (1983)).

Transcriptional control sequences for yeast vectors include promoters for the synthesis of glycolytic enzymes (Hess et al., J. Adv. Enzyme Reg. 7:149 (1968); Holland et al., Biochemistry 17:4900 (1978)). Additional promoters known in the art include the CMV promoter provided in the CDM8 vector (Toyama and Okayama, FEBS 268:217-221 (1990); the promoter for 3-phosphoglycerate kinase (Hitzeman et al., J. Biol. Chem. 255:2073 (1980)), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Exemplary vectors for plants and plant cells include but are not limited to Agrobacterium $T_i$ plasmids, cauliflower mosaic virus (CaMV), tomato golden mosaic virus (TGMV).

General aspects of mammalian cell host system transformations have been described by Axel (U.S. Pat. No. 4,399,216 issued Aug. 16, 1983). Mammalian cells be transformed by methods including but not limited to, transfection in the presence of calcium phosphate, microinjection, electorporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making protoplasts permeable to macromolecules through polyethylene glycol treatment or subjection to high voltage electrical pulses (electroporation); or (3) the use of liposomes (containing cDNA) which fuse to protoplasts.

Identification and Recovery of Mutant BR96

Expression of mutant BR96 is detected by Coomassie stained SDS-PAGE and immunoblotting using either antiidiotypic antibodies that bind BR96, or in the case of mutant BR96 immunoconjugates, antibodies that bind to non-mutant BR96 parts of the conjugate. Protein recovery is effected by standard protein purification means, e.g., affinity chromatography or ion-exchange chromatography, to yield substantially pure product (R. Scopes Protein Purification, Principles and Practice, Third Edition Springer-Verlag (1994)).

A recombinant mutant BR96 immunotoxin may be produced along with a signal sequence that causes a sFv-toxin to be secreted. The signal sequence will be chosen so that the host cell is capable of processing this sequence. For expression in prokaryotic hosts, the signal may additionally be chosen so it directs the sFv-toxin fusion to the periplasmic space. Alternatively, the protein may be produced without a signal sequence, recovered from the cytoplasm, then refolded using denaturation agents such as urea to give biologically active material (i.e., protein or antibody). The immunotoxin is recovered using standard protein purification techniques such as anion-exchange and gel-filtration chromatography (Siegall et al., *Proc. Natl. Acad. Sci. USA* 85:9738–9742 (1988)).

Methods of Making the Present Invention

DNA sequences encoding BR96-variants with increased affinity for the Le$^Y$ antigen were constructed and isolated using the following strategy.

The basic approach was to construct altered BR96 molecules containing mutations in the CDR of the $V_H$ and $V_L$ chains and then ask which of these mutants showed enhanced binding to the Le$^Y$ antigen. To do this, a mixture of oligonucleotides encoding amino acids in the complementarity-determining region was annealed to a single-stranded template carrying disabled $V_L$ and $V_H$ BR96 coding sequences. The template strands with the annealed oligonucleotides encoding variant CDR regions were then converted to double-stranded form with DNA polymerase and ligase. The ligation products were then transformed into *E. coli*, and transformants were screened for reactivity with Le$^Y$.

The following sections discuss in more detail the construction of the M13-derived parent immunoexpression vector containing the BR96 $V_L$ and $V_H$ coding sequences and the method for constructing sequence variants in the CDR regions.

1. Construction of AN M13 Immunoexpression Containing the BR96 $V_H$ and $V_L$ Regions Disabled BR96 coding sequences are those that contain a premature stop codon inserted into the CDR region to be mutated. Because such sequences would not produce a functional protein, they would not bind to Le$^Y$ antigen. This facilitated screening of mutants, since only altered sequences that replaced the stop codon and produced Le$^Y$-binding proteins would be detected.

M13 was used as a cloning vector because in subsequent steps of the mutagenesis procedure it was necessary to isolate single-stranded DNA. In particular, it was desirable to distinguish between DNA strands corresponding to the parent molecule from DNA strands carrying novel sequences.

BR96 V$^H$ or $V_L$ sequences were inserted into the M13 vector using the polymerase chain reaction (PCR) and a method termed hybridization mutagenesis. This method enables substitution of one DNA molecule with a second, homologous sequence (Near, R. 1992. *Biotechniques* 11:88–97).

PCR is an in vitro method of nucleic acid synthesis by which a particular segment of DNA can be specifically replicated. PCR involves two oligonucleotide primers that flank the DNA fragment to be amplified and repeated cycles of denaturation of the DNA, annealing of the primers to their complementary sequences, and extension of the annealed primers with DNA polymerase.

These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment.

The products of PCR amplification can then be recloned into a second vector using a process called hybridization mutagenesis. This method requires that a recipient vector contain regions of homology to the donor PCR amplified $V_L$ and $V_H$ sequences. The recipient vector must also exist in a single-stranded DNA form. The donor amplified sequence is phosphorylated, denatured and then annealed to the donor template. After chain extension with DNA polymerase and ligation, the resulting ligation products are introduced into *E. coli*, and the desired recombinants identified.

To bias the procedure in favor of recovering recombinants incorporating donated sequences, the host template is prepared in a dut$^-$ ung$^-$ *E. coli* strain. Strains carrying these mutations incorporate uracil into DNA molecules instead of thymidine. When DNA molecules are reintroduced into dut$^+$ung$^+$ strains, uracil-containing DNA molecules are degraded. Thus, only the donor strand from the PCR amplified $V_L$ and/or $V_H$ BR96 sequences will replicate.

The requirement for homology is satisfied in the present invention because the parent M13 vector, M13IXL604, contains sequences encoding the L6 antibody, and L6 is highly homologous to BR96.

The primary advantage of introducing the $V_L$ and $V_H$ segments with the hybridization mutagenesis method is that restriction endonuclease sites do not need to be incorporated into the $V_L$ or $V_H$ gene sequences for cloning as is done with conventional DNA ligation methods. This eliminates the possibility of introducing amino acid residues encoded by the restriction site that could adversely affect antigen binding.

BR96 $V_L$ and $V_H$ chain sequences were amplified using PCR, and the full-length products were recovered from an acrylamide gel. The products were phosphorylated, denatured and annealed to a single-stranded DNA template carrying L6 sequences, M13IXL604. The M13IXL604 template had been isolated from a dut$^-$ ung$^-$ *E. coli* strain.

After DNA synthesis using the annealed BR96 sequences on the M13IXL604 template and ligation, the ligation products were introduced into a dut$^+$ung$^+$ strain.

Introduction of the amplified $V_L$ and $V_H$ sequences by PCR followed by hybridization mutagenesis positioned the antibody-encoding sequences in frame with the regulatory elements of the M13 vector required for efficient Fab expression.

2. Preparing the Recipient Vector So As To Produce a Single M13 Construct Encoding Both BR96 Heavy and Light Chains M13IXL604, a M13 phage to be used as a recipient vector, is conveniently crippled for antibody or protein expression by introducing a deletion and stop codon into a CDR of $V_L$ and $V_H$ prior to introducing BR96 variable regions. This was done to facilitate screening, as only recombinants incorporating BR96 sequences will express functional proteins.

Recombinants in which the BR96 $V_L$ chain sequences had been transferred to the M13IXL604 vector were identified by screening transformants for reactivity with a human anti-kappa light chain antibody. This antibody recognizes mutant BR96 light chains but not crippled L6. One such clone, M13IX BR96$V_L$-2, was identified and the construction verified by DNA sequencing.

BR96$V_H$ sequences were then introduced into dut⁻ ung⁻ prepared M13IX BR96$V_L$-2 single-stranded DNA using the PCR and hybridization mutagenesis procedure described above.

Recombinants incorporating the BR96 $V_H$ sequences into BR96$V_L$-2 were identified by screening for reactivity to a murine monoclonal antibody recognizing the decapeptide, Tyr Pro Tyr Asp Val Pro Asp Tyr Ala Ser (SEQ ID NO:13). Because this sequence was encoded downstream of the premature stop codon, it will not be expressed in the BR96$V_L$-2 parent. It will be expressed, however, if the premature stop codon is replaced by BR96 $V_H$ sequences inserted in the proper reading frame.

It would be clear to one skilled in the art that tags other than the decapeptide with the stated sequence (SEQ ID NO:13) are available and may be used for the same purpose.

To verify that M13IX BR96 13.24 expressed proteins reactive with those known to react with BR96, it was expressed in *E. coli* and Fab molecules were isolated. These were found to bind specifically to to H3396, a breast adenocarcinoma cell lines expressing Le$^Y$.

In a final step in constructing the vector for generating modifications in BR96, the $V_L$ and $V_H$ sequences in M13IX BR96 13.24 were disabled by introducing a deletion and premature stop codon into each the CDR regions of each chain using site-directed mutagenesis. The parental vector would therefore express Le$^Y$-reactive antibody and screening of altered-affinity mutants would be facilitated.

3. Construction of Codon-Based Mutagenized Libraries

To synthesize and screen BR96 variants with altered affinities for Le$^Y$ antigen, a two-step strategy was adopted. The experiments entailed first generating a large library of mutations in the CDR regions of the $V_L$ and $V_H$ coding and then screening these by replicate filter lift assays to Le$^Y$ antigen, followed by ELISA to H3396 tumor cells to identify mutants with altered reactivity to a BR96 antigen.

The CDR libraries were constructed using a technique called codon-based mutagenesis (Glaser, S. M., et al., 1992, *J. Immunol.* 149:3903–3913). This procedure was chosen for several reasons. First, it required minimal information. The only requirements of codon-based mutagenesis are knowledge of the primary DNA sequence to be mutated and a functional assay for the target antigen. Codon-based mutagenesis does not require prior structural information and postulation of particular amino acid substitutions likely to yield the desired result. Of course, where structural information does exist, it can be exploited in designing codon-based mutagenesis strategies.

Codon-based oligonucleotide synthesis may yield a vast number of completely random sequences corresponding to the selected number of target codons within a heavy or light chain CDR.

Since the number of possible mutations is potentially large, it is desirable to limit the number of positions considered for mutation. Preferentially, only regions of CDR loops that are solvent accessible and thus antigen accessible were mutated by codon-based mutagenesis. Other regions of the molecule, such as the junctions between CDR loops and framework residues may be important for improving loop orientation.

A second advantage of codon-based mutagenesis lies in the efficiency with which it generates mutants encompassing all amino acids at each codon. Codon-based mutagenesis replaces entire codons rather than individual nucleotides. The technique is especially efficient if a mutagenesis strategy is based on permutations of the trinucleotide sequence XXG/T; the 32 potential codons in this sequence encode all 20 amino acids and one stop codon. Thus, mutations can be introduced more efficiently than by random introduction of nucleotides.

To employ the codon-based mutagenesis strategy on the CDR regions of BR96 $V_L$ and $V_H$, it was necessary to determine which CDR regions to mutate and how extensive the region should be mutated.

A 50% level of substitution at each codon in the CDR was arbitrarily chosen. The choice of which codons within a CDR loop to mutate was based on a computer model of BR96.

Synthesis of the collection of codons encoding novel amino acid sequences in the CDR loops took place on beads that were alternatively placed into one of two DNA synthesizing columns. The beads made it possible to easily transfer nascent oligonucleotides between the two columns. The synthesis occurred as follows (FIG. 6):

1. A trinucleotide for a predetermined or "parental" codon sequence found at a selected position was synthesized on column 1.
2. A trinucleotide for a random XXG/T codon, where X represents a mixture of dA, dG, dC, and T cyanoethyl phosphoramidites, and G/T represents a mixture of dG and dC cyanoethyl phosphoramidites was synthesized on column 2.
3. Beads from the two columns were mixed after synthesis of each codon.
4. The mixed beads were then divided in half.
5. Each half was then loaded onto a new column.
6. The columns were returned to the DNA synthesizer, and steps 1–4 were repeated for the subsequent CDR positions.
7. After the final synthesis step, the contents of the pool the two columns were pooled, and the oligonucleotides were recovered and purified.

The resulting oligonucleotides were used for mutagenizing $V_H$ and $V_L$ CDRs of BR96. A total of six codon-based mutagenesis libraries in BR96 were constructed, each library containing a different mutagenized CDR.

These synthetic oligonucleotides are designed to contain all possible desired mutations in complementary orientation to the parental phage which contains the variable light or heavy chain of the BR96 immunoglobulin.

4. Identification of Variant BR96 Molecules with Altered Binding

The mutant BR96 library is screened to identify desired mutants. After identifying a mutation of interest, the mutation may be reintroduced into the parental vector. This will confirm whether the mutation is necessary and sufficient to confer the desired phenotype. Additionally, the mutation may be reintroduced into the parental vector in order to produce other forms of the molecule suitable for whatever application is necessary, i.e., diagnostic or therapeutic applications. The use will determine the form of mutant BR96, e.g., Fab, Fv, F(ab')$_2$, fusion protein, and bispecific antibodies.

The above-described method is merely one means to produce mutant BR96. Other methods well known in the art are possible (Foot and Winter, Mol. Biol (1992) 224:487–499).

METHODS OF USING THE PRESENT INVENTION

1. Diagnostic Techniques

The mutant BR96 antibody of the invention is useful for diagnostic applications, both in vitro and in vivo, for the detection of human carcinomas that possess the antigen for which the antibodies are specific. In vitro diagnostic methods include immunohistological detection of tumor cells (e.g., on human tissue, cells or excised tumor specimens) or serologic detection of tumor-associated antigens (e.g., in blood samples or other biological fluids).

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassay (RIA) or enzyme-linked immunosorbent assays (ELISA) wherein an antibody reactive with the "shed" antigen is used to detect the presence of the antigen in a fluid sample (see, e.g., Uotila et al., "Two-Site Sandwich ELISA With Monoclonal Antibodies To Human AFP", *J. Immunol. Methods*, 42:11 (1981) and Allum et al., supra at pp. 48–51). These assays, using the mutant BR96 antibodies disclosed herein, can therefore be used for the detection in biological fluids of the antigen with which the mutant BR96 antibodies react and thus the detection of human carcinoma in patients. Thus, it is apparent from the foregoing that the mutant BR96 antibodies of the invention can be used in most assays involving antigen-antibody reactions. These assays include, but are not limited to, standard RIA techniques, both liquid and solid phase, as well as ELISA assays, immunofluorescence techniques, and other immunocytochemical assays (see, e.g., Sikora et al. (eds.), *Monoclonal Antibodies*, pp. 32–52 (Blackwell Scientific Publications 1984)).

Immunohistochemical techniques involve staining a biological specimen such as a tissue specimen with the mutant BR96 antibody of the invention and then detecting the presence on the specimen of the antibody complexed to its antigen. The formation of such antibody-antigen complexes with the specimen indicates the presence of carcinoma cells in the tissue. Detection of the antibody on the specimen can be accomplished using techniques known in the art such as immunoenzymatic techniques, e.g., the immunoperoxidase staining technique or the avidin-biotin (ABC) technique, or immunofluorescence techniques (see, e.g., Ciocca et al., "Immunohistochemical Techniques Using Monoclonal Antibodies", *Meth. Enzymol.*, 121:562–79 (1986); Hellstrom et al., "Monoclonal Mouse Antibodies Raised Against Human Lung Carcinoma", *Cancer Research*, 46:3917–23 (1986); and Kimball (ed.), *Introduction to Immunology* (2nd Ed.), pp. 113–117 (Macmillan Pub. Co. 1986)). For example, immunoperoxidase staining was used to demonstrate the reactivity of the mutant BR96 antibody with lung, breast, colon, and ovary carcinomas and the low reactivity of the antibody with normal human tissue specimens.

The invention also encompasses diagnostic kits for carrying out the assays described above. In one embodiment, the diagnostic kit comprises the mutant BR96 monoclonal antibody, fragments thereof, fusion proteins, bispecific antibody or chimeric antibody of the invention, and a conjugate comprising a specific binding partner for the mutant BR96 antibody and a label capable of producing a detectable signal. The reagents can also include ancillary agents such as buffering agents and protein stabilizing agents (e.g., polysaccharide). The diagnostic kit can further comprise, where necessary, other components of the signal-producing system including agents for reducing background interference, control reagents or an apparatus or container for conducting the test. In another embodiment, the diagnostic kit comprises a conjugate of the mutant BR96 antibodies of the invention and a label capable of producing a detectable signal. Ancillary agents as mentioned above can also be present.

The mutant BR96 antibody of the invention is also useful for in vivo diagnostic applications for the detection of human carcinomas. One such approach involves the detection of tumors in vivo by tumor imaging techniques. According to this approach, the mutant BR96 antibody is labeled with an appropriate imaging reagent that produces a detectable signal. Examples of imaging reagents that can be used include, but are not limited to, radiolabels such as $^{131}$I, $^{111}$In, $^{123}$I, $^{99m}$Tc, $^{32}$P, $^{125}$I, $^{3}$H, and $^{14}$C, fluorescent labels such as fluorescein and rhodamine, and chemiluminescent substrates such as luciferin. The antibody can be labeled with such reagents using techniques known in the art. For example, see Wensel and Meares, *Radioimmunoimaging And Radioimmunotherapy*, Elsevier, N.Y. (1983) for techniques relating to the radiolabeling of antibodies (see also, Colcher et al., "Use of Monoclonal Antibodies As Radiopharmaceuticals For The Localization Of Human Carcinoma Xenografts In Athymic Mice", *Meth., Enzymol.*, 121:802–16 (1986)).

In the case of radiolabeled antibody, the antibody is administered to the patient, localizes to the tumor bearing the antigen with which the antibody reacts, and is detected or "imaged" in vivo using known techniques such as radionuclear scanning using, e.g., a gamma camera or emission tomography (see, e.g., Bradwell et al., "Developments In Antibody Imaging", in *Monoclonal Antibodies For Cancer Detection And Therapy*, Baldwin et al. (eds.), pp. 65–85 (Academic Press 1985)). The antibody is administered to the patient in a pharmaceutically acceptable carrier such as water, saline, Ringer's solution, Hank's solution or nonaqueous carriers such as fixed oils. The carrier may also contain substances that enhance isotonicity and chemical stability of the antibody such as buffers or preservatives. The antibody formulation is administered, for example, intravenously, at a dosage sufficient to provide enough gamma emission to allow visualization of the tumor target site. Sufficient time should be allowed between administration of the antibody and detection to allow for localization to the tumor target. For a general discussion of tumor imaging, see Allum at al., Supra at pp. 51–55.

2. Therapeutic Applications of the Antibodies of the Invention and Fragments Thereof Like BR96, the properties of the mutant BR96 antibodies: a) very high specificity for tumor cells; b) internalization; c)

toxicity to antigen-positive tumor cells alone, i.e., in unmodified form, when used at appropriate concentrations; and d) (in the case of antibodies or functional equivalents having an Fc portion) complement-dependent cytotoxicity and antibody-dependent cellular cytotoxicity activity, suggest a number of in vivo therapeutic applications. First, the mutant BR96 antibody can be used alone to target and kill tumor cells in vivo.

Functional equivalents of mutant BR96 antibody which do not include the Fc region do not exhibit ADCC or CDC properties.

The antibody can also be used in conjunction with an appropriate therapeutic agent to treat human carcinoma. For example, the antibody can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma.

Techniques for conjugating such therapeutic agents to antibodies are well known (see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243–56 (Alan R. Liss, Inc. 1985); Hellstrom et al., "Antibodies For Drug Delivery", in *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475–506 (1985); and Thorpe et al., "The Preparation And Cytotoxic Properties Of Antibody-Toxin Conjugates", *Immunol. Rev.*, 62:119–58 (1982)).

The mutant BR96 antibody of the invention is particularly suited for use in a therapeutic conjugate because it is readily internalized within the carcinoma cells to which it binds and thus can deliver the therapeutic agent to intracellular sites of action.

Alternatively, the mutant BR96 antibody can be coupled to high-energy radiative agents, e.g., a radioisotope such as $^{131}$I; which, when localized at the tumor site, results in a killing of several cell diameters (see, e.g., Order, "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303–16 (Academic Press 1985)). According to yet another embodiment, the mutant BR96 antibody can be conjugated to a second antibody to form an antibody heteroconjugate for the treatment of tumor cells as described by Segal in U.S. Pat. No. 4,676,980.

Still other therapeutic applications for the mutant BR96 antibody of the invention include conjugation or linkage, e.g., by recombinant DNA techniques or protein chemical techniques, to an enzyme capable of converting a prodrug into a cytotoxic drug and the use of that antibody-enzyme conjugate in combination with the prodrug to convert the prodrug to a cytotoxic agent at the tumor site (see, e.g., Senter et al., "Anti-Tumor Effects Of Antibody-alkaline Phosphatase", *Proc. Natl. Acad. Sci. USA*, 85:4842–46 (1988); "Enhancement of the in vitro and in vivo Antitumor Activities of Phosphorylated Mitomycin C and Etoposide Derivatives by Monoclonal Antibody-Alkaline Phosphatase Conjugates", *Cancer Research* 49:5789–5792 (1989); and Senter, "Activation of Prodrugs by Antibody-Enzyme Conjugates: A New Approach to Cancer Therapy," *FASEB J.* 4:188–193 (1990)).

Still another therapeutic use for the mutant BR96 antibody involves use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient (see, e.g., Ramsay et al., "Bone Marrow Purging Using Monoclonal Antibodies", *J. Clin. Immunol.*, 8(2):81–88 (1988)).

In accordance with the practice of this invention, the subject of the therapy may be a human, equine, porcine, bovine, murine, canine, feline, and arian subjects. Other warm blooded animals are also included in this invention.

It is apparent therefore that the present invention encompasses pharmaceutical compositions including BR96, combinations and methods for treating human carcinomas. For example, the invention includes pharmaceutical compositions for use in the treatment of human carcinomas comprising a pharmaceutically effective amount of a mutant BR96 and a pharmaceutically acceptable carrier.

The compositions may contain the mutant BR96 antibody or antibody fragments, either unmodified, conjugated to a therapeutic agent (e.g., drug, toxin, enzyme or second antibody) or in a recombinant form (e.g., fragments of mutant BR96, bispecific mutant BR96 or single-chain immunotoxin mutant BR96). The compositions may additionally include other antibodies or conjugates for treating carcinomas (e.g., an antibody cocktail).

The antibody, antibody conjugates and immunotoxin compositions of the invention can be administered using conventional modes of administration including, but not limited to, intrathecal, intravenous, intraperitoneal, oral, intralymphatic or administration directly into the tumor. Intravenous administration is preferred.

The composition of the invention may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention may be in the range of from about 1 to about 2000 mg/m$^2$.

It has been determined that BR96 is useful as an antitumor agent (Trail et al. supra). The protocol for using BR96 in vivo is well known (Trail et al. supra). Mutant BR96 and/or functional equivalents thereof, like BR96, may be used as anti-tumor or anti-cancer agents.

The most effective mode of administration and dosage regimen for the molecules of the present invention depends upon the location of the tumor being treated, the severity and course of the cancer, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. Cancer Chemother., Rep. 50 (4): 219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided does may be administered daily or proportionally reduced depending on the specific therapeutic situation).

It would be clear that the dose of the composition of the invention required to achieve cures may be further reduced with schedule optimization.

ADVANTAGES OF THE INVENTION

Mutations in the CDRs of BR96 improved the binding affinity of mutant BR96 to its target antigen. The improved binding correlated with improved binding to the Le$^Y$ component of the tumor antigen. The higher affinity phenotype of mutant BR96 H3-36 was specifically due to the mutation of heavy chain CDR3 residue Asp101 to Ala101. Specifically, the affinity of mutant BR96 H3-36 was approximately 4.5 fold greater for Le$^Y$-HSA than the proteolytically derived chimeric BR96 Fab, and mutant BR96 H1-4-3 had 14 fold improved affinity compared to chimeric BR96 Fab.

This improved binding affinity means that some of the antibodies of the present invention bind tumor cells and tissues more tightly, thus enhancing their use in the applications described above.

In order that the invention described herein may be more fully understood, the following examples are set forth. It should be understood that these examples are for illustrative purposes only and are not to be construed as limiting the scope of this invention in any manner.

EXAMPLE 1

Mutant BR96 Having Improved Binding Affinity

Description of Cloning Method and Vector Construction: The DNA sequences encoding BR96 light chain variable (V$_L$) (SEQ ID NO:3) and heavy chain variable (V$_H$) (SEQ ID NO:1) antibody regions were cloned into the Ixsys M13 filamentous phage expression vector by hybridization mutagenesis (Near, R., 1992, *Biotechniques* 11:88–97; Glaser, S., Kristensson, K., Chilton, T., and Huse, W., 1994, Borrebaeck, C. ed., In Antibody Engineering: A Practical Guide, 2nd Edition, W. H. Freeman and Co., N.Y.).

The donor BR96 V$_L$ and V$_H$ sequences were first amplified by the polymerase chain reaction (PCR). The PCR primers contained regions of homology with specific sequences within the vector described below.

Introduction of the amplified V$_L$ and V$_H$ sequences by hybridization mutagenesis positioned the antibody sequences in frame with the regulatory elements of the M13 vector required for efficient Fab expression. The primary advantage of this technique is that restriction endonuclease sites do not need to be incorporated into the V$_L$ or V$_H$ gene sequences for cloning as is done with conventional DNA ligation methods. This eliminates the possibility of introducing amino acid residues encoded by the restriction site that could adversely affect antigen binding.

Preparation of the recipient Ixsys M13 vector: The M13 phage recipient vector was M13IXL604, an M13 bacteriophage that expresses chimeric L6 Fab (Huse, W. D., et al., 1992, *J. Immunol.* 149:3914–3920; Glaser, S. M., 1992, et al. *J. Immunol.* 149:3903–3913). The constant regions included in the vector were CH$_1$ of human IgG1 and C$_k$ of human kappa light chain. The relatively high nucleic acid homology between the BR96 and L6 gene sequences promoted efficient hybridization of BR96 sequences to the M13 vector.

The oligonucletide 5'-AGGGACTCCAGAAAGCTTTT AGGCATAAATCCA-3' (SEQ ID NO:14) was used to delete four amino acids and to introduce the stop codon TAA and a Hind III restriction site in complementarity determining region (CDR) 2 of the light chain V region of L6. This was accomplished by site-directed mutagenesis of uracil-substituted single-stranded M13IXL604 DNA as described by Kunkel (Kunkel, T. A., 1985, *Proc. Natl. Acad. Sci. U.S.A.*, 32;488–492; Kunkel, T. A., et al., 1987, *Methods Enzymol.* 154:367–382). (Also refer to Bio-Rad Muta-Gene® In Vitro Mutagenesis Kit, Version 2 manual, Bio-Rad, Richmond, Va.)

M13IXL604 phage were grown in the dut$^-$ ung$^-$ *Escherichia coli* strain CJ236 (Bio-Rad) at a multiplicity of infection (M.O.I.) of approximately 0.2. After 4–6 hours at 37° C., the bacteria were removed by centrifugation, and the phage collected by precipitation with 3.5M ammonium acetate, 20% (w/v) polyethylene glycol. Uracil-substituted single stranded (ss) DNA was then phenol extracted and ethanol precipitated.

The oligonucleotide was phosphorylated with T4 polynucleotide kinase according to the manufacturer's instructions (Boehringer Mannheim, Indianapolis, Ind.). 200 pmoles were combined with 2 µl 10× kinase buffer (1.0M Tris-HCl, pH 8.0, 100 mM MgCl$_2$, 50 mM dithiothreitol (DTT)), 1 µl 10mM ATP (Boehringer Mannheim), 1 µl T4 polynucleotide kinase (Boehringer Mannheim), and sterile water to bring the total volume to 20 µl. The reaction proceeded for 45 minutes at 37° C., and then the kinase was inactivated by heating the mixture at 65° C. for 10 minutes.

The phosphorylated oligonucleotide was annealed to the M13IXL604 vector ssDNA, followed by synthesis of the second strand. In a total volume of 10 µl, 6–8 pmoles of phosphorylated oligonucleotide were annealed to 250 ng of the vector DNA in annealing buffer (20 mM Tris-HCl, pH 7.4, 2 mM MgCl$_2$, 50 mM NaCl) in a 70° C. water bath and allowed to cool to 30° C. over 40 minutes. The reaction was placed on ice and the following added for synthesis of the second strand: 1 µl 10× synthesis buffer (10 mM ATP, 100 mM Tris-HCl, pH 7.4, 50 mM MgCl$_2$, 20 mM DTT, and 5 mM each dATP, dCTP, dGTP, and TTP), 1 μl T4 DNA ligase (Boehringer Mannheim), and 1 μl T4 DNA polymerase (Boehringer Mannheim). The reaction mixture was incubated on ice for 5 minutes, at room temperature for 5 minutes, and at 37° C. for 90 minutes.

The extended, ligated mutagenesis DNA product was electroporated into *E. coli*, strain DH10B (Gibco BRL, Gaithersburg, Md.). DH10B bacteria were made electrocompetent as follows. 500 ml L broth (LB) (1% (w/v) bacto-tryptone, 0.5% (w/v) bacto-yeast extract, 1% (w/v) NaCl) was inoculated with 1/100 volume of an overnight culture of DH10B in LB. The bacteria were grown at 37° C. with shaking until the absorbance at 600 nm was 0.5–1.0 optical density (OD). The culture flask was cooled on ice for 15–30 minutes and then the bacteria were pelleted by centrifugation at 4500×g for 15 minutes at 4° C. The supernatant was decanted and the pellet was resuspended in 500 mls cold deionized water. Bacteria were pelleted, washed in 250 mls cold deionized water, pelleted again and resuspended in 10 mls 10% (V/V) glycerol (Boehringer Mannheim) (4° C.). Centrifugation was repeated and bacteria were resuspended in 2 mls 10% (V/V) glycerol (4° C.), aliquoted into 0.1 ml volumes, and stored at −70° C.

The mutagenesis reaction mixture was diluted to 20 μl with water, and 1 μl was added to 25 μl electrocompetent DH10B. After mixing by pipetting, the mixture was transferred to a pre-chilled BioRad 0.1 cm gap cuvette. Electroporation was at 1.88 kV, 25 μF, and 200 ohms. Ten-fold aliquots, 10 μl, 1 μl, 0.1 μl, were each added to 0.2 ml of an overnight culture of *E. coli* XL-1 Blue (grown in LB plus 10 μg/ml tetracycline) (Stratagene, San Diego, Calif.), mixed with 2.5 ml top agar (0.7% (w/v) Bactoagar), and plated onto 10 cm LB plates (LB containing 1.5% (w/v) Bactoagar). The plates were incubated for 4–6 hours at 37° C.

Phage that incorporated the oligonucleotide would not express human kappa light chain and so were preliminarily identified by filter lift assay (Huse, W. D., et al., 1992, *J. Immunol.* 149:3914–3920). Fab expression was induced by overlaying each plate with a 0.45μ nitrocellulose filter (Schleicher & Schuell, Keene, N.H.) that had been soaked in 10 mM isopropyl-β-D-thiogalactopyranoside (IPTG) (Boehringer Mannheim). Plates were incubated at room temperature from 6 hr to overnight. The filters were removed and processed by immunoblotting techniques. For all steps the filters were constantly agitated on a rocking platform. First, the filters were blocked in blocking buffer (Biosite, San Diego, Calif.) to prevent nonspecific binding of antibodies. The filters were then incubated 1–2 hr at room temperature with goat anti-human kappa light chain conjugated to alkaline phosphatase (Fisher Biotech, San Francisco, Calif.) diluted 1:1000 in blocking buffer. The filters were washed three times for ten minutes with TBST (25 mM Tris-HCl, pH 7.4, 0.137M NaCl, 5 mM KCl, 0.9 mM CaCl$_2$, 0.5 mM MgCl$_2$, 0.05% (V/V) Tween 20®) and then developed with alkaline phosphatase substrate reagent (Bio-Rad).

Plaques that did not stain with the anti-human kappa reagent were isolated, and phage ssDNA prepared for sequencing (Sambrook, J, Fritsch, E. F., Maniatis, T., 1989, *Molecular Cloning, A Laboratory Manual*, Cold Spring Harbor Laboratory Press). Sequence analysis, performed with Sequenase Version 2 according to the manufacturer (United States Biochemical, Cleveland, Ohio) confirmed that the oligonucleotide sequence had been incorporated into the vector DNA.

Similarly, the oligonucleotide 5'-GAAGTCATCAGCAC GCGTTTAAGTGTAGGTGTT-3' (SEQ ID NO:15) was used to delete three amino acids and to introduce the stop codon TAA and a Mlu I restriction site in CDR2 of the heavy chain V region of L6. The vector DNA from the phage described above that had incorporated the stop in the CDR 2 of the light chain was used as the template for the mutagenesis. The phenotypic difference between phage that incorporated the mutation versus parent was that introduction of a stop in CDR2 would prevent the expression of a decapeptide, Tyr Pro Tyr Asp Val Pro Asp Tyr Ala Ser (SEQ ID NO:13), (Huse, W. D., et al., 1989, *Science* 246:1275–1281) appended to the carboxy terminus of the vector CH$_1$ domain. Nitrocellulose lifts of phage from the mutagenesis reaction were probed with 7F11-alkaline phosphatase conjugate, a murine monoclonal antibody that binds the decapeptide (Biosite, Inc., San Diego, Calif.), and phage were isolated that did not bind 7F11. Sequence analysis confirmed the presence of the mutagenic oligonucleotide sequence.

Oligonucleotides Used for Amplification of BR96 Sequences: All oligonucleotides were synthesized by β-cyanoethyl phosphoramidite chemistry on a MilliGen Cyclone Plus DNA synthesizer (Burlington, Mass.).

Oligonucleotides were purified using oligonucleotide purification cartridges (Applied Biosystems, Foster City, Calif.). The 5' sense or forward PCR primer consisted of DNA sequences identical to the 3' end of the leader peptide sequence contained in the M13 expression vector immediately followed by the amino-terminal sequence of the BR96 V region genes to be cloned.

The sequence of the BR96 light chain forward PCR primer was 5'-GCCCAACCAGCCATGGCCGATGTTTT GATGACCCAAAT-3' (SEQ ID NO:16). The underlined region represents the six codons plus the first two nucleotides coding for the amino-terminal 7 amino acids of BR96 V$_L$ gene sequence. The remainder of the primer hybridized to the 3' end of the leader peptide sequence contained in the M13 expression vector. The 3' anti-sense or reverse PCR primer consisted of DNA sequences identical to the 5' end of the human kappa light chain constant domain contained in the M13 expression vector immediately preceded by sequences that hybridized to the carboxy-terminal sequences of the V region gene.

The sequence of BR96 light chain reverse PCR primer was 5'-AGATGGCGGGAAGATGAAGACAGATGGTGC AGCCACAGTCCGTTTTATTTCCAA-3' (SEQ ID NO:17). (The original light chain reverse PCR primer had a point mutation in codon 112. This was corrected subsequent to the cloning of BR96 into the M13IX vector. The oligonucleotide used to correct the mutation was 5'-GACAGATGGTGCAGCCACAGTCCG-3' (SEQ ID NO:18).)

The underlined region represents the 5 codons coding for carboxy-terminal residues 104–108 of BR96 V$_L$. This sequence annealed to, and amplified the sense 3' BR96 V$_L$ gene sequence. The amplified PCR product hybridized to the 3' end of the bacterial pectate lyase (pel B) leader peptide sequence, which directs V$_L$-C$_k$ (Better, M., et al., 1988, *Science* 240:1041–1045) to the bacterial periplasmic space, and to codons 109–116 of the light chain constant sequence contained in the M13 expression vector.

Similarly, the BR96 heavy chain forward PCR primer sequence was 5'-CCTGTGGCAAAAGCCGAAGTGAAT CTGGTGGAG-3' (SEQ ID NO:19) and the BR96 heavy chain reverse PCR primer sequence was 5'-ATGGGCCCTTGGTGGAGGCTACAGAGACCGTGA CCAG-3' (SEQ ID NO:20). The heavy chain PCR amplified sequences hybridized to the 3' end of the bacterial alkaline phosphatase leader peptide sequence, which directs secretion of $V_H$-$CH_1$ (Skerra, A. and Plückthun, A., Science 240:1038–1041) to the bacterial periplasmic space, and to codons 114–119 of the heavy chain $CH_1$ sequence contained in the M13 expression vector.

Cloning of BR96 Sequences into the M13IX Vector: The BR96 $V_L$ and $V_H$ genes were sequentially transferred into the Ixsys M13IXL604 expression vector by hybridization mutagenesis. For PCR amplification of the variable region genes, pUC19 plasmids containing either the BR96 $V_L$ or $V_H$ gene sequence were digested to completion with restriction endonuclease Xho I. The DNAs were extracted once with an equal volume of phenol/chloroform/isoamyl alcohol (25:24:1), once with an equal volume of chloroform/isoamyl alcohol (24:1), and then were precipitated with ethanol. The restricted DNAs were resuspended with sterile water to a concentration of 2 ng/µl. 10 ng of linearized pUC19/BR96 $V_L$ plasmid was amplified in a 50 µl reaction volume using the light chain forward and reverse PCR primers described above. PCR amplification was performed by the method of Saiki et al. (1988, Science 239:487–491). Conditions for amplification were denaturation at 94° C. for 2 min, then two cycles of denaturation at 94° C. for 1 min, annealing at 50° C. for 1 min, and DNA synthesis at 72° C. for 1 min. This was followed by denaturation at 94° C. for 1 min, annealing at 55° C. for 1 min, and DNA synthesis at 72° C. for 1 min for 40 cycles, and finally, extension at 72° C. for 10 min. The amplified product was extracted once with an equal volume of chloroform/isoamyl alcohol (24:1) and ethanol precipitated. PCR amplification of the $V_H$ sequence was performed similarly with linearized pUC19/BR96 $V_H$ plasmid and the appropriate primers described above. The amplified $V_H$ and $V_L$ double-stranded DNA products were isolated by gel electrophoresis. The DNA product was applied to a 5% (w/v) polyacrylamide/1X Tris borate, pH 8.3-EDTA gel, and electrophoresed at 100 V. The gel was stained with ethidium bromide (1 µg/ml), and DNA was visualized with a UV light and excised with a razor blade. The DNA was chemically eluted from the gel with gel elution buffer (0.3M NaCl, 10 mM Tris-HCl, pH 7.5, 1 mM EDTA, 0.1% [w/v] SDS) overnight with shaking at 37° C. The eluate was collected, and 0.25 ml gel elution buffer was added to the gel slice and incubated for an additional 30–60 minutes at 37° C. with shaking. The second eluate was pooled with the first, and both were extracted three times with butanol, once with chloroform:isoamyl alcohol (24:1), and then ethanol precipitated.

The DNA was collected by centrifugation for 20 minutes at 10,000×g; the pellet was washed once with 80% (v/v) ethanol and then air dried. The DNA was solubilized in approximately 15 µl of water and the concentration was determined by measuring the absorbance at 260 nm of 3–4 µl of the sample.

Hybridization mutagenesis was performed essentially as described above. The double-stranded (ds) PCR product was phosphorylated with T4 polynucleotide kinase by combining 400 ng dsDNA with 2 µl 10× kinase buffer, 1 µl 10 mM ATP, 1µl T4 polynucleotide kinase, and sterile water to bring the total volume to 20 µl. The reaction proceeded for 45 at 37° C. The kinase was inactivated by heating the mixture at 65° C. for 10 minutes.

The phosphorylated PCR amplified BR96 $V_L$ DNA was annealed to the modified uridinylated M13IXL604 ss DNA vector, followed by synthesis of the second strand. In a total volume of 10 µl, 100 ng of phosphorylated BR96 $V_L$ DNA was annealed to 250 ng of the vector DNA in annealing buffer at 90° C. for 3 min, and then cooled slowly to 30° C. The reaction was placed on ice and second strand synthesis proceeded as described above.

The extended, ligated mutagenesis DNA product was electroporated into E. coli, strain DH10B. Successful replacement of the modified L6 light chain with the donor BR96 light chain was detected by plaque lift assay with goat anti-human kappa light chain conjugated to alkaline phosphatase. Clone M13IX BR96$V_L$-2 had the correct, in frame chimeric immunoglobulin sequence as determined by DNA sequence analysis.

Uridinylated M13IX BR96$V_L$-2 single-stranded DNA template was prepared and mutagenized with phosphorylated PCR amplified BR96$V_H$. Replacement of L6 heavy chain sequence with the donor BR96 $V_H$ region resulted in the expression of the decapeptide appended to the carboxy terminus of the vector $CH_1$ domain and was detected in a plaque lift assay with 7F11-alkaline phosphatase conjugate. Alternatively, 757-4-1, a murine anti-idiotype monoclonal antibody that binds BR96, was used to detect the successful introduction and expression of BR96 $V_H$ sequences. After the nitrocellulose filter was blocked, 757-4-1 (1 µg/ml in blocking buffer) was added for 1–2 hours at room temperature. The filter was washed three times, 10 minutes each with TBST, and then probed with goat anti-mouse IgG (Fisher Biotech). Filters were again washed and developed in alkaline phosphatase substrate as described above.

Clone M13IX BR96 13.2 was identified in a filter lift assay with anti-idiotype 757-4-1 and had in frame, full length chimeric immunoglobulin sequence. A single point mutation was found at position 51, which converted the Ile to a Val. This point mutation was converted back to Ile using the oligonucleotide 5'-ACCTTGACTAATGTATGCGACC-3' (SEQ ID NO:21) to construct M13IX BR96 13.24.

M13IX BR96 13.24 was expressed in E. coli and crude Fab preparations were isolated from the periplasmic space as described (Huse, W. D., et al., 1992, J. Immunol. 149:3914–3920). Briefly, log phase E. coli strain MK-30-3 (Boerhinger Mannheim) were infected with 1–5 M.O.I. and grown for 1–3 hours at 37° C. in an incubator shaker. The cultures were induced for Fab expression by adding 0.5 mM IPTG and continued to incubate at 25° C. overnight. The bacteria were harvested by centrifugation (4500×g) and resuspended in approximately one-tenth the culture volume TES buffer (30 mM Tris-HCl, pH 8.0, 2 mM EDTA, 20% [w/v] sucrose). An equal volume of 2 mg/ml lysozyme in TES was added to the suspension and incubated on ice for 10 minutes to permeabilize the cells. The suspension was then centrifuged (13,500×g) and the supernatant, the periplasmic fraction, was removed and stored at 4° C.

The BR96 13.24 Fab preparation was assayed by ELISA for binding to the breast adenocarcinoma tumor cell line H3396 (Hellstrom, I., et al., 1990, Cancer Research, 50:2183–2190). H3396 cells were seeded into a 96 well tissue culture plate and grown overnight at 37° C. in IMDM (Gibco, Grand Island, N.Y.) containing 10% fetal calf serum. Media was flicked out of the plate, and the cells were fixed with 2% paraformaldehyde/phosphate buffered saline (PBS) for 15 min. The fixed cells were washed 3 times with PBS, 1% (w/v) BSA and blocked in PBS, 1% BSA for 1 hr. 50 µl of periplasm was diluted with 75 µl Tris buffered saline, pH 7.5 (TBS), 1% BSA. 50 µl of the diluted periplasm was incubated with the H3396 cells for 1 hr at room temperature. The cells were washed 4–5 times with TBS, 1% BSA and 100 µl of goat anti-human kappa alkaline phosphatase conjugate (1:1000 dilution in TBS, 1% BSA) was added per well for 30 min at room temperature. The cells were washed 5 times with TBS and developed with 6 mg/ml phenolphthalein monophosphate in 0.1M aminomethylpropanediol, 0.5M Tris-HCl, pH 10.2, 0.1% (w/v) NaN$_3$ (JBL Scientific, San Luis Obispo, Calif.). The reaction was terminated by bringing it to a final concentration of 10 mM Tris base, 5 mM EDTA. BR96 specifically bound the tumor cell line H3396.

Construction of Codon-Based Mutagenized BR96 Libraries: The residues within the CDR loops of the V$_H$ and V$_L$ domains to mutagenize by codon-based mutagenesis techniques were determined by computer modeling based upon canonical structures (Chothia, C. et al., *J. Mol. Biol.*, 186:651–663 [1985] and Chothia, C. et al., *Nature*, 342:877–883 [1989]) (J. Bajorath, BMSPRI). The following recommendations were made:

V$_L$ CDR 1 residues Val30-Tyr37
V$_L$ CDR 2 residues Tyr54-Ser57
V$_L$ CDR 3 residues Gly96-Phe101
V$_H$ CDR 1 residues Gly26-Tyr33
V$_H$ CDR 2 residues Ser52-Asp59
V$_H$ CDR 3 residues Gly99-Trp105.

Six codon-based mutagenesis libraries were constructed in BR96, each library containing a different mutagenized CDR. Six templates were prepared by introducing a deletion followed by a stop codon TAA in the CDR of BR96. The oligonucleotides that introduced the deletion and stop are shown below. The stop codon is indicated by the underlined sequence.

Light chain oligonucleotides used to introduce deletion/stop:

templates and BR96 heavy chain was not expressed in the three heavy chain templates. Reconstitution of the nonfunctional CDR by codon-based mutagenesis will rescue the ability to detect immunoglobulin chain expression by immunochemical techniques. Sequence of all constructs was confirmed by DNA sequence analysis. Uridinylated single-stranded DNA templates were then prepared for codon-based mutagenesis.

Codon-based oligonucleotides were synthesized with a 50% bias for parent BR96 CDR sequence as described (Glaser, S. M., et al., 1992, *J. Immunol.* 149:3903–3913). The oligonucleotide sequences are shown below. Following the final synthesis step the contents from the parent column (P) and the mutagenic column (M) were pooled and all six mixtures purified by electrophoresis on a denaturing 12% polyacrylamide/7M urea/IX Tris borate-EDTA gel. The DNAs were chemically eluted from the excised gel slices with gel elution buffer, extracted three times with butanol and ethanol precipitated. 2 μg of purified oligonucleotide from each of the six syntheses was phosphorylated and 100 ng of each was subsequently used to generate six BR96 CDR libraries by site-directed mutagenesis (see procedures above).

The following codon-based oligonucleotides were synthesized for mutagenizing V$_H$ and V$_L$ CDRs of BR96. All oligonucleotides are represented in the antisense form, wherein N represents equally A, G, C, and T. A/C indicates 50% of A and 50% of C.

Light chain oligonucleotides:

---

ΔCDR 1 V$_L$:

5'-GTACCATTCTAAAAGCTTTTAAATGATCTGACT-3' (SEQ ID NO: 22)

ΔCDR 2 V$_L$:

5'-AGAAAATCGGTTAAGCTTTTAGATCAGGAGCTG-3' (SEQ ID NO: 23)

ΔCDR 3 V$_L$:

5'-CGAGCCGAACGTAAGCTTTTATTGAAAGCAGTA-3' (SEQ ID NO: 24)

Heavy chain oligonucleotides used to introduce deletion/stop:

ΔCDR 1 V$_H$:

5'-AACCCAATACATACGCGTTTAAGAGGTTACACA-3' (SEQ ID NO: 25)

ΔCDR 2 V$_H$:

5'-AGTGTCTGGATAACGCGTTTAAATGTATGCGAC-3' (SEQ ID NO: 26)

ΔCDR 3 V$_H$:

5'-CCAGTAAGCAAAACGCGTTTATCTTGCACAGTA-3' (SEQ ID NO: 27)

---

The six BR96 CDR deletion/stop templates were constructed by site-directed mutagenesis and identified by loss of reactivity with immunochemical staining reagents. BR96 light chain was no longer expressed in the three light chain

---

BR96 L1P: 5'-GTA CCA TTC TAA ATA GGT GTT GCC ATT ATT ATG TAC AAT GAT CTG ACT-3' (SEQ ID NO: 28)
BR96 L1M: 5'-GTA CCA TTC TAA A/CNN A/CNN A/CNN A/CNN A/CNN A/CNN A/CNN A/CNN AAT GAT CTG ACT-3' (SEQ ID NO: 29)
BR96 L2P: 5'-AGA AAA TCG GTT GGA AAC TTT GTA GAT CAG GAG CTG-3' (SEQ ID NO: 30)
BR96 L2M: 5'-AGA AAA TCG GTT A/CNN A/CNN A/CNN A/CNN GAT CAG GAG CTG-3' (SEQ ID NO: 31)
BR96 L3P: 5'-CGA GCC GAA CGT GAA TGG AAC ATG TGA ACC TTG AAA GCA GTA-3' (SEQ ID NO: 32)
BR96 L3M: 5'-CGA GCC GAA CGT A/CNN A/CNN A/CNN A/CNN A/CNN A/CNN TTG AAA GCA GTA-3' (SEQ ID NO: 33)

Heavy chain oligonucleotides:

BR96 H1P: 5'-AAC CCA ATA CAT GTA ATA GTC ACT GAA AGT GAA TCC AGA GGT TAC ACA-3' (SEQ ID NO: 34)
BR96 H1M: 5'-AAC CCA ATA CAT GTA ATA GTC A/CNN A/CNN A/CNN A/CNN A/CNN A/CNN A/CNN A/CNN AGA GGT TAC ACA-3' (SEQ ID NO: 35)
BR96 H2P: 5'-AGT GTC TGG ATA GTC GGT TAT ATC ACC ACC TTG ACT AAT GTA TGC GAC-3' (SEQ ID NO: 36)
BR96 H2M: 5'-AGT GTC TGG ATA A/CNN A/CNN A/CNN A/CNN A/CNN A/CNN A/CNN AAT GTA TGC GAC-3' (SEQ ID NO: 37)
BR96 H3P: 5'-CCA GTA AGC AAA CCA GGC CCC GTC GTC CAG GCC TCT TGC ACA GTA-3' (SEQ ID NO: 38)
BR96 H3M: 5'-CCA GTA AGC AAA A/CNN A/CNN A/CNN A/CNN A/CNN A/CNN A/CNN TCT TGC ACA GTA-3' (SEQ ID NO: 39)

Screening of BR96 CDR Libraries for Higher Affinity Fabs: BR96 CDR libraries were screened for higher affinity variant Fabs by ELISA assay on paraformaldehyde fixed H3396 cells. As an example, BR96 CDR3 heavy chain library constructed with oligonucleotides BR96 H3P and BR96 H3M was analyzed by plaque lift assays and decapeptide positive clones were isolated. Periplasmic fractions were prepared from each clone and were assayed on fixed H3396 cells as described above. From an initial screen of 72 BR96 $V_H$ CDR3 variant Fabs, one clone, H3-36, bound H3396 tumor cells giving a higher OD signal than the parent BR96 molecule at the same concentration, suggesting that H3-36 had a greater affinity for antigen. BR96 H3-36 did not bind to fixed H3719 cells, a colon carcinoma cell line that does not express the BR96 antigen. This indicated that the improved binding of clone BR96 H3-36 to antigen was specific.

DNA sequence analysis of BR96 H3-36 revealed a single amino acid change in CDR3 of the heavy chain from Asp101 (GAC) to Ala101 (GCG) (sequential numbering system). The oligonucleotide 5'-CCA GGC CCC GTC CGC CAG GCC TCT TGC-3' (SEQ ID NO:40) was synthesized and used to change the Asp101 residue in the parent BR96 template to Ala101 by site directed mutagenesis and therefore was designated BR96 A101. After the correct DNA sequence of this clone, BR96 A101 (i.e., mutant BR96 comprising alanine at position 101 of CDR3 of the heavy chain), was confirmed, binding to paraformaldeyde fixed H3396 cells was evaluated. BR96 A101 bound H3396 tumor cells similarly to BR96 H3-36 demonstrating that the higher affinity phenotype of BR96 H3-36 was specifically due to the mutation of heavy chain CDR3 residue Asp101 to Ala101.

Analysis of BR96 H3-36 Fab by ELISA: BR96 binds to the Lewis Y ($Le^Y$) moiety of a tumor antigen expressed on many carcinomas and carcinoma derived cell lines (Hellstrom I., et al., 1990, Cancer Res. 50:2183–2190). To show that the improved binding of BR96 H3-36 to tumor cells correlated with improved binding to the $Le^Y$ component of the tumor antigen, an ELISA using $Le^Y$ tetrasaccharide conjugated to human serum albumin ($Le^Y$-HSA) (Alberta Research Council, Edmonton, Alberta, Canada) was performed. Another antigen source for ELISAs was a membrane preparation of H3396 cells. The procedure for isolation of membranes is as follows. Cells were grown to confluency in IMDM, 10% (v/v) fetal calf serum and treated with EDTA solution (0.02% [w/v] EDTA and 0.02% [w/v] dextrose in PBS) at 37° C. for 5–10 minutes to detach the cells from the culture flask. Cells were collected by centrifugation (1000×g) and washed once with PBS (4° C.). The supernatant was aspirated and cell pellets worked with immediately or frozen at −70° C. When 0.5–3 ml of cell pellet was collected, cells were processed for membrane isolation. If frozen, pellets were thawed at room temperature. 10 ml lysis buffer (10 mM Tris-HCl, pH 7.4, 5 mM EDTA, pH 10.2, 10.5 µg/ml aprotinin, 0.5 mM PMSF, 5 µg/ml leupeptin) (4° C.) was added to the pellet, mixed well with a pipette, and incubated on ice for 15 minutes. The suspension was then homogenized in a chilled Dounce homogenizer with 30–40 strokes, and the homogenate was centrifuged 1500×g for 5–10 minutes, 4° C. The supernatant was carefully removed and placed in a 12 ml ultraclear centrifuge tube (Beckman, Fullerton, Calif.), and the membranes were pelleted by high speed centrifugation (82,000× g, 4° C.). A lipid layer at the top of the tube was carefully removed with a Pasteur pipette and the rest of the supernatant decanted. The pellet was resuspended in PBS Buffer (PBS containing 5 mM EDTA, pH 10.2, 10.5 µg/ml aprotinin, 0.5 mM PMSF, 5 µg/ml leupeptin, 25 mM iodoacetemide) and centrifuged at high speed as above. The pellet was resuspended in 1–3 ml PBS Buffer and protein content was estimated by the BCA protein assay (Pierce Chemical Company, Rockford, Ill.).

The source of H3-36 Fab was either a periplasmic fraction or purified Fab. H3-36 Fab was purified from a periplasmic preparation derived from 4 liters of culture. The periplasmic fraction was diluted with an equal volume of PB-0.5M NaCl (PBS supplemented with NaCl to bring its concentration to 0.5M) and then filtered through a 0.45 µm filter. The diluted filtered fraction was applied to an affinity column, goat anti-human Fab antisera (Sigma, St. Louis, Mo.) coupled to CNBr-activated Sepharose 4B (Pharmacia, Piscataway, N.J.) according to manufacturer's instructions. After washing the column with PB-0.5 M NaCl, the H3-36 Fab was eluted with 0.1M citric acid, pH 2.2 containing 0.1M NaCl. Elution of the Fab was monitored by $A_{280}$ and immediately upon elution, the Fab fraction was neutralized with the addition of one-tenth volume 1M Tris-HCl, pH 8.5. After buffer exchange by dialysis against PBS, H3-36 Fab was concentrated in an Amicon stir cell with a YM-10 filter (Amicon Division, W. R. Grace & Co., Beverly, Mass.).

For the ELISA 96-well microtiter plates (Immunlon II, Dynatech Laboratories, Chantilly, Va.) were coated with $Le^Y$-HSA (100 µl per well of 1 µg/ml in 0.05M carbonate/bicarbonate, pH 9.6). Plates were incubated overnight at 4° C. Unabsorbed antigen was flicked out of the plates, and the wells were washed three times with saline-Tween (0.9% [w/v] NaCl, 0.5% [v/v] Tween 20®). Nonspecific binding of antibodies was blocked by the addition of 200 µl/well of specimen diluent (10% [v/v] Specimen Diluent, Genetic Systems, Seattle, Wash.) for one hour at room temperature. Excess blocking buffer was expelled and the plate washed once with saline-Tween.

H3-36 Fab was compared to the proteolytically derived chimeric BR96 Fab. Chimeric BR96 (Fell, H. P., Yarnold, S., Hellstrom, I., Hellstrom, K. E., Folger, K. R., 1989, *Proc. Natl. Acad. Sci. U.S.A.*, 86:8507-8511; Yarnold, S. and Fell, H. P. 1994 Cancer Research 54:506-512) was digested with papain as outlined in the manufacturer's literature (Pierce Chemical Company). The H336 Fab and chimeric BR96 Fab were titrated in serial three-fold dilutions in specimen diluent and incubated on $Le^Y$-HSA and H3396 membranes overnight at 4° C. The plates were washed four times with saline-Tween, and a horseradish peroxidase (HRP) conjugated goat anti-human kappa light chain specific reagent (Caltag, South San Francisco, Calif.) diluted according to previously performed titrations in conjugate diluent (Genetic Systems) (100 µl per well) was added.

The reactions incubated at room temperature for one hour, and then the conjugate was flicked out of the wells and the plates washed five times with saline-Tween. Chromogen, TMB (3,3',5,5' tetramethylbenzidine) (Genetic Systems), was diluted 1:100 in buffered substrate (0.1M sodium acetate adjusted to pH 5.5 with 0.1M citric acid containing 0.015% [v/v] $H_2O_2$) and added to the 96 well plate (100 µl per well) for 20-30 minutes at room temperature. The reactions were terminated with the addition of 100 µl per well of 3 N $H_2SO_4$, and the absorbance at 450 nm measured with a Biotek EL 312 microplate reader (Burlington, Vt.).

Figure 7:
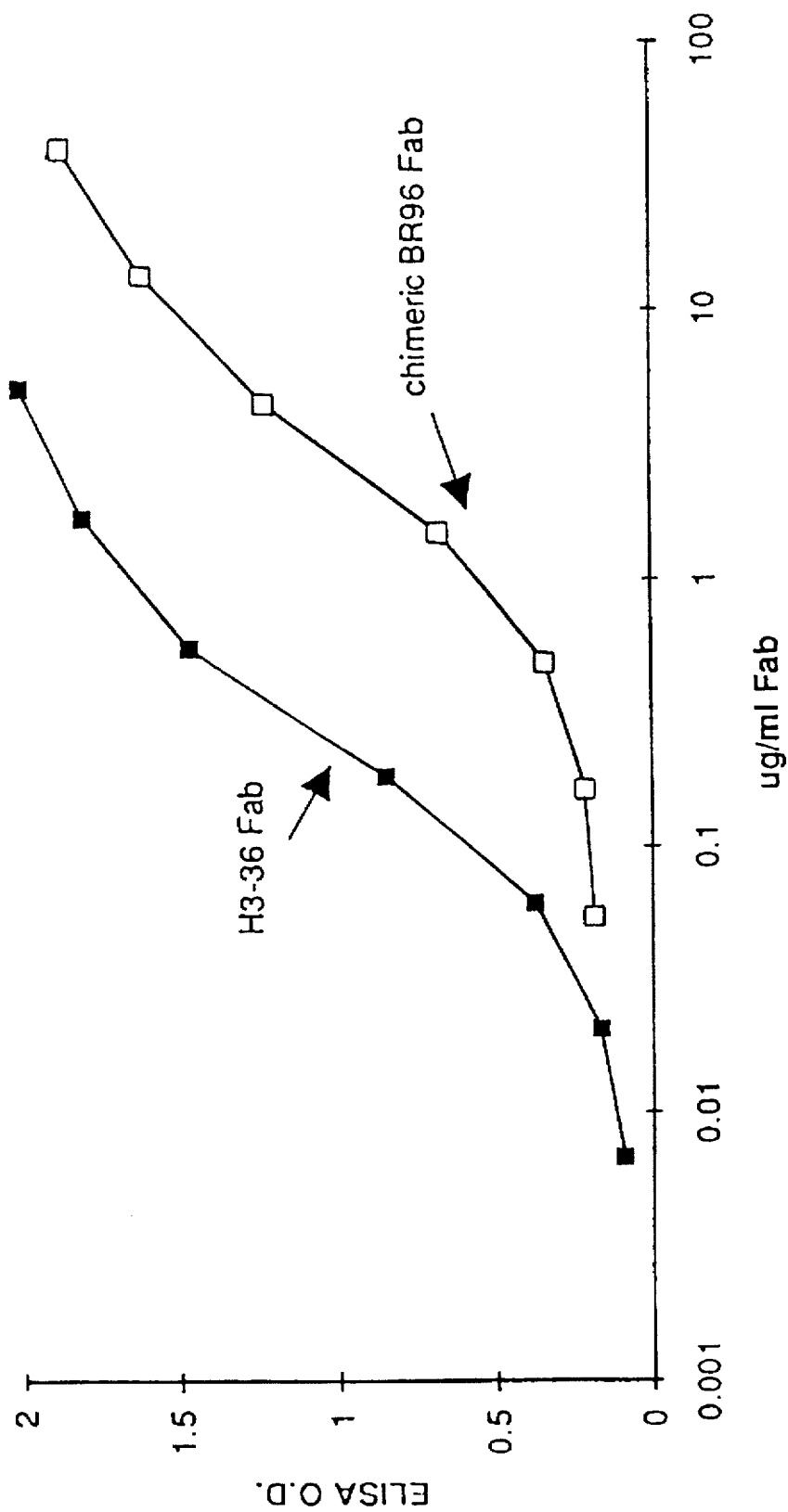
FIG. 7 is a line graph showing the results of an ELISA assay wherein the mutant BR96 H3-36 Fab binds to H3396 membranes with increased affinity compared to ChiBR96 Fab.
Figure 8:
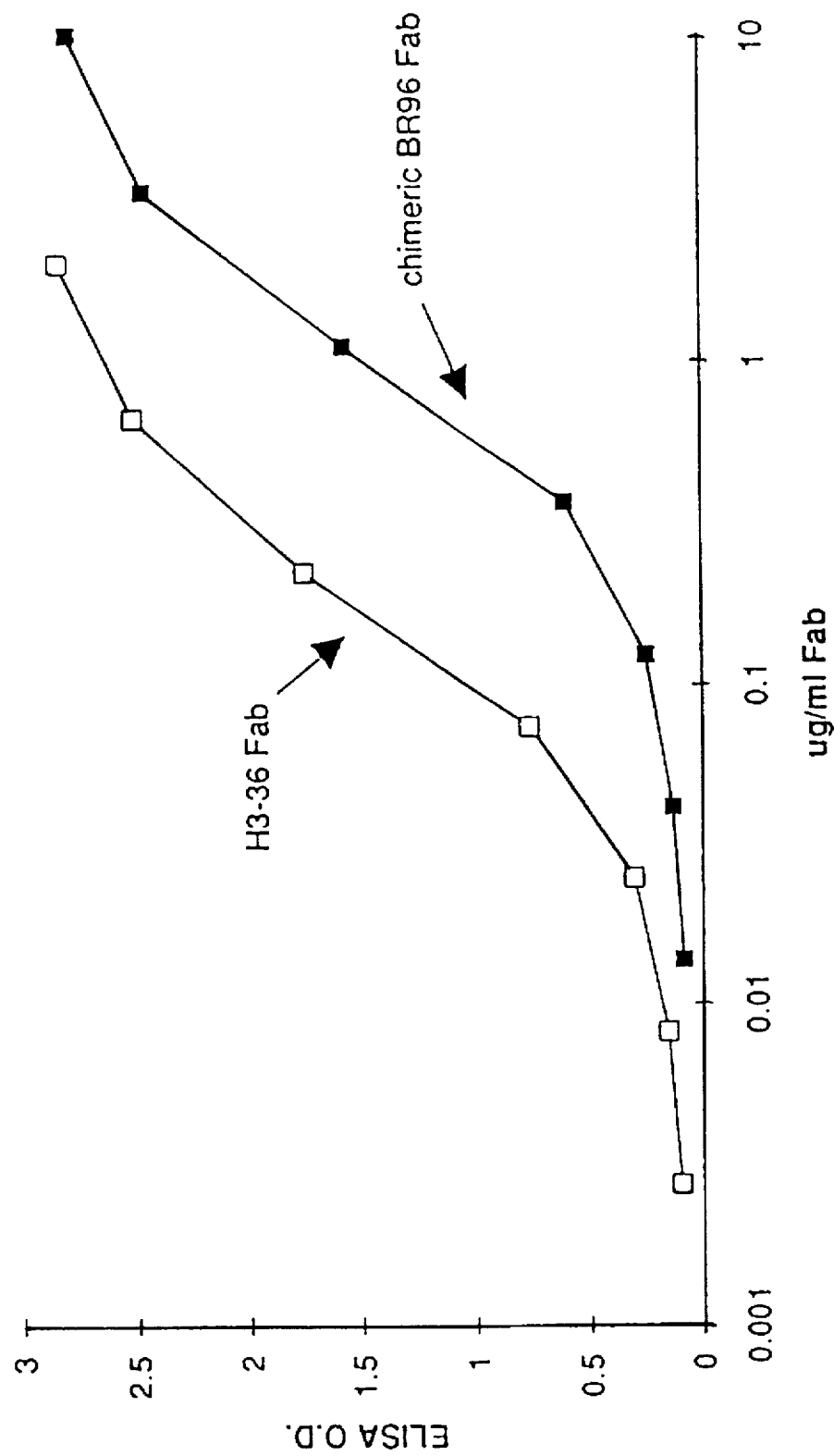
FIG. 8 is a line graph showing the results of an ELISA assay wherein mutant BR96 H3-36 Fab binds to $Le^Y$-HSA with increased affinity compared to ChiBR96 Fab.

The binding profiles of H3-36 Fab to H3396 membranes and $Le^Y$-HSA was similar (FIGS. 7 and 8). In comparison to proteolytically derived chimeric BR96 Fab, approximately five-fold less mutant BR96 H3-36 Fab was required to give one-half maximal OD. This data confirmed that the mutation in H3-36 increased the binding affinity of the Fab for its antigen.

Screening of BR96 CDR3 Libraries with $Le^Y$-Horseradish Peroxidase: Contribution of the Asp101 to Ala101 mutation to increased binding of H3-36 to antigen was examined by an independent method. $Le^Y$-horseradish peroxidase conjugate ($Le^Y$-HRP) was used in filter lift assays to screen BR96 codon-based mutagenized CDR libraries. $Le^Y$-hydrazide (Alberta Research Council) was derivatized with HRP as follows. 10 mg HRP (Boerhinger Mannheim) was solubilized in 0.5 ml 0.1M acetate buffer, pH 5.0 (4° C.). 25.7 µl of 0.5M sodium periodate was added to the HRP solution and incubated 20 minutes in an ice bath protected from light. Oxidized HRP was separated from unconsumed sodium periodate by Sephadex G25 gel filtration. The oxidized HRP was added to 3 mg $Le^Y$-hydrazide and kept at 4° C. in the dark for four hours and mixed occasionally. The reaction was neutralized with the addition of 2.86 µl of a 136.8 mg/ml solution of sodium cyanogen borohydride. The solution was kept at 4° C. overnight in the dark and was then dialyzed against PBS. The HRP concentration was determined by diluting an aliquot 1:20, measuring the absorbance at 403 nm, and calculating the concentration using an extinction coefficient of 0.73. Thimerosol (0.01% [w/v)]) was added as a preservative to $Le^Y$-HRP and it was stored at 4° C.

Filter lifts from the BR96 CDR3 heavy chain library were prepared as described above and blocked with Blotto-Tween (PBS containing 0.5% [w/v] Carnation non-fat dry milk, 0.01% [v/v] antifoam-A, 0.01% [v/v] thimerosol, 0.2% [v/v] Tween 20®). The nitrocellulose lifts were probed with 2 µg/ml $Le^Y$-HRP in Blotto-Tween overnight at 4° C. The filters were washed 5 times at room temperature for 5 min in PBS, 0.1% (v/v) Tween 20®, and then were developed with Enhanced Chemiluminescence Reagent™ (Amersham Life Sciences, Arlington Heights, Ill.).

From the BR96 CDR3 heavy chain library screen a single clone, BR96 H3-1, produced a stronger signal than the parent BR96. This clone was plaque purified, and a periplasmic fraction prepared and assayed by ELISA for binding to paraformaldehyde fixed H3396 tumor cells. The plaque-purified BR96 variant, called BR96 H3-1-1, bound fixed H3396 cells as well as BR96 H3-36. The DNA sequence of BR96 H3-1-1 compared to the parent BR96 and BR96 H3-36 is shown below:

| $V_H$ CDR3 amino acid position | 99 | 100 | 101 | 102 | 103 | 104 | 105 | |
|---|---|---|---|---|---|---|---|---|
| BR96 | GGC | CTG | GAC | GAC | GGG | CCC | TGG | (residues 295–315 of SEQ ID NO: 1) |
|  | Gly | Leu | Asp | Asp | Gly | Ala | Trp | (SEQ ID NO: 55) |
| BR96 H3-36 | GGC | CTG | GCG | GAC | GGG | GCC | TGG | (SEQ ID NO: 56) |
|  | Gly | Leu | Ala | Asp | Gly | Ala | Trp | (SEQ ID NO: 53) |
| BR96 H3-1-1 | Gly | Leu | Ala | Asp | Gly | Ala | Trp | (SEQ ID NO: 53) |

DNA sequence analysis revealed that the higher affinity BR96 variant BR96 H3-1-1 had the identical amino acid sequence as BR96 H3-36, which was selected by its binding to H3396 tumor cells, again demonstrating that the BR96 H3-36 higher affinity phenotype resulted from a stronger interaction with the $Le^Y$ antigen expressed on H3396 cells. The sequence identity also suggested that alanine in position 101 of CDR3 is critical to conferring the higher affinity phenotype. Finally, sequencing also showed that BR96 H3-1-1 was selected from the BR96 CDR3 heavy chain library and was not mutant BR96 H3-36, since Ala104 in BR96 H3-1-1 was coded by GCG rather than GCC found in the parent BR96 and in BR96 H3-36.

Construction of Codon-Based Mutagenesis BR96 H3-36 Libraries: BR96 H3-36 was used as template for codon-based mutagenesis in an attempt to further enhance the affinity of BR96 H3-36 to $Le^Y$ antigen. Uridinylated BR96 ΔCDR 1 $V_H$ template was mutagenized with the oligonucleotide encoding the CDR3 Ala101 mutation, and a clone containing the Ala101 mutation in CDR3 of VH was isolated. Uridinylated template was prepared and a codon-based library constructed in heavy chain CDR1 using the BR96 H1P and BR96 H1M codon-based oligonucleotides as described above.

This library was screened by lift assay with $Le^Y$-HRP as previously described, and one clone, H1-4-3, was identified as potentially having higher affinity to antigen than BR96 H3-36. DNA sequencing of the clone revealed three amino acid changes in CDR1, which are described below.

| $V_H$ CDR3 amino acid position | 26 | 27 | 28 | 29 | 30 | 31 | 32 | |
|---|---|---|---|---|---|---|---|---|
| BR96 | GGA | TTC | ACT | TTC | AGT | GAC | TAT | (residues 76–96 of SEQ ID NO: 1) |
| | Gly | Phe | Thr | Phe | Ser | Asp | Tyr | (residues 26–32 of SEQ ID NO: 2) |
| BR96 H1-4-3 | GGA | TTC | CCG | TTC | GCG | TCG | TAT | (SEQ ID NO: 57) |
| | Gly | Phe | Pro | Phe | Ala | Ser | Tyr | (residues 1–7 of SEQ ID NO: 50) |

Figure 9:
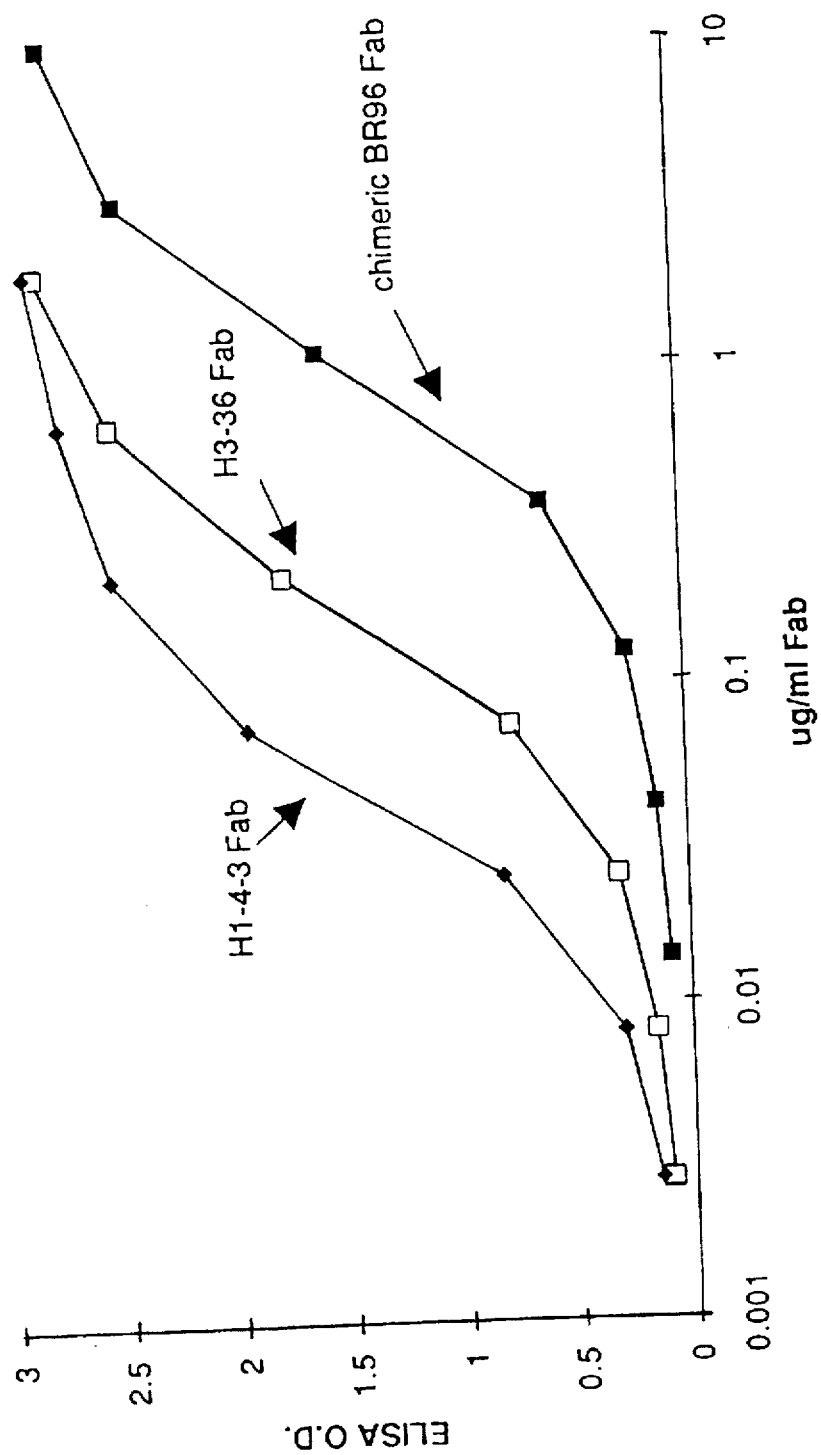
FIG. 9 is a line graph showing the results of an ELISA assay wherein mutant BR96 H3-36 Fab and mutant BR96 H1-4-3 Fab binds to $Le^Y$-HSA with increased affinity compared to ChiBR96 Fab.

BR96 H1-4-3 Fab was isolated by affinity chromatography (see method above) and analyzed by ELISA to confirm the observation in the lift assay that it had increased affinity compared to BR96 H3-36. Binding of purified BR96 H1-4-3 Fab and purified BR96 H3-36 Fab to Le$^Y$-HSA was compared to proteolytically derived chimeric BR96 Fab. Results showed that BR96 H1-4-3 Fab had approximately a fourfold improvement in binding to Le$^Y$-HSA compared to BR96 H3-36 Fab, and approached a fifteen-fold improvement compared to the parent BR96 Fab (FIG. 9).

The affinities of parent BR96 Fab, BR96 H3-36 Fab, and BR96 H1-4-3 Fab were quantified by surface plasmon resonance (BIAcore, Biosensor, Piscataway, N.J.). Experiments were performed as described by E. Wolff, et al., (1993, *Cancer Res.*, 53:2560–2565) with the following modifications. Le$^Y$-HSA was anchored to a derivitized metal sensor chip such that 7300 RU (refractive units), equivalent to approximately 7300 pg/mm$^2$, were coupled. Each purified Fab was then injected over the chip at a flow rate of 40 µl/min, limiting the time of interaction of the Fab with the sensor chip to 38 seconds. The change in the attenuated surface plasmon resonance angle was measured as an indicator of the change in the mass of protein bound to the surface. Proteolytically derived chimeric BR96 Fab was analyzed at 5 concentrations ranging from 1.0–9.4 µM; BR96 H3-36 Fab at 5 concentrations from 0.8–4.2 µM; and BR96 H1-4-3 Fab at 5 concentrations from 0.4–4.2 µM. Duplicates of each sample were run, and the data was analyzed with the Biosensor software package. $k_{off}$ and $k_{on}$ were determined from the dissociation and association portions of the binding curve as described by E. Wolff, et al., (1993, *Cancer Res.*, 53:2560–2565), and the ratio of the two taken as $K_d$.

The kinetic constants and $K_d$ are presented below. The affinity of BR96 H3-36 was 4.5 fold greater for Le$^Y$-HSA than the proteolytically derived chimeric BR96 Fab, and BR96 H1-4-3 had 14 fold improved affinity compared to chimeric BR96 Fab. The differences in $K_d$ values were reflected primarily by differences in the $k_{off}$ rate constants.

| Fab | $k_{off}$ (sec$^{-1}$) | $k_{on}$ (M$^{-1}$sec$^{-1}$) | $K_d$ (µM) | Relative to chimeric BR96 Fab |
|---|---|---|---|---|
| Chimeric BR96 | 0.17 | 1.7 × 10$^4$ | 9.9 | 1.0x |
| BR96 H3-36 | 0.043 | 2.0 × 10$^4$ | 2.2 | 4.5x |
| BR96 H1-4-3 | 0.017 | 2.4 × 10$^4$ | 0.72 | 14x |

Figure 10:
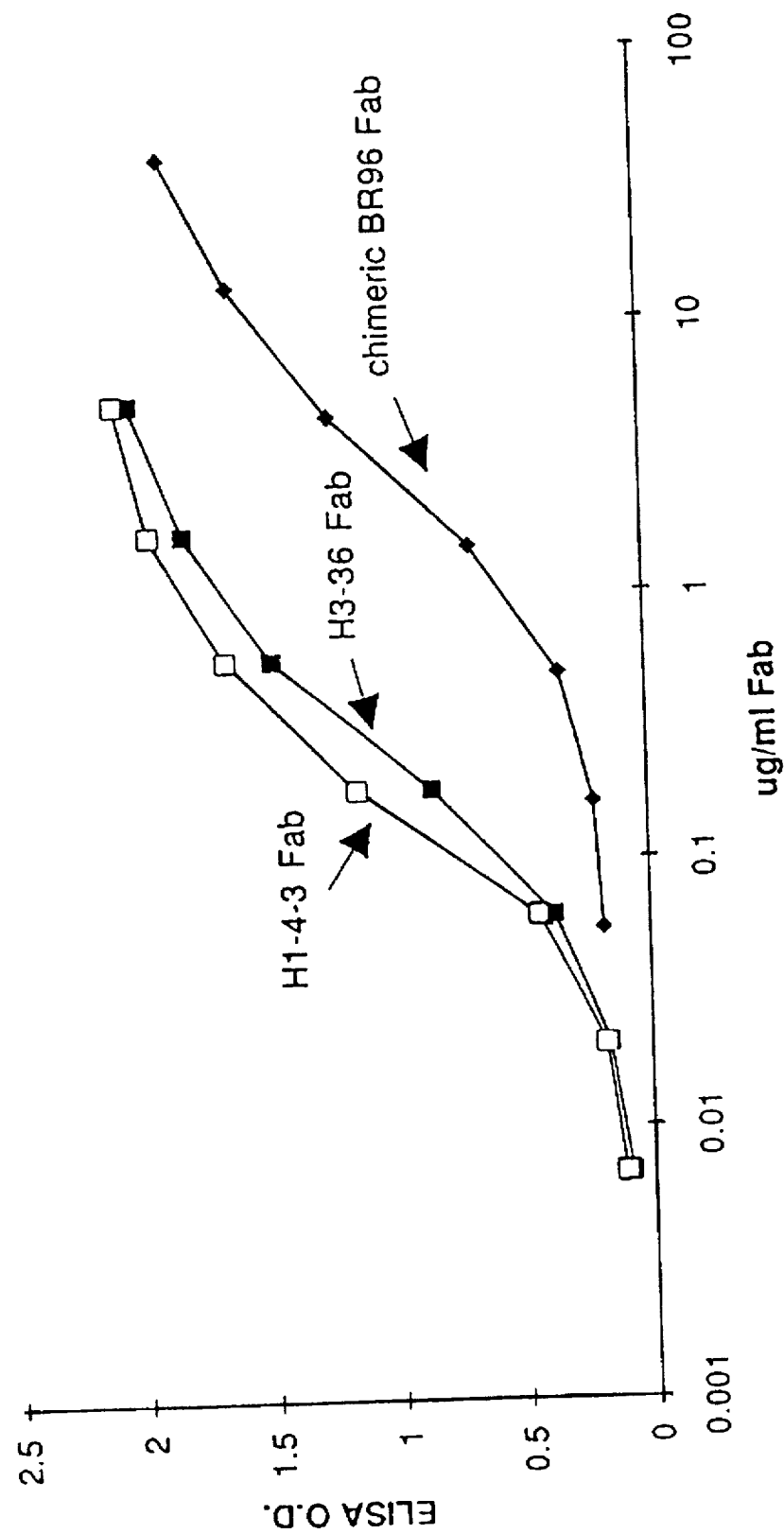
FIG. 10 is a line graph showing that mutant BR96 H1-4-3 Fab and mutant BR96 H3-36 Fab binds to H3396 membranes with an increased affinity compared to ChiBR96 Fab.
Figure 11:
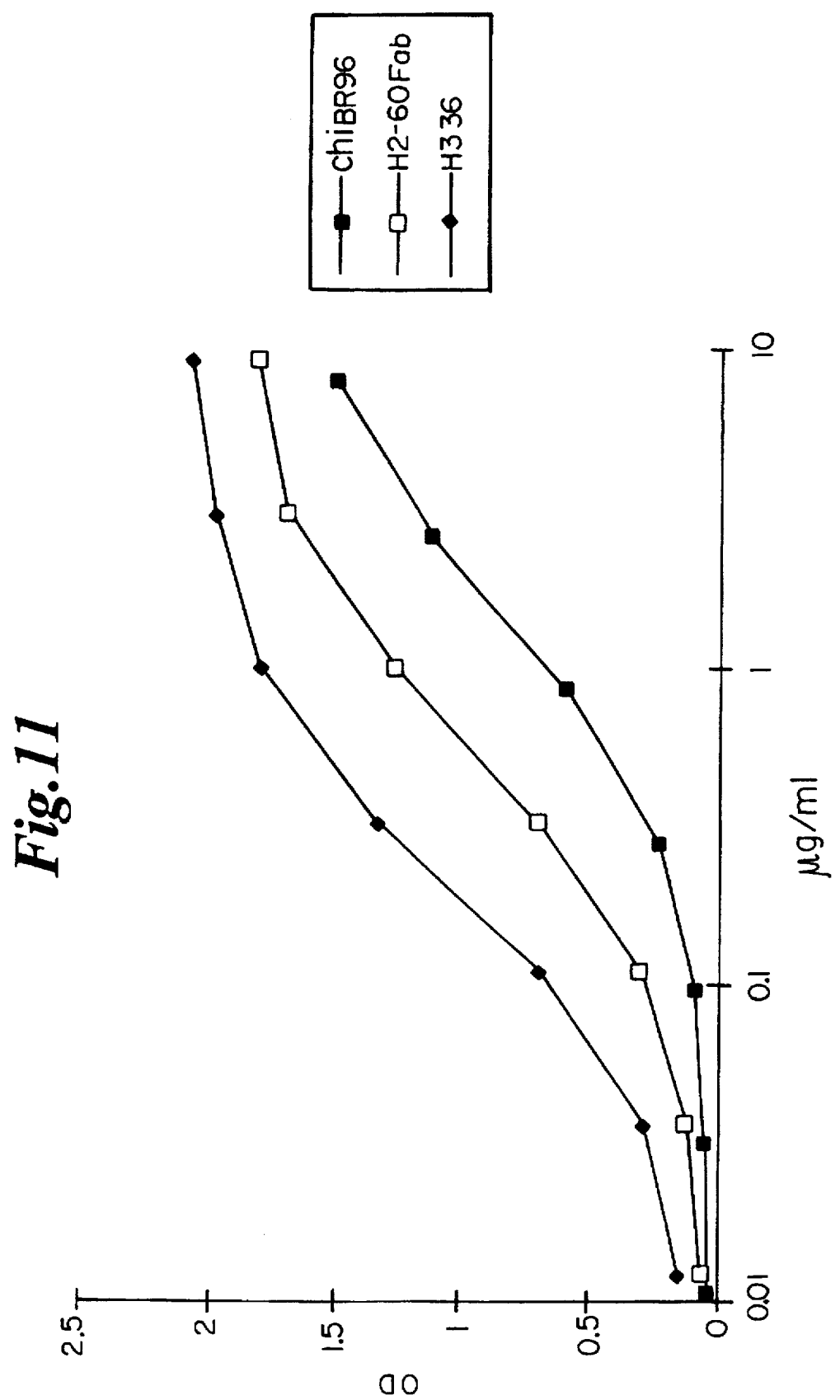
FIG. 11 is a line graph showing the increased affinity of mutant BR96 H2-60 Fab to H3396 tumor cell membranes compared to ChiBR96 Fab.
Figure 12:
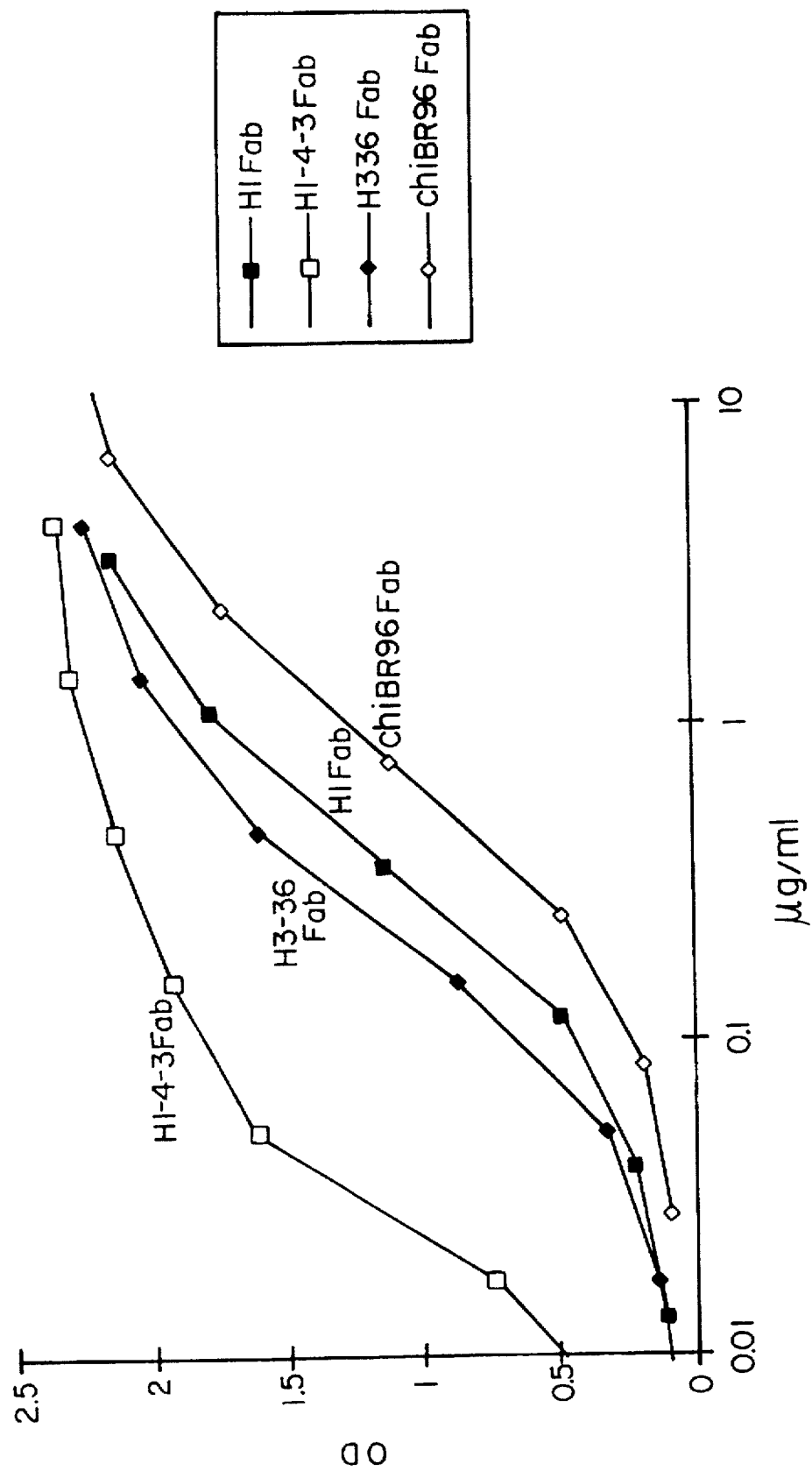
FIG. 12 is a line graph showing that mutants having mutations in CDR1 and CDR3 of the heavy chain (BR96 H1-4-3 Fab) exhibit greater affinity to the target antigen ($Le^Y$-HSA) than either mutant having the mutation in CDR1 (BR96 H1 Fab) or CDR3 (BR96 H3-36 Fab) alone or ChiBR96 Fab.
Figure 13:
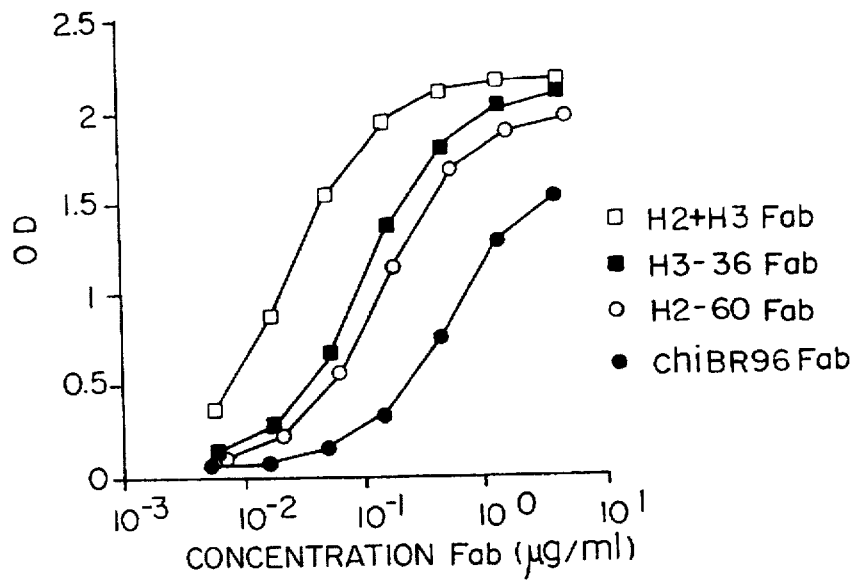
FIG. 13 is a line graph showing that mutants having mutations in CDR2 and CDR3 of the heavy chain (BR96 H2+H3 Fab) exhibit greater affinity to the target antigen (on H3396 membranes) than either mutant having the mutation in CDR2 (BR96 H2-60 Fab) or CDR3 (BR96 H3-36 Fab) alone or ChiBR96 Fab.
Figure 14:
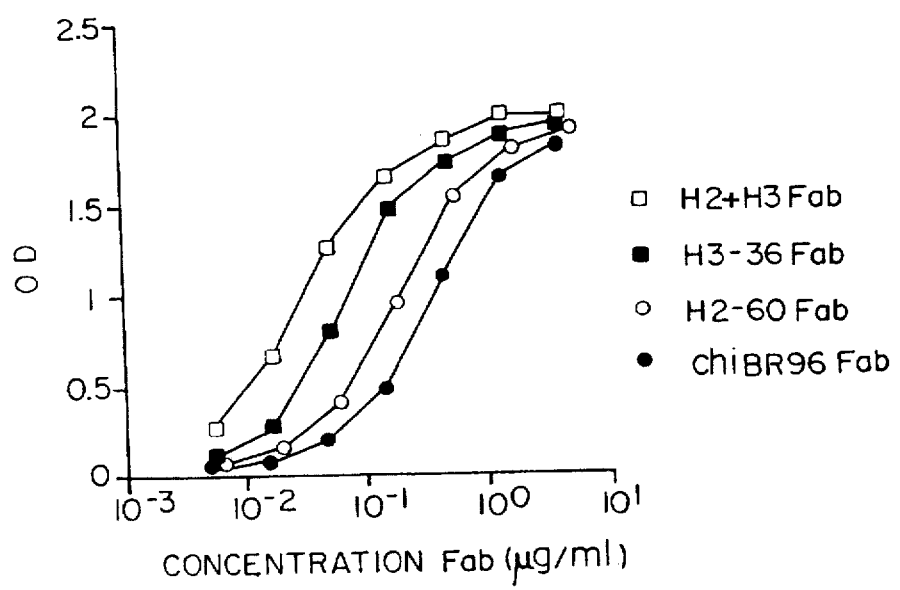
FIG. 14 is a line graph showing that mutants having mutations in CDR2 and CDR3 of the heavy chain (BR96 H2+H3 Fab) exhibit greater affinity to the target antigen (Le$^Y$-HSA) than either mutant having the mutation in CDR2 (BR96 H2-60 Fab) or CDR3 (BR96 H3-36 Fab) alone or ChiBR96 Fab.
Figure 15:
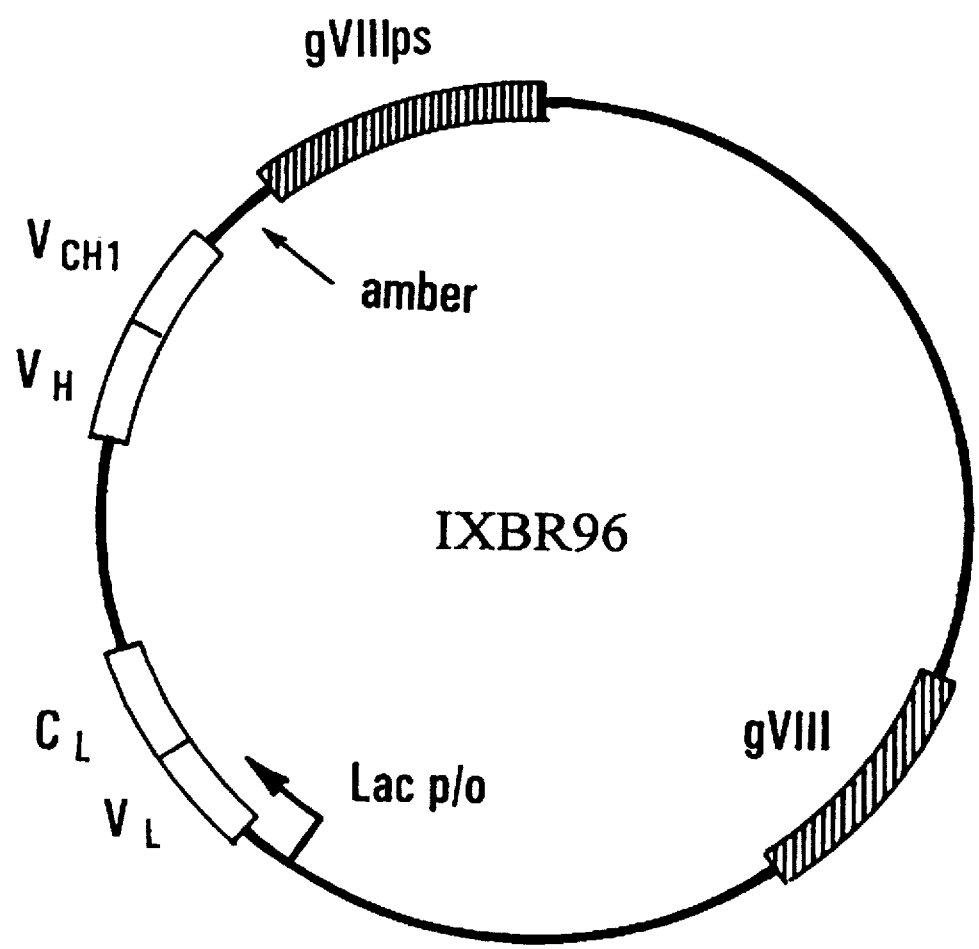
FIG. 15 is a schematic diagram of the pIXBR96 plasmid encoding parental BR96 as a Fab molecule.
Figure 24:
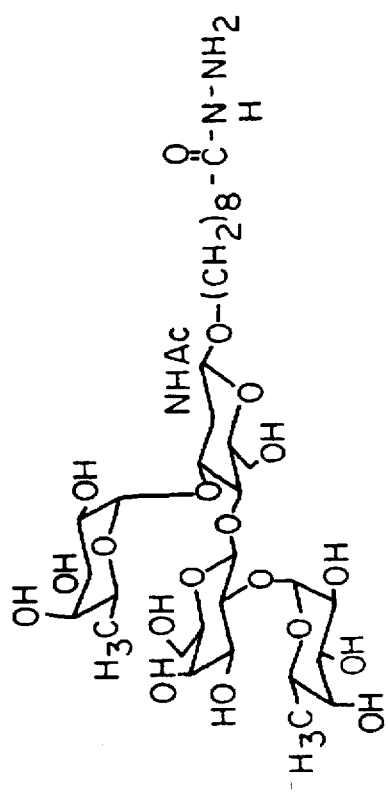
FIG. 24 is the structure of the synthetic tetrasaccharide Le$^Y$ linked to an eight carbon aliphatic spacer and a hydrazide functional group.

ELISA and surface plasmon resonance experiments demonstrated that BR96 H1-4-3 bound with higher affinity to Le$^Y$ than BR96 H3-36. Another ELISA was performed with H3396 membranes (method described above) to examine the differences on tumor antigen. In contrast to the results of assays with Le$^Y$ as antigen, BR96 H1-4-3 did not show the same fold increase compared to BR96 H3-36 but bound very similarly (FIG. 10). Similar results were observed with membranes from a human metastatic lung adenocarcinoma derived cell line, H2987 (Schreiber, G., et al., 1992, *Cancer Res.* 52:3262–3266). Therefore, improving the binding affinity of BR96 or any another anti-Le$^Y$ antibody to the tetrasaccharide, may not necessarily impart increased affinity to tumor antigen (FIG. 24).

EXAMPLE 2

MAMMALIAN EXPRESSION OF MUTANT BR96 ANTIBODY: Mutant BR96, specifically mutant BR96 H3-36 and mutant BR96 H1-4-3, $V_H$ region sequences were introduced into mammalian expression vectors. A variant of the BR96 producing hybridoma H510036 which produced only murine BR96 light chains was transfected by electroporation with the heavy chain vectors, and cells producing whole antibody were cloned. The cells were plated into 96 well tissue culture plates and placed under selective media so that only those cells containing the vectors would survive. Culture supernatants were analyzed after 2–3 weeks for the presence of immunoglobulin. Cells secreting immunoglobulin were cloned by soft agar cloning (Casino, P., Baumal, R., Laskov, R., and Sharff, M. D., "Cloning of mouse myeloma cells and detection of rare variants" J. Cell. Physio. (1972) 79:429–444), and clones producing antibody were isolated. Cultures were grown in volumes of 1–4 liters and antibody was isolated from the supernatant by protein A chromatography.

Mutant BR96 IgG antibody was isolated from culture supernatants and used for histology and measurement of affinities by surface plasmon resonance experiments.

The $V_H$ region sequences from both mutants were amplified by PCR using double stranded phage vector DNA containing each of the respective mutants. For each mutant the amplified DNA encoding the $V_H$ region was inserted into the heavy chain vector containing the constant regions of human IgG4 (Coloma, M. J., Hastings, A., Wims, L. A., Morrison, S. L. "Novel vectors for expression of antibody molecules using variable regions generated by PCR" J. Immunol. Meth. (1992) 152:89–104).

Purified mutant BR96 H3-36 IgG and mutant BR96 H1-4-3 IgG were analyzed for binding specificity to tumor cells, tumor-derived cell lines, and normal tissues by histochemical techniques. The peroxidase-antiperoxidase (PAP) technique (L. A. Sternberger, The unlabeled antibody peroxidase-antiperoxidase (PAP) method; In: Immunocytochemistry, pp. 104–169; New York: John Wiley Sons, Inc., 1979) as modified by H. J. Garrigues, et al. (Detection of a human melanoma-associated antigen, p 97, in histological sections of primary human melanomas; Int. J. Cancer, 29:511–515, 1982) was used.

Murine BR96, with mouse IgG1 heavy chain and mouse kappa chain constant regions, and chimeric BR96 (ChiBR96), with human IgG4 and murine kappa chain constant regions, were included as controls. An additional control included media that used as diluent for the purified antibodies. The results of the experiment are presented in Table 2 (Histology of Mutant BR96 Antibodies).

The mutant antibodies, mutant BR96 H3-36 and mutant BR96 H1-4-3, had similar specificity for tumor tissue, and similar binding to normal colon, pancreas, stomach and esophagus tissues as observed with BR96, both the murine and chimeric forms.

The mutant antibodies did not bind to normal liver and heart tissues, and binding was only slightly more than observed with controls on spleen and kidney. Therefore, introduction of the mutations in the variable sequences of the BR96 CDR regions did not adversely affect tumor specificity nor significantly increase binding to normal tissues.

TABLE 2

Histology of Mutant BR96 Antibodies

| Antibody [1] | mu BR96 | chi BR96 | chi H336 | chi H1-4-3 | Media alone |
|---|---|---|---|---|---|
| Tissues |  |  |  |  |  |
| Carcinoma |  |  |  |  |  |
| ovarian | 4+ | 4+ | 4+ | 4+ | – |
| lung | 4+ | 4+ | 4+ | 4+ | – |
| breast | 4+ | 4+ | 4+ | 4+ | – |
| colon | 4+ | 4+ | 4+ | 4+ | ± |
| Normal |  |  |  |  |  |
| Colon | – | – | – | – | ± |
| pancreas | 3 | 3+ | 3+ | 3+ | ± |
| stomach | 3 | 3+ | 3+ | 3+ | ± |
| esophagus | 2+ | 2+ | 2+ | 1+ | – |
| spleen | ± | ± | ± | ± | – |
| liver | – | – | – | – | – |
| kidney | – | – | – | – | – |
| heart | – | – | – | – | – |
| Cell lines |  |  |  |  |  |
| H3719 | – | – | – | – | – |
| H3396 | 4+ | 4+ | 4+ | 4+ | – |

[1] Heavy chain constant region of murine BR96 is murine IgG1. Heavy chain constant region of chi BR96, H3-36, and H1-4-3 is human IgG4. All antibodies have the murine kappa light chain constant region.

Introduction of the mutations in the whole antibody molecule did affect the functional affinity (avidity) of the antibody. Mutant BR96 H3-36 and H1-4-3 antibodies were analyzed by surface plasmon resonance (BIAcore, Pharmacia) to determine their binding rate constants to Le$^y$-HSA. The data and calculated $K_D$ are presented in Table 3. Mutant BR96 H3-36 antibody has an eight-fold greater functional affinity for Le$^y$-HSA than BR96 antibody, and H1-4-3 has almost 50 fold greater functional affinity compared to BR96.

TABLE 3

BIAcore determination of binding rate constants and calculated $K_D$ of Mutant BR96 H3-36 and H1-4-3 Antibodies

|  | $k_{on}$ (M$^{-1}$S$^{-1}$) | $k_{off}$ (S$^{-1}$) | $K_D$ (M) |
|---|---|---|---|
| chiBR96[1] | 2.9 × 10$^4$ | 60 × 10$^{-4}$ | 210 × 10$^{-9}$ |
| H3-36 | 1.8 × 10$^4$ | 3.0 × 10$^{-4}$ | 16 × 10$^{-9}$ |
| H1-4-3 | 2.4 × 10$^4$ | 0.96 × 10$^{-4}$ | 4 × 10$^{-9}$ |

[1] chi BR96 has human IgG1 heavy chain constant region and human kappa light chain constant region. H3-36 and H1-4-3 have human IgG4 heavy chain constant regions and murine kappa light chain constant regions.

EXAMPLE 3

SFv Molecules with Mutant BR96 Sequences

The H3-36 mutation, i.e., the change of aspartic acid to alanine at position 101 in CDR 3 of the heavy chain of BR96 was introduced into single chain Fv (sFv) and sFv-PE40 fusion protein constructs.

Additionally, mutant BR96 H3-36 sFv molecule was also constructed in a M13 vector.

Expression of Mutant BR96 sFv

Figure 16:
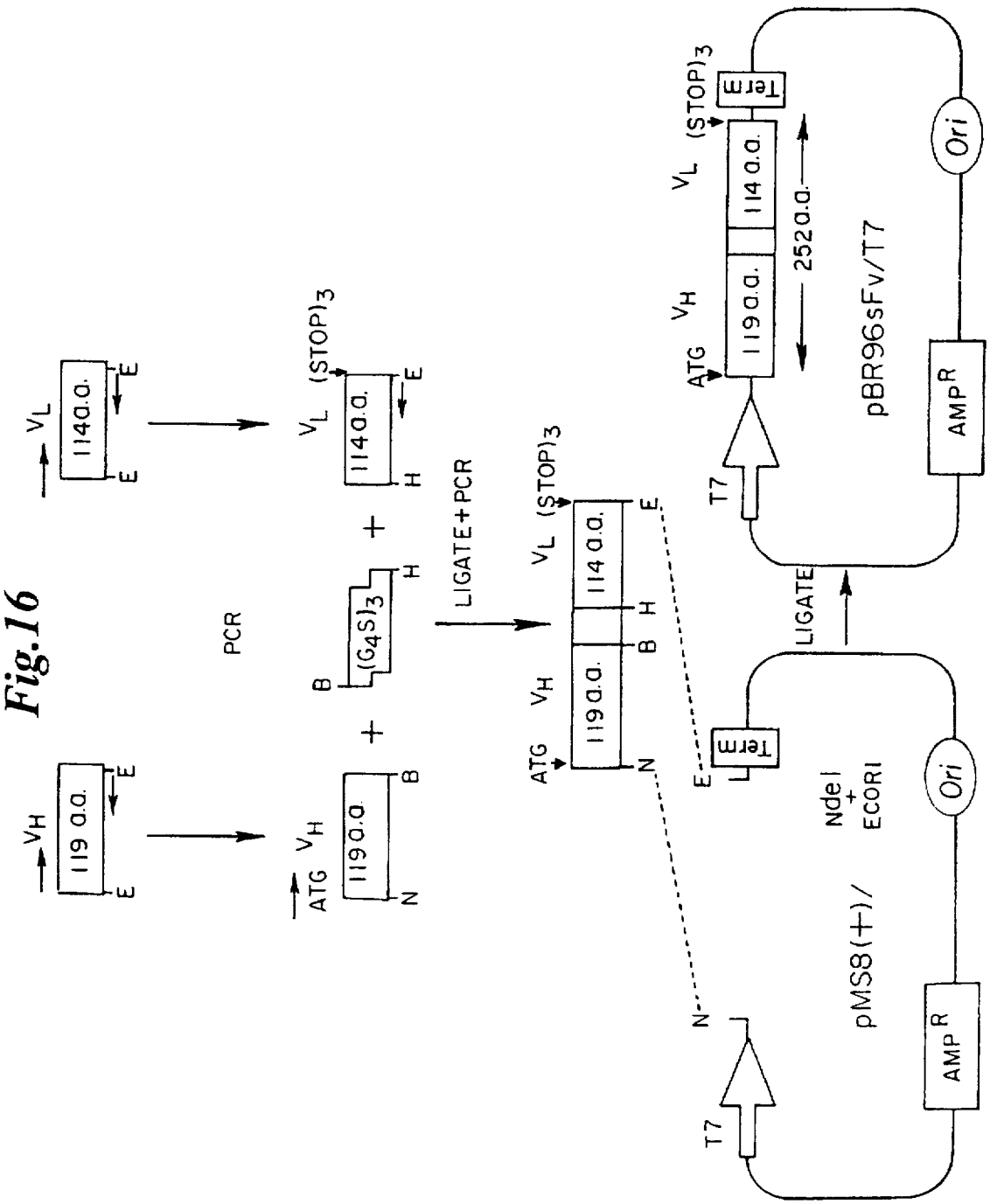
FIG. 16 is a schematic diagram showing the construction of pBR96sFv-T7 expression plasmid.

Mutant BR96 H3-36 was introduced into the BR96 sFv gene fusion vector, designated pBR96sFv/T7, which was constructed (FIG. 16). The BR96 sFv molecule consists of the $V_H$ region of BR96 covalently linked to the $V_L$ region of BR96 by a (gly$_4$ser)$_3$ peptide linker (Huston, J. S., et al., 1988, Protein engineering of antibody binding sites: Recovery of specific activity in an anti-digitoxin single-chain Fv analogue produced in Escherichia coli, Proc. Natl. Acad. Sci. U.S.A. 85:5879–5883; Chaudhary, V. K., et al., 1989, A recombinant immunotoxin consisting of two antibody variable domains fused to Pseudomonas exotoxin, Nature (London) 339:394–397). The (gly$_4$ser)$_3$ peptide linker is merely one example of an appropriate linker. A whole range of short linkers may be used to join immunoglobulin chains of a $V_L$+$V_H$ (F$_v$) (Huston, J. S., Levinson, D., Mudgett-Hunter, M., Tai, M. S., Novotny, J., Margolies, M. N., Ridge, R. J., Bruccoleri, R. E., Haber, E., Crea, R., Oppermann, H. (1988) Protein engineering of antibody binding sites: recovery of specific activity in an antidigitoxin single-chain Fv analogue produced in Escherichia coli. Proc. Natl. Acad. Sci. USA (85:5879–5883; Pluckthun, 1991).

The mutant BR96 H3-36 sFv (referred to herein as mutant BR96 H3-36 (D:A-101)) was made by designing an oligonucleotide that contained the mutation flanked on both 3' and 5' ends by sequences homologous to BR96. PCR amplification using this oligonucleotide followed by hybridization experiments to choose clones with plasmid that hybridized to the mutant oligonucleotide with greatest stringency resulted in isolation of a plasmid containing the H3-36 mutation. The sequence of the BR96 sFv (D:A-101) plasmid was confirmed by nucleotide sequencing.

Expressed BR96 sFv and mutant BR96 sFv (D:A-101) were isolated from inclusion bodies formed within bacteria. The inclusion bodies were isolated, denatured, and the protein refolded and purified as described by P. N. Friedman, et al. (1993, BR96 sFv-PE40, A potent single-chain immunotoxin that selectively kills carcinoma cells; Cancer Res. 53:334–339).

Figure 17:
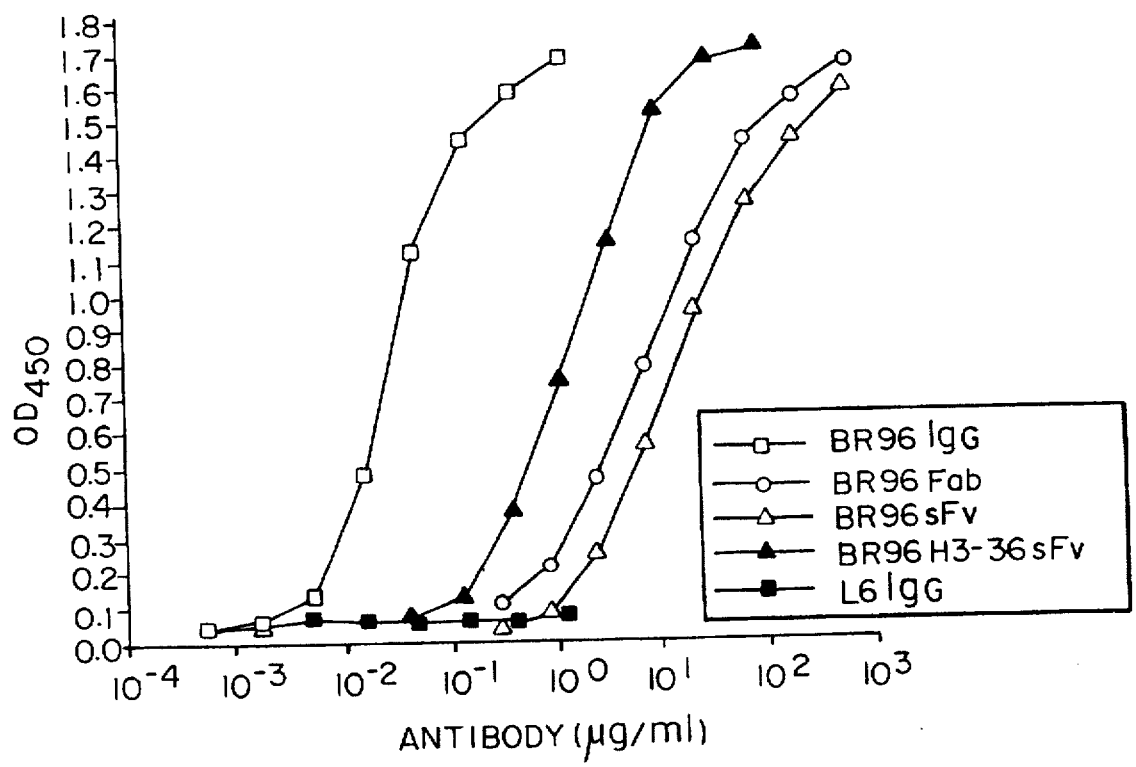
FIG. 17 is a line graph showing the binding of mutant BR96 sFv (H3-36) (produced in bacteria from the plasmid of FIG. 16 and represents refolded material) to Le$^Y$-HSA.
Figure 18:
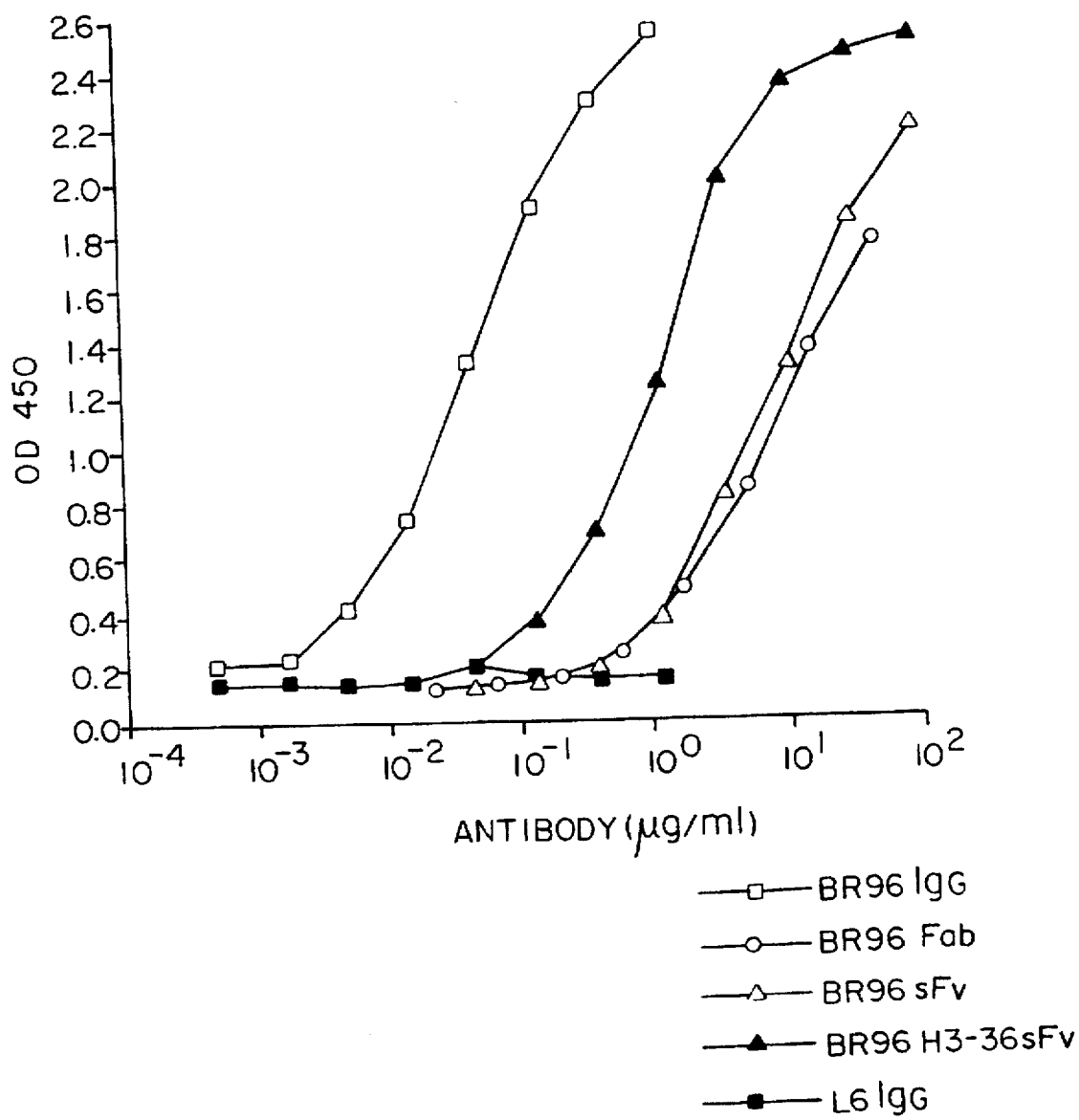
FIG. 18 is a line graph showing the binding of mutant BR96 sFv (H3-36) produced in bacteria from the plasmid of FIG. 16 and represents refolded material) to H3396 tumor cell membranes as described in Example 3.

The purified and refolded sFv molecules were analyzed for binding to Le$^y$-HSA and tumor cell membranes by ELISA (FIGS. 17 and 18). BR96 IgG and BR96 proteolytically derived Fab were included in the assay, and L6 IgG was included as a negative control.

Similar data were obtained from surface plasmon resonance experiments with BR96 sFv-Pe40 and mutant H3-36 sFv-PE40 fusion proteins. Construction of the BR96 sFv-PE40 vector and its expression are described by P. Friedman, et al. (1993) BR96 sFv-PE40, A potent single-chain immunotoxin that selectively kills carcinoma cells; Cancer Res. 53:334–339). The asp→ala 101 mutation was introduced by PCR as described for mutant BR96 sFv (D:A-101).

Expression of Mutant BR96 sFv

The BR96 sFv and mutant H3-36 sFv sequences ($V_H$ region of BR96 and H3-36 covalently linked to the $V_L$ region of BR96 by a (gly$_4$ser)$_3$ peptide linker, respectively) were introduced into M13 vectors. The sFv molecules were linked at the 5' (V$_H$) end to a bacterial leader peptide, pel B, so that the polypeptide was directed to the periplasmic space of the bacteria (FIG. 16).

The sFv molecules were isolated from the periplasmic space of the bacteria. The sFv's were isolated from the periplasm as previously described for the Fab molecules, and so denaturation and refolding were not required as for the Sfv molecules in inclusion bodies described above.

Figure 19:
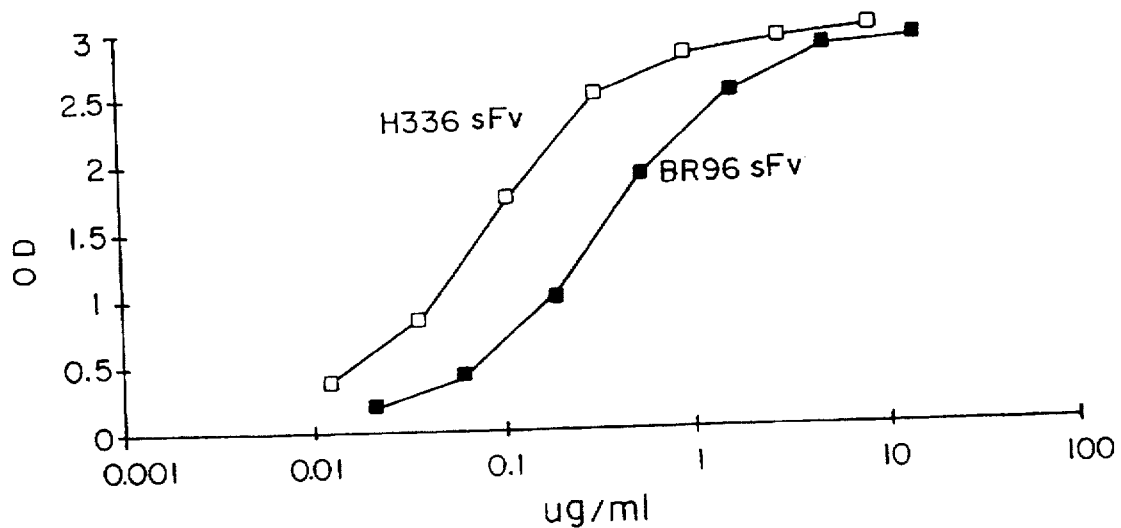
FIG. 19 is a line graph showing the binding of mutant BR96 sFv (produced in M13 infected bacteria with a signal peptide derived from the periplasm and does not require refolding) to Le$^Y$-HSA.

Binding of BR96 and mutant BR96 H3-36 Sfv in periplasmic preparations to Le$^Y$-HSA were compared by ELISA and the results are shown in FIG. 19. The same fold difference, 4–5 times, observed with Fab molecules from periplasm fractions was observed with the single chain molecules.

Construction of BR96 SFV Expression Plasmid

The expression plasmid used for production of BR96 sFv in *E. coli* utilizes the bacteriophage T7 RNA polymerase promoter (Studier and Moffat, 1986). PCR was used to modify the 5' and 3' termini of both BR96 V regions in order to create restriction sites compatible with joining an oligonucleotide duplex encoding a flexible (Gly$_4$Ser)$_3$ polypeptide linker (Huston et al., 1988; Chaudhary et al., 1989).

The 5' V$_H$ PCR primer (5'-GCTAGACATATGGAAGT GAATCTGCTGGAGTCTGGGGGA-3' (SEQ ID NO:41)) was designed to encode a unique Nde 1 restriction site (underlined) which includes an ATG translational initiation codon (bold) and the first nine codons of the V$_H$ gene. In contrast, the 3'V$_H$PCR primer (5'-GCTAGAGGATCCTAC AGAGACCGTGACCAGAGTCCCTTG-3' (SEQ ID NO:42)) encoded nine COOH-terminal codons with J-region complementarity and a 3' BamH1 site (underlined).

The 5' V$_L$ PCR primer (5'TACACAAAGCTTGATGTT TTGATGACCCAAATTCCA-GTC-3' (SEQ ID NO:43)) encoded the first nine codons of the mature V$_L$ gene and a 5' HindIII site (underlined).

After annealing, duplex 51-mer oligonucleotides (5'GATCCGGAGGTGGAGGTTCTGGTGGAGGTGGAT CTGGAGGTGGAGGTTCTA-3' (SEQ ID NO:44) and 5'-AGCTTAGAACCTCCACCTCCAGATCCACCTCCAC CAGAACCTCCACCTCCG-3' (SEQ ID NO:45)) encoding a 15 amino acid linker, were ligated between unique BamH 1 (3' end of V$_H$) and HindIII (5' end of V$_L$) sites. Using standard procedures, the ligation mixture was then PCR amplified with the 5' V$_H$ and 3' V$_L$ primers, digested with Nde 1 and EcoR 1 and cloned into Nde 1- and EcoR 1-digested pMS8(+)(Sambrook et al., 1989). The resulting expression plasmid, pBR96sFv/T7 (FIG. 16) encoding the BR96 sFv gene fusion, was confirmed by DNA sequence analysis.

pBR96sFv-T7 expression plasmid was constructed by designing PCR primers which altered 5' and 3' EcoRI termini of both BR96 V region genes. Subsequent to amplification, BR96 V$_H$ was contained on a NdeI-BamHI fragment while BR96 V$_L$ was contained on a HindIII-EcoRI fragment containing 3 in-frame translational stop codons. These PCR products were ligated with duplex oligonucleotides encoding a flexible polypeptide linker and an aliquot of the ligation was used in PCR as shown.

The resulting PCR product, comprising a gene fusion of approximately 760 bp, was subcloned as an Nde-EcoRI fragment. The expression vector, pBR96sFv/T7, consisting of V domains of the BR96 heavy chain (119 amino acids) and light chain (114 amino acids), tethered with duplex oligonucleotides encoding a 15 amino acid flexible polypeptide linker ((Gly$_4$Ser)$_3$) was constructed for expression of BR96 sFv in *E. coli*. The relative positions of Nde I(N), Bam HI (B), HindIII (H) and EcoRI (E) sites, transcriptional termination sequences (Term), origin of replication (ori) and β-lactamase gene (AmpR) are indicated.

Expression and Purification of BR96 SFV Protein

BL21 (λDE3) cells (Studier & Moffat, 1986) were transformed with expression plasmid pBR96sFv-T7, grown in "Terrific-Broth" medium (Gibco-BRL, Gaithersburg, Md.) containing 100 µg/ml ampicillin at 37° C. and induced with 1 mM IPTG in the logarithmic phase at an OD$_{650}$ of 2.0. The cells were harvested 2 hours later. For analytical analysis, 1 ml samples were harvested by centrifugation and osmotically shocked in cold H$_2$O for 10 min.

The cells were centrifuged again and the cell pellets were resuspended in 10 mM Tris-HCl, pH 7.4/10% glycerol. Aliquots prepared from approximately 10$^8$ spheroplasts were subjected to SDS-PAGE and stained (Laemmli, 1970) or subjected to immunoblot analysis using the anti-idiotypic 757-4-1 mAb.

A bulk bacterial cell pellet prepared from a 10L fermentation was processed as described above and inclusion bodies were isolated as previously described (Friedman et al., 1993).

Extensively washed inclusion bodies were then denatured in 7M guanidine-HCl, pH 7.4 (Sigma), diluted in 100 mM Tris, pH 7.4–0.4M L-arginine-4 mM oxidized glutathione (Sigma) at 4° C. to a final concentration not exceeding 100 µg/ml and extensively dialyzed against 20 mM Tris-HCl (pH 7.4). After overnight dialysis, the refolded protein was purified by anion-exchange (Q-sepharose, Pharmacia) and gel filtration chromatography (TSK-3000, TosoHaas, Inc.) as described previously (Friedman et al., 1993). BR96 sFv protein was pooled and quantitated using the Bradford assay (Bradford, 1976).

Plasmid Construction, Protein Expression and Purification

The cloning strategy for assembling a BR96 sFv gene fusion and the structure of the BR96 sFv is shown in FIG. 16. Plasmid pBR96sFv/T7 utilizes the T7RNA polymerase transcriptional promoter and encodes 119 amino acids of the BR96 heavy chain, a 15 amino acid polypeptide linker composed of (Gly$_4$Ser)$_3$ and 114 amino acids of the BR96 light chain.

pBR96sFv/T7 was transformed into the *E. Coli* strain BL21 (λDE3), and after induction with IPTG, the recombinant protein was found to be localized primarily to inclusion bodies.

Since the expressed sFv accumulates as an insoluble aggregate, denaturation and refolding are required for the purification of active protein. Inclusion bodies containing BR96 sFv were denatured and renatured as described in Materials and Methods. Purification was performed by consecutive chromatography on Q-Sepharose anion-exchange and TSK-3000 gel-filtration columns. The fractions containing the active protein were pooled, concentrated approximately 20-fold and aliquoted for storage at –20° C. The recovered BR96 sFv protein was estimated to be 290% homogeneous by silver-stained gel analysis and was used for binding and internalization studies. Amino-terminal amino acid sequence analysis confirmed the first 25 amino acids expected for BR96 sFv.

EXAMPLE 4

Construction of Single-Chain FV BR96 and Mutant BR96 H3-36 In IXSYS$^R$ M13 Vector

Description of Cloning Method

M13 vectors coding for BR96 and mutant BR96 H3-36 scFvs were designed to produce the polypeptide sequence: pel B leader-VH-(Gly$_4$Ser)$_3$ linker-VL-decapeptide. The scFvs were constructed by first deleting the M13IXBR96 and M13IXBR96 H3-36 templates of sequence starting with the BR96 V$_L$-Ck gene continuing through the sequence coding for the bacterial alkaline phosphatase leader peptide. Rejoining this vector abuts the amino terminus of the BR96 heavy chain sequence to the carboxy terminus of the bacterial pectate lyase (pel B) leader peptide and deletes the entire BR96 light chain.

PCR is then used to amplify BR96 and mutant BR96 H3-36 V$_H$ sequences from phage M13IXBR96 and M13IXBR96 H3-36 with forward primers containing pel B leader peptide sequence and reverse primers containing the (Gly$_4$Ser)$_3$ linker sequence in addition to nucleotide sequence complementary to the decapeptide sequence contained in the M13 vector.

The PCR amplified BR96 and mutant BR96 H3-36 V$_H$ products are used to replace the endogenous BR96 and mutant BR96 H3-36 V$_H$ genes present in the light chain-deleted M13 vectors by hybridization mutagenesis. PCR is then used to amplify the (Gly$_4$Ser)$_3$ linker-BR96 V$_L$ sequence from the plasmid pSE1.0 Ala101 (FIG. 20) with forward primers containing carboxy-terminal BR96 V$_H$ nucleotide sequences and reverse primers containing sequences complementary to the decapeptide sequence contained in the M13 vector. The introduction of the PCR amplified (Gly$_4$Ser)$_3$ linker BR96 V$_L$ sequences complete the construction of the scFvs.

Methods

All oligonucleotides were synthesized by β-cyanoethyl phosphoramidite chemistry on an Applied Biosystems 394 DNA Synthesizer and purified using oligonucleotide purification cartridges (Applied Biosystems, Foster City, Calif.).

Oligonucleotide 961 (5'-CAGATTCACTTCGGCCATG GCCACAGGG-3' (SEQ ID NO:46)) was used to introduce an NcoI site (underlined) by site-directed mutagenesis at the junction between the alkaline phosphatase leader peptide and the BR96 and the mutant BR96 H3-36 sequences in clones M13IXBR96 and M13IXBR96 H3-36, respectively. M13IXBR96 and M13IXBR96 H3-36 clones containing the NcoI site were identified by restriction digestion with the NcoI endonuclease.

Three clones from each mutagenized preparation were pooled and digested with NcoI. The digested products were electrophoresed on an 0.8% low melting temperature agarose gel buffered in Tris-acetate buffer. The larger of the two resulting restriction fragments containing the deleted BR96 light chain through alkaline phosphatase leader peptide sequence was excised from the gel and the DNA fragment purified. 50 ng of purified DNA was self-ligated and electroporated into E. coli strain DH10B as described.

Replica filter lifts were prepared (Huse et al. 1992) and one filter was probed with goat anti-human kappa antibody conjugated to alkaline phosphatase, and the second filter probed with the anti-idiotype antibody 757-4-1 which recognizes BR96V$_H$. Four M13IXBR96 ΔV$_L$ clones and four M13IXBR96 H3-36 ΔV$_L$ clones exhibiting loss of kappa chain reactivity but presence of heavy chain reactivity were pooled and used to prepare uridinylated single-stranded template for the introduction of the PCR amplified (Gly$_4$Ser)$_3$ linker-BR96 V$_L$ sequence by hybridization mutagenesis. The final mutagenesis step deletes the heavy chain CH$_1$.

Oligonucleotide 977 (5'-GGGACTCTGGTCACGGTCT CTTCAGGATCCGGA-3' (SEQ ID NO:47)) is a forward PCR primer that has BR96 V$_H$ sequences at the 5' end and (Gly$_4$Ser)$_3$ linker sequences at the 3' end. The carboxy-terminal Leu(CTG) in BR96 V$_H$ has been replaced with Ser(TCA) as indicated by the underlined sequence. This was done because the scFv BR96 molecule constructed has a Ser rather than a Leu at this position and it was not known how a Leu would effect the functional activity of the scFv.

Oligonucleotide 911 (5'-TGGGTAGGATCCACTAGTG CGTTTGATCTCCAGCTTGG-3' (SEQ ID NO:48)) is a reverse PCR primer that has complementary BR96V$_L$ sequences at the 3' end and decapeptide sequences at the 5' end. Plasmid pSE 1.0 Ala101 was linearized with restriction endonuclease XhoI and resuspended at a concentration of 2 ng/μl. 10 ng of pSE 1.0 Ala101 was used for amplifying the (Gly$_4$Ser)$_3$ linker-BR96V$_L$ sequence using primers 977 and 911. The PCR amplified DNA was purified by polyacrylamide gel electrophoresis and subsequently introduced into M13IXBR96 ΔV$_L$ and M13IXBR96 H3-36 ΔV$_L$ templates by hybridization mutagenesis. The resulting M13IXBR96 and M13IXBR96 H3-36 scFv clones were screened for binding to H3396 tumor cells and tumor reactive clones identified, plaque-purified, and correct DNA sequence confirmed by DNA sequence analysis (FIG. 19).

EXAMPLE 5

Preparation of Single-Chain BR96 and Mutant BR96 sFv-PE40 Immunotoxin

Figure 20:
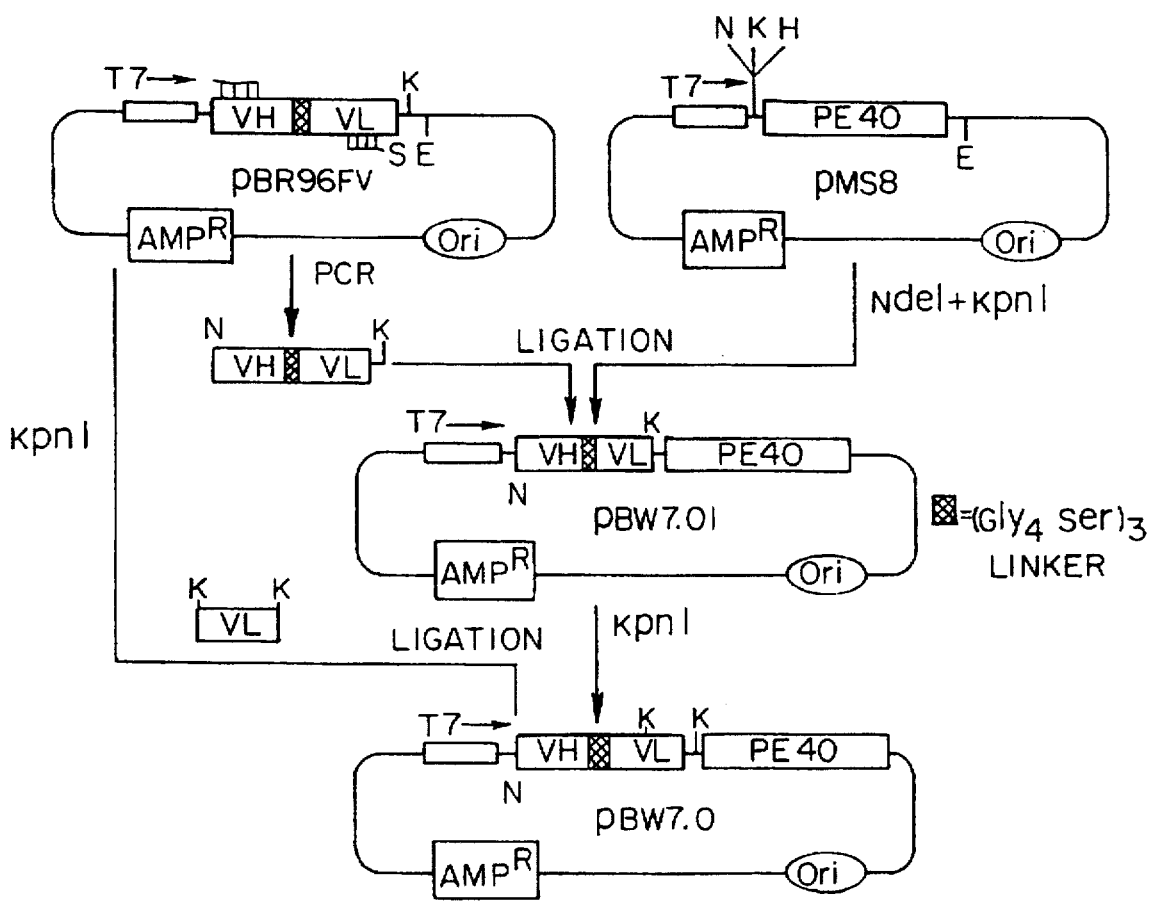
FIG. 20 is a schematic illustration of the construction of expression plasmid pBW 7.0 encoding BR96 sFv-PE40 (E. Eco RI; H, Hind III; K, KPNI; N, NDe I; S, Sal I; (Gly$_4$Ser)$_3$ represents a 15 amino acid linker).

This example describes the preparation and characterization of cytotoxicity of a single-chain immunotoxin, BR96 and mutant BR96 sFV-PE40, consisting of the cloned heavy and light chain Fv portions of the BR96 and the mutant BR96 monoclonal antibody of the invention linked to PE40 (FIG. 20).

In order to produce a single-chain recombinant immunotoxin, the Fv domains of the light and heavy chains of BR96 IgG were isolated from plasmid pBR96 Fv containing the BR96 Fv sequences using PCR amplification.

Starting with BR96 sFv sequence encoded by plasmid pBR96Fv a 550 bp sequence corresponding to the variable heavy and variable light chains connected with a synthetic (Gly$_4$Ser)$_3$ hinge region up to the Kpn I restriction site in the light chain, was used to PCR-amplify with specific primers (Friedman et al., supra.).

After PCR-amplification and digestion with Nde I and Kpn I a 550 bp Nde I-Kpn I fragment was ligated into a 4220 bp Nde I-Kpn I vector fragment prepared from plasmid pMS8, which encodes the gene for PE40 under the transcriptional control of the T7 promoter [Studier et al., J. Mol. Biol. 189:113–130 (1986); Debinski et al., Monoclonal antibody C242-Pseudomonas exotoxin A: a specific and potent immunotoxin with antitumor activity, J. Clin. Invest., 90:405–411, 1992)].

The product of this ligation was an intermediate vector designated pBW 7.01. Subsequently, the 227 bp Kpn I fragment from mutant pBR96 Fv was subcloned into the unique Kpn I site of pBW 7.01. The resulting plasmid pBW 7.0, encoding the BR96 sFv-PE40 gene fusion, was con-

43 firmed by DNA sequence analysis. For production of an analogous plasmid containing mutant BR96, restriction fragments or synthetic oligos were used to insert mutant sequences into plasmid pBW7.0.

Expression and Purification of BR96 and Mutant BR96 sFv-PE40

The plasmids encoding BR96 and mutant BR96 sFv-PE40 were separately transformed E. coli BL21 (λDE3) cells cultured in Super Broth (Digene, Inc., Silver Springs, Md.) containing 75 µg of ampicillin per ml at 37° C. When absorbance at 650 nm reached 1.0, isopropyl 1-thiol-B-D-galactopyranoside (IPTG) was added to a final concentration of 1 mM, and cells were harvested 90 minutes later.

Upon induction with IPTG, E. coli cells transformed with the plasmids expressed large amounts of fusion protein that was localized to the inclusion bodies. The bacteria were washed in sucrose buffer (20% sucrose, 30 mM Tris-HCl (pH 7.4), 1 mM EDTA) and were osmotically shocked in ice-cold $H_2O$ to isolate the periplasm.

44

Subsequently, inclusion bodies were isolated away from the spheroplast membrane proteins by extensive treatment with Tergitol (Sigma) to remove excess bacterial proteins, followed by denaturation in 7M guanidine-HCl (pH 7.4), refolding in PBS supplemented with 0.4M L-Arginine and extensive dialysis against 0.02M Tris, pH 7.4.

Protein was purified using anion-exchange on a Q-Sepharose column and fractions containing mutant BR96 sFv-PE40 were then pooled and separated by gel-filtration (on a TSK-3000 column) chromatographies with a Pharmacia fast protein liquid chromatograph (FLPC) system as described by Siegall et al., Proc. Natl. Acad. Sci. USA 85:9738–9742 (1988).

Direct Lewis Y Determinant Binding ELISA

Figure 21:
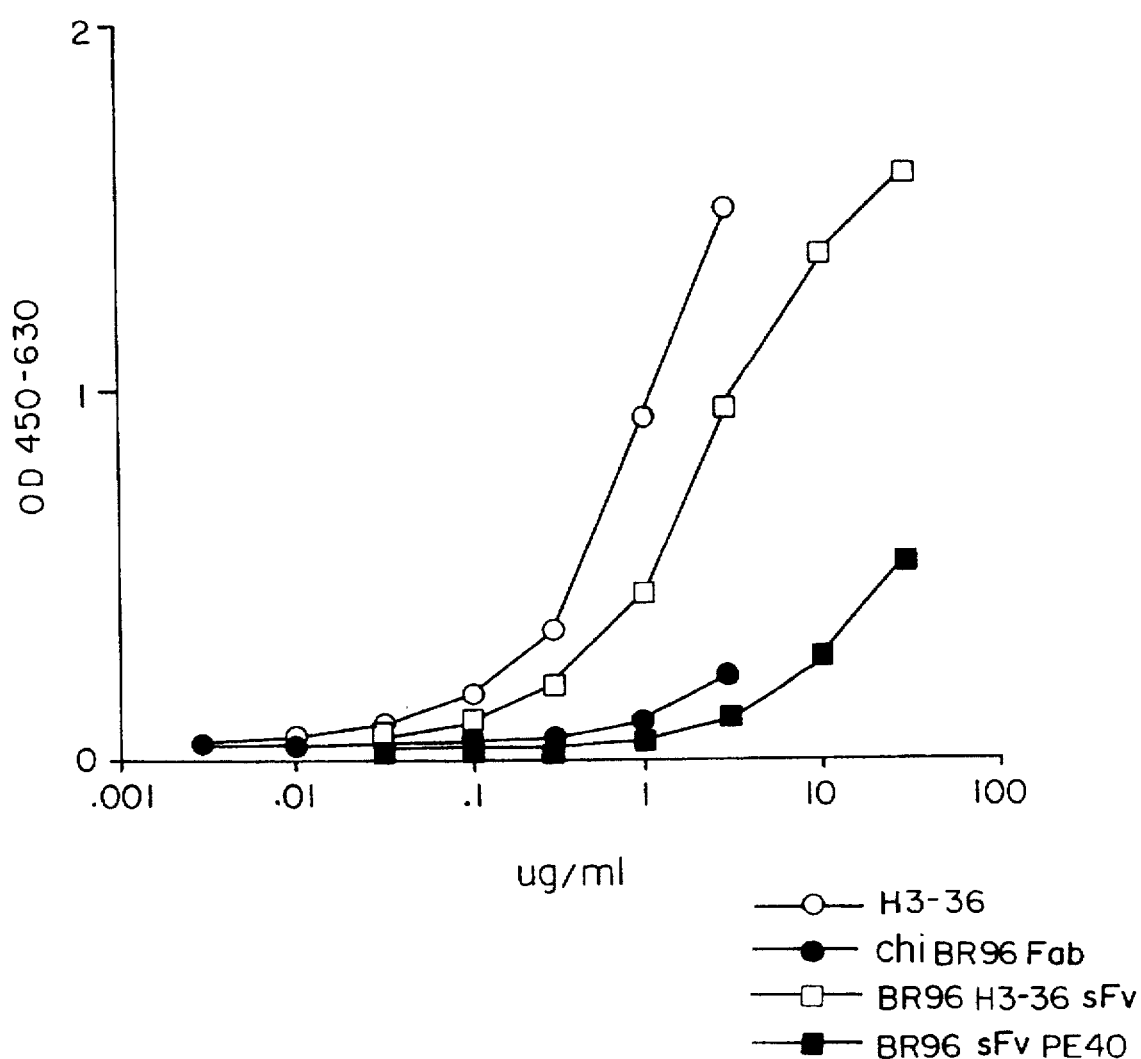
FIG. 21 is a line graph showing the results of an ELISA assay wherein BR96 H3-36 sFv-PE40 expressed by the plasmid of FIG. 20 binds to H3396 membranes with increased affinity compared to BR96 sFv-PE40.
Figure 22:
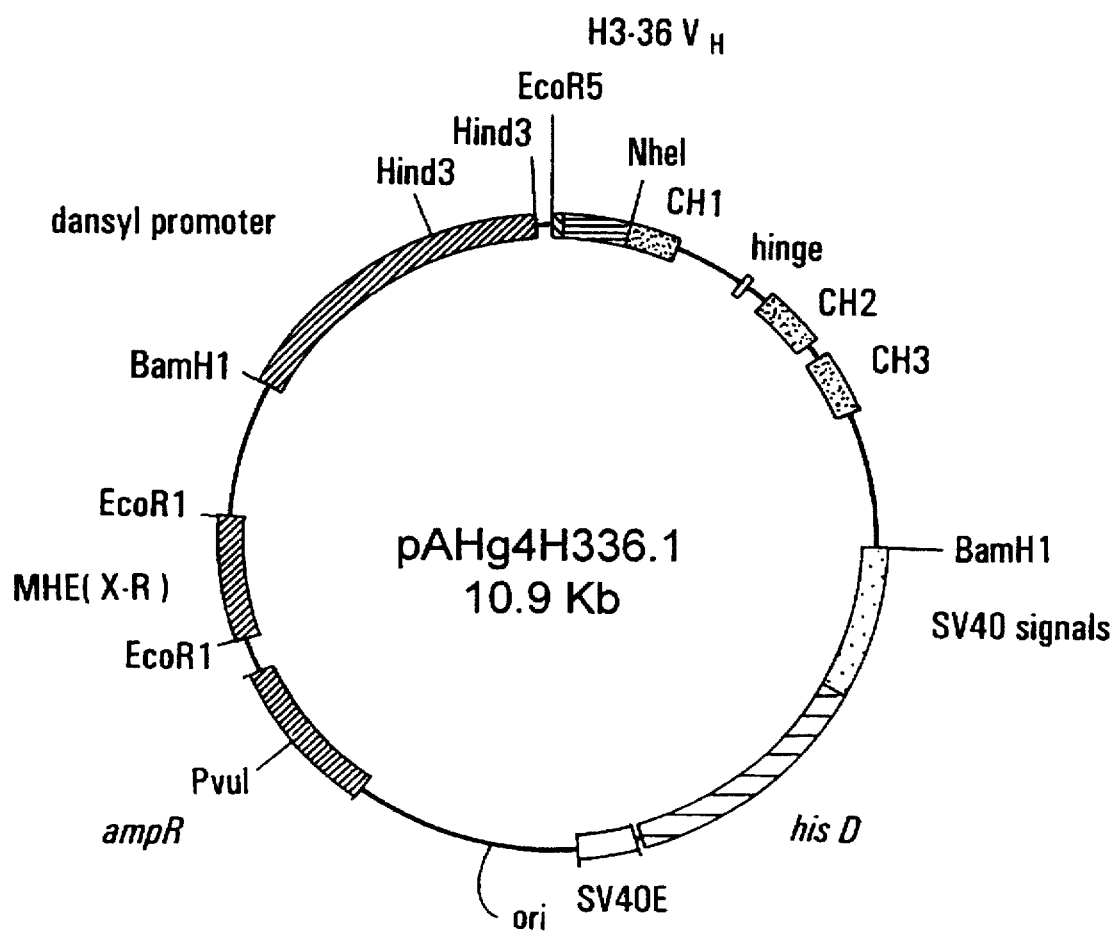
FIG. 22 is a schematic diagram of the pAHg4H336.1 (10.9 kb) plasmid which encodes the heavy chain of the variable and constant region of mutant BR96, e.g., H3-36. This plasmid was used to make whole antibody in mammalian cells.
Figure 23:
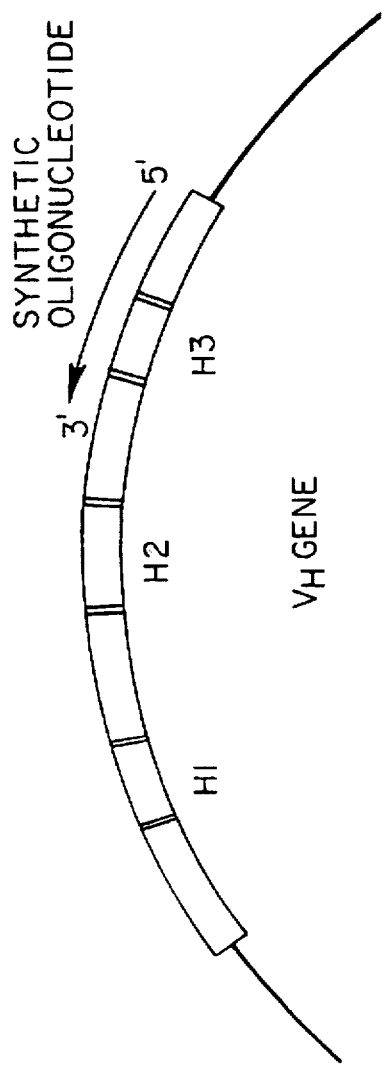
FIG. 23 is a schematic diagram of the single strand M13 plasmid illustrating how synthetic codon-based oligomers are annealed to parental BR96 template to create library of mutations.

In order to test the relative binding activities of mutant BR96 sFv-PE40 compared to BR96 sFv-PE40, a direct binding assay was performed in which H3396 tumor cell membrane were coated on ELISA plates and the binding of the mutant BR96 sFv-PE40 molecule was shown to be improved over its BR96 counterpart (FIG. 21).

What is claimed is:

1. A nucleic acid sequence encoding a mutant polypeptide derived from BR96 (ATCC HO10036) comprising CDR1, CDR2, and CDR3, wherein CDR3 includes therein the sequence GGC CTG GCG GAC GGG GCC TGG (SEQ ID NO:56) beginning at nucleotide position 296 and ending with nucleotide position 327 as shown in FIG. 2 (SEQ ID NO:9).

2. The nucleic acid of claim 1, wherein CDR1 includes therein the sequence comprising GGA TTC CCG TTC GCG TCG TAT (SEQ ID NO:57) beginning at nucleotide position 77 and ending with nucleotide position 97 as shown in FIG. 4 (SEQ ID NO:9).

3. A nucleic acid molecule encoding a mutant polypeptide derived from BR96 (ATCC HB10036) comprising an amino acid sequence including therein a CDR including a sequence Gly Leu Xaa Asp Gly Ala Trp (SEQ ID NO:49) beginning at amino acid position 99 and ending with amino acid position 105 (SEQ ID NO:49), and wherein Xaa is alanine, arginine, serine, glycine, tyrosine or valine.

4. A nucleic acid molecule encoding a mutant polypeptide derived from BR96 (ATCC HB10036) comprising CDR1, CDR2, and CDR3, wherein CDR1 includes therein the sequence Gly Phe Thr Phe Ser Asp Tyr Tyr Met Tyr (SEQ ID NO:51), wherein CDR2 includes therein the sequence Tyr Ile Ser Gln Xaa Gly Asp Ile Thr Asp Tyr Pro Asp Thr Val Lys Gly (SEQ ID NO:52), wherein CDR3 includes therein the sequence Gly Leu Ala Asp Gly Ala Trp (SEQ ID NO:53) as shown in FIG. 2 (SEQ ID NO:6), and wherein Xaa is alanine, arginine, serine, glycine, tyrosine or valine.

5. A nucleic acid molecule encoding a mutant polypeptide derived from BR96 (ATCC HB10036) comprising a heavy chain variable region including therein the sequence Gly Leu Xaa Asp Gly Ala Trp (SEQ ID NO:49) beginning at amino acid position 99 and ending with amino acid position 105, and wherein Xaa is alanine, arginine, serine, glycine, tyrosine or valine.

6. A nucleic acid molecule encoding a mutant polypeptide derived from BR96 (ATCC HO10036) comprising CDR1, CDR2, and CDR3, wherein CDR1 includes therein the sequence Gly Phe Thr Phe Ser Asp Tyr Tyr Met Tyr (SEQ ID NO:51), and wherein CDR3 includes therein the sequence Gly Leu Ala Asp Gly Ala Trp (SEQ ID NO:53) as shown in FIG. 2 (SEQ ID NO:6).

7. A nucleic acid molecule encoding a mutant polypeptide derived from BR96 (ATCC HB10036) comprising CDR1, CDR2, and CDR3, wherein CDR2 includes therein the sequence Tyr Ile Ser Gln Xaa Gly Asp Ile Thr Asp Tyr Pro Asp Thr Val Lys Gly (SEQ ID NO:52), wherein CDR3 includes therein the sequence Gly Leu Ala Asp Gly Ala Trp (SEQ ID NO:53) as shown in FIG. 2 (SEQ ID NO:6), and wherein Xaa is alanine, arginine, serine, glycine, tyrosine or valine.

8. A nucleic acid molecule encoding a mutant polypeptide derived from BR96 (ATCC HO10036) comprising an amino acid sequence including therein a CDR including a sequence Tyr Ile Ser Gln Asp Gly Asp Ile Thr Asp Tyr Pro Asp Thr Val Lys Gly (SEQ ID NO:54) beginning at amino acid position 50 and ending with amino acid position 66 as shown in FIG. 3 (SEQ ID NO:8).

9. A nucleic acid molecule encoding a mutant polypeptide derived from BR96 (ATCC HB10036) comprising a heavy chain variable region including therein the sequence Tyr Ile Ser Gln Asp Gly Asp Ile Thr Asp Tyr Pro Asp Thr Val Lys Gly (SEQ ID NO:54) beginning at amino acid position 50 and ending with amino acid position 66 as shown in FIG. 3 (SEQ ID NO:8), and wherein Xaa is alanine, arginine, serine, glycine, tyrosine or valine.

10. A nucleic acid molecule encoding a mutant polypeptide derived from BR96 (ATCC HB10036) comprising CDR1, CDR2, and CDR3, wherein CDR1 includes therein the sequence Gly Phe Thr Phe Ser Asp Tyr Tyr Met Tyr (SEQ ID NO:51), wherein CDR2 includes therein the sequence Tyr Ser Gln Asp Gly Asp Ile Thr Asp Tyr Pro Asp Thr Val Lys Gly (SEQ ID NO:54), and wherein CDR3 includes therein the sequence Gly Leu Asp Asp Gly Ala Trp (SEQ ID NO:55) as shown in FIG. 3 (SEQ ID NO:8).

11. A nucleic acid molecule encoding a mutant polypeptide derived from BR96 (ATCC HB10036) comprising CDR1, CDR2, and CDR3, wherein CDR2 includes therein the sequence Tyr Ile Ser Gln Asp Gly Asp Ile Thr Asp Tyr Pro Asp Thr Val Lys Gly (SEQ ID NO:54) and wherein CDR3 includes therein the sequence Gly Leu Asp Asp Gly Ala Trp (SEQ ID NO:55) as shown in FIG. 3 (SEQ ID NO:8).

12. A nucleic acid molecule of claim 3, 4, 5, 6, 7, 8, 9, 10 or 11 which is a cDNA molecule.

13. A plasmid which comprises the nucleic acid molecule of claim 3, 4, 5, 6, 7, 8, 9, 10 or 11 operably linked to at least one sequence providing for replication.

14. A plasmid which comprises the nucleic acid molecule of claim 3, 4, 5, 6, 7, 8, 9, 10 or 11 operably linked to at least one sequence providing for transcriptional control.

15. A host vector system comprising the plasmid of claim 13 in a suitable host cell.

16. A host vector system comprising the plasmid of claim 14 in a suitable host cell.

17. The host vector system of claim 15 or 16, wherein the suitable host cell is a bacterial cell.

18. The host vector system of claim 17, wherein the bacterial cell is a gram negative bacterium.

19. The host vector system of claim 18, wherein the gram negative bacterium is an *E. coli* bacterium.

20. The host vector system of claim 15 or 16, wherein the suitable host cell is a eukaryotic cell.

21. A method for producing a polypeptide comprising growing the host vector system of claim 15 or 16 so as to produce the polypeptide in the host and recovering the polypeptide so produced.

* * * * *

UNITED STATES PATENT AND TRADEMARK OFFICE
CERTIFICATE OF CORRECTION

PATENT NO. : 5,728,821

DATED : March 17, 1998

INVENTOR(S) : Yelton et al.

It is certified that error appears in the above-identified patent and that said Letters Patent is hereby corrected as shown below:

Under the heading FOREIGN PATENT DOCUMENTS, delete "of 0000" and insert –Kohler et al.–

Under OTHER PUBLICATIONS, Embleton et al., delete "(1984)" and insert –(1985)–

Column 2, line 54, delete "Morn" and insert –Horn–

Column 11, line 47, delete "Acid–Clearable" and insert –Acid–Cleavable–

Column 13, line 63, delete "arian" and insert –avian–

Column 15, line 46, insert –Vector– after "Immunoexpression"

Column 17, line 44, insert –BR96– before "Libraries"

Column 22, line 12, delete "arian" and insert –avian–

Column 22, line 61, delete "Art" and insert –An–

Column 34, Table, Column 104, delete "CCC" and insert –GCC–

Column 35, Table, line 1, delete "$V_H CDR3$" and insert –$V_H CDR1$–

UNITED STATES PATENT AND TRADEMARK OFFICE
CERTIFICATE OF CORRECTION

PATENT NO. : 5,728,821

DATED : March 17, 1998

INVENTOR(S) : Yelton et al.

It is certified that error appears in the above-identified patent and that said Letters Patent is hereby corrected as shown below:

Column 37, line 30, delete "Colon" and insert —colon—

Column 40, line 63, delete "290%" and insert —$\geq$90%—

Claim 1, column 73, line 41, delete "H010036" and insert —HB10036—

Claim 6, column 74, line 46, delete "H010036" and insert —HB10036—

Claim 10, column 75, line 14, insert —Ile— after "Tyr" (1st occurrence).

Signed and Sealed this

Sixth Day of April, 1999

Q. TODD DICKINSON

*Attest:*

*Attesting Officer*   Acting Commissioner of Patents and Trademarks

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: Variable heavy chain of BR96 antibody ( i x ) FEATURE:
        ( A ) NAME/KEY: CDS
        ( B ) LOCATION: 1..357

( x i ) SEQUENCE DESCRIPTION: SEQ ID NO:1:

```
GAA GTG AAT CTG GTG GAG TCT GGG GGA GGC TTA GTG CAG CCT GGA GGG          48
Glu Val Asn Leu Val Glu Ser Gly Gly Gly Leu Val Gln Pro Gly Gly
 1               5                  10                  15

TCC CTG AAA GTC TCC TGT GTA ACC TCT GGA TTC ACT TTC AGT GAC TAT          96
Ser Leu Lys Val Ser Cys Val Thr Ser Gly Phe Thr Phe Ser Asp Tyr
             20                  25                  30

TAC ATG TAT TGG GTT CGC CAG ACT CCA GAG AAG AGG CTG GAG TGG GTC         144
Tyr Met Tyr Trp Val Arg Gln Thr Pro Glu Lys Arg Leu Glu Trp Val
         35                  40                  45

GCA TAC ATT AGT CAA GGT GGT GAT ATA ACC GAC TAT CCA GAC ACT GTA         192
Ala Tyr Ile Ser Gln Gly Gly Asp Ile Thr Asp Tyr Pro Asp Thr Val
 50                  55                  60

AAG GGT CGA TTC ACC ATC TCC AGA GAC AAT GCC AAG AAC ACC CTG TAC         240
Lys Gly Arg Phe Thr Ile Ser Arg Asp Asn Ala Lys Asn Thr Leu Tyr
 65                  70                  75                  80

CTG CAA ATG AGC CGT CTG AAG TCT GAG GAC ACA GCC ATG TAT TAC TGT         288
Leu Gln Met Ser Arg Leu Lys Ser Glu Asp Thr Ala Met Tyr Tyr Cys
                 85                  90                  95

GCA AGA GGC CTG GAC GAC GGG GCC TGG TTT GCT TAC TGG GGC CAA GGG         336
Ala Arg Gly Leu Asp Asp Gly Ala Trp Phe Ala Tyr Trp Gly Gln Gly
```

```
                              100                         105                          110
ACT  CTG  GTC  ACG  GTC  TCT  GTA                                                                              357
Thr  Leu  Val  Thr  Val  Ser  Val
          115
```

( 2 ) INFORMATION FOR SEQ ID NO:2:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Glu  Val  Asn  Leu  Val  Glu  Ser  Gly  Gly  Gly  Leu  Val  Gln  Pro  Gly  Gly
 1                    5                        10                         15

Ser  Leu  Lys  Val  Ser  Cys  Val  Thr  Ser  Gly  Phe  Thr  Phe  Ser  Asp  Tyr
               20                       25                         30

Tyr  Met  Tyr  Trp  Val  Arg  Gln  Thr  Pro  Glu  Lys  Arg  Leu  Glu  Trp  Val
          35                       40                        45

Ala  Tyr  Ile  Ser  Gln  Gly  Gly  Asp  Ile  Thr  Asp  Tyr  Pro  Asp  Thr  Val
     50                       55                        60

Lys  Gly  Arg  Phe  Thr  Ile  Ser  Arg  Asp  Asn  Ala  Lys  Asn  Thr  Leu  Tyr
65                       70                        75                        80

Leu  Gln  Met  Ser  Arg  Leu  Lys  Ser  Glu  Asp  Thr  Ala  Met  Tyr  Tyr  Cys
                    85                       90                        95

Ala  Arg  Gly  Leu  Asp  Asp  Gly  Ala  Trp  Phe  Ala  Tyr  Trp  Gly  Gln  Gly
               100                      105                      110

Thr  Leu  Val  Thr  Val  Ser  Val
          115
```

( 2 ) INFORMATION FOR SEQ ID NO:3:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: Light chain of BR96

( i x ) FEATURE:
        ( A ) NAME/KEY: CDS
        ( B ) LOCATION: 1..342

( x i ) SEQUENCE DESCRIPTION: SEQ ID NO:3:

```
GAT  GTT  TTG  ATG  ACC  CAA  ATT  CCA  GTC  TCC  CTG  CCT  GTC  AGT  CTT  GGA     48
Asp  Val  Leu  Met  Thr  Gln  Ile  Pro  Val  Ser  Leu  Pro  Val  Ser  Leu  Gly
 1                    5                        10                         15

GAT  CAA  GCG  TCC  ATC  TCT  TGC  AGA  TCT  AGT  CAG  ATC  ATT  GTA  CAT  AAT     96
Asp  Gln  Ala  Ser  Ile  Ser  Cys  Arg  Ser  Ser  Gln  Ile  Ile  Val  His  Asn
               20                       25                         30

AAT  GGC  AAC  ACC  TAT  TTA  GAA  TGG  TAC  CTG  CAG  AAA  CCA  GGC  CAG  TCT    144
Asn  Gly  Asn  Thr  Tyr  Leu  Glu  Trp  Tyr  Leu  Gln  Lys  Pro  Gly  Gln  Ser
          35                       40                        45

CCA  CAG  CTC  CTG  ATC  TAC  AAA  GTT  TCC  AAC  CGA  TTT  TCT  GGG  GTC  CCA    192
Pro  Gln  Leu  Leu  Ile  Tyr  Lys  Val  Ser  Asn  Arg  Phe  Ser  Gly  Val  Pro
     50                       55                        60

GAC  AGG  TTC  AGC  GGC  ACT  GGA  TCA  GGG  ACA  GAT  TTC  ACA  CTC  AAG  ATC    240
Asp  Arg  Phe  Ser  Gly  Thr  Gly  Ser  Gly  Thr  Asp  Phe  Thr  Leu  Lys  Ile
```

|  |  |  |  |  |  |  |  |  |  |  |  |  |  |  |  |
|---|---|---|---|---|---|---|---|---|---|---|---|---|---|---|---|
| | | 65 | | | | 70 | | | | | 75 | | | | 80 |
| AGC | AGA | GTG | GAG | GCT | GAG | GAT | CTG | GGA | GTT | TAT | TAC | TGC | TTT | CAA | GGT | 288
| Ser | Arg | Val | Glu | Ala | Glu | Asp | Leu | Gly | Val | Tyr | Tyr | Cys | Phe | Gln | Gly |
| | | | | 85 | | | | 90 | | | | | 95 | | |
| TCA | CAT | GTT | CCA | TTC | ACG | TTC | GGC | TCG | GGG | ACA | AAG | TTG | GAA | ATA | AAA | 336
| Ser | His | Val | Pro | Phe | Thr | Phe | Gly | Ser | Gly | Thr | Lys | Leu | Glu | Ile | Lys |
| | | | 100 | | | | 105 | | | | 110 | | | | |
| CGG | GCT | | | | | | | | | | | | | | | 342
| Arg | Ala | | | | | | | | | | | | | | |

( 2 ) INFORMATION FOR SEQ ID NO:4:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Asp | Val | Leu | Met | Thr | Gln | Ile | Pro | Val | Ser | Leu | Pro | Val | Ser | Leu | Gly |
|---|---|---|---|---|---|---|---|---|---|---|---|---|---|---|---|
| 1 | | | | 5 | | | | | 10 | | | | | 15 | |
| Asp | Gln | Ala | Ser | Ile | Ser | Cys | Arg | Ser | Ser | Gln | Ile | Ile | Val | His | Asn |
| | | | | 20 | | | | | 25 | | | | | 30 | |
| Asn | Gly | Asn | Thr | Tyr | Leu | Glu | Trp | Tyr | Leu | Gln | Lys | Pro | Gly | Gln | Ser |
| | | | 35 | | | | | 40 | | | | | 45 | | |
| Pro | Gln | Leu | Leu | Ile | Tyr | Lys | Val | Ser | Asn | Arg | Phe | Ser | Gly | Val | Pro |
| | 50 | | | | | 55 | | | | | 60 | | | | |
| Asp | Arg | Phe | Ser | Gly | Thr | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Leu | Gly | Val | Tyr | Tyr | Cys | Phe | Gln | Gly |
| | | | | 85 | | | | | 90 | | | | | 95 | |
| Ser | His | Val | Pro | Phe | Thr | Phe | Gly | Ser | Gly | Thr | Lys | Leu | Glu | Ile | Lys |
| | | | 100 | | | | | 105 | | | | | 110 | | |
| Arg | Ala | | | | | | | | | | | | | | |

( 2 ) INFORMATION FOR SEQ ID NO:5:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Variable region of heavy chain of mutant BR96
        H3-36

( i x ) FEATURE:
        ( A ) NAME/KEY: CDS
        ( B ) LOCATION: 1..357

( x i ) SEQUENCE DESCRIPTION: SEQ ID NO:5:

| GAA | GTG | AAT | CTG | GTG | GAG | TCT | GGG | GGA | GGC | TTA | GTG | CAG | CCT | GGA | GGG | 48
|---|---|---|---|---|---|---|---|---|---|---|---|---|---|---|---|---|
| Glu | Val | Asn | Leu | Val | Glu | Ser | Gly | Gly | Gly | Leu | Val | Gln | Pro | Gly | Gly |
| 1 | | | | 5 | | | | | 10 | | | | | 15 | |
| TCC | CTG | AAA | GTC | TCC | TGT | GTA | ACC | TCT | GGA | TTC | ACT | TTC | AGT | GAC | TAT | 96
| Ser | Leu | Lys | Val | Ser | Cys | Val | Thr | Ser | Gly | Phe | Thr | Phe | Ser | Asp | Tyr |
| | | | 20 | | | | | 25 | | | | | 30 | | |
| TAC | ATG | TAT | TGG | GTT | CGC | CAG | ACT | CCA | GAG | AAG | AGG | CTG | GAG | TGG | GTC | 144
| Tyr | Met | Tyr | Trp | Val | Arg | Gln | Thr | Pro | Glu | Lys | Arg | Leu | Glu | Trp | Val |
| | 35 | | | | | 40 | | | | | 45 | | | | |

```
GCA TAC ATT AGT CAA GGT GGT GAT ATA ACC GAC TAT CCA GAC ACT GTA       192
Ala Tyr Ile Ser Gln Gly Gly Asp Ile Thr Asp Tyr Pro Asp Thr Val
    50                  55                  60

AAG GGT CGA TTC ACC ATC TCC AGA GAC AAT GCC AAG AAC ACC CTG TAC       240
Lys Gly Arg Phe Thr Ile Ser Arg Asp Asn Ala Lys Asn Thr Leu Tyr
65                  70                  75                  80

CTG CAA ATG AGC CGT CTG AAG TCT GAG GAC ACA GCC ATG TAT TAC TGT       288
Leu Gln Met Ser Arg Leu Lys Ser Glu Asp Thr Ala Met Tyr Tyr Cys
                85                  90                  95

GCA AGA GGC CTG GCG GAC GGG GCC TGG TTT GCT TAC TGG GGC CAA GGG       336
Ala Arg Gly Leu Ala Asp Gly Ala Trp Phe Ala Tyr Trp Gly Gln Gly
            100                 105                 110

ACT CTG GTC ACG GTC TCT GTA                                           357
Thr Leu Val Thr Val Ser Val
            115
```

( 2 ) INFORMATION FOR SEQ ID NO:6:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Glu Val Asn Leu Val Glu Ser Gly Gly Gly Leu Val Gln Pro Gly Gly
1               5                   10                  15

Ser Leu Lys Val Ser Cys Val Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Gln Gly Gly Asp Ile Thr Asp Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Leu Ala Asp Gly Ala Trp Phe Ala Tyr Trp Gly Gln Gly
            100                 105                 110

Thr Leu Val Thr Val Ser Val
            115
```

( 2 ) INFORMATION FOR SEQ ID NO:7:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Variable region of heavy chain of mutant BR96
        H2-60

( i x ) FEATURE:
        ( A ) NAME/KEY: CDS
        ( B ) LOCATION: 1..357

( x i ) SEQUENCE DESCRIPTION: SEQ ID NO:7:

```
GAA GTG AAT CTG GTG GAG TCT GGG GGA GGC TTA GTG CAG CCT GGA GGG       48
Glu Val Asn Leu Val Glu Ser Gly Gly Gly Leu Val Gln Pro Gly Gly
```

|   |   |   |   |   |   |   |   |   |   |   |   |   |   |   |   |     |
|---|---|---|---|---|---|---|---|---|---|---|---|---|---|---|---|-----|
| 1 |   |   |   | 5 |   |   |   |   |   | 10|   |   |   |   | 15|     |
| TCC | CTG | AAA | GTC | TCC | TGT | GTA | ACC | TCT | GGA | TTC | ACT | TTC | AGT | GAC | TAT | 96 |
| Ser | Leu | Lys | Val | Ser | Cys | Val | Thr | Ser | Gly | Phe | Thr | Phe | Ser | Asp | Tyr |    |
|     |     |     | 20  |     |     |     |     | 25  |     |     |     |     | 30  |     |     |    |
| TAC | ATG | TAT | TGG | GTT | CGC | CAG | ACT | CCA | GAG | AAG | AGG | CTG | GAG | TGG | GTC | 144 |
| Tyr | Met | Tyr | Trp | Val | Arg | Gln | Thr | Pro | Glu | Lys | Arg | Leu | Glu | Trp | Val |    |
|     |     | 35  |     |     |     |     | 40  |     |     |     |     | 45  |     |     |     |    |
| GCA | TAC | ATT | AGT | CAA | GAT | GGT | GAT | ATA | ACC | GAC | TAT | CCA | GAC | ACT | GTA | 192 |
| Ala | Tyr | Ile | Ser | Gln | Asp | Gly | Asp | Ile | Thr | Asp | Tyr | Pro | Asp | Thr | Val |    |
|     | 50  |     |     |     |     | 55  |     |     |     |     | 60  |     |     |     |     |    |
| AAG | GGT | CGA | TTC | ACC | ATC | TCC | AGA | GAC | AAT | GCC | AAG | AAC | ACC | CTG | TAC | 240 |
| Lys | Gly | Arg | Phe | Thr | Ile | Ser | Arg | Asp | Asn | Ala | Lys | Asn | Thr | Leu | Tyr |    |
| 65  |     |     |     |     | 70  |     |     |     |     | 75  |     |     |     |     | 80  |    |
| CTG | CAA | ATG | AGC | CGT | CTG | AAG | TCT | GAG | GAC | ACA | GCC | ATG | TAT | TAC | TGT | 288 |
| Leu | Gln | Met | Ser | Arg | Leu | Lys | Ser | Glu | Asp | Thr | Ala | Met | Tyr | Tyr | Cys |    |
|     |     |     |     | 85  |     |     |     |     | 90  |     |     |     |     | 95  |     |    |
| GCA | AGA | GGC | CTG | GAC | GAC | GGG | GCC | TGG | TTT | GCT | TAC | TGG | GGC | CAA | GGG | 336 |
| Ala | Arg | Gly | Leu | Asp | Asp | Gly | Ala | Trp | Phe | Ala | Tyr | Trp | Gly | Gln | Gly |    |
|     |     |     | 100 |     |     |     |     | 105 |     |     |     |     | 110 |     |     |    |
| ACT | CTG | GTC | ACG | GTC | TCT | GTA |     |     |     |     |     |     |     |     |     | 357 |
| Thr | Leu | Val | Thr | Val | Ser | Val |     |     |     |     |     |     |     |     |     |    |
|     |     | 115 |     |     |     |     |     |     |     |     |     |     |     |     |     |    |

( 2 ) INFORMATION FOR SEQ ID NO:8:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Glu Val Asn Leu Val Glu Ser Gly Gly Gly Leu Val Gln Pro Gly Gly
 1               5                  10                  15

Ser Leu Lys Val Ser Cys Val Thr Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Tyr Ile Ser Gln Asp Gly Asp Ile Thr Asp Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Leu Asp Asp Gly Ala Trp Phe Ala Tyr Trp Gly Gln Gly
                100                 105                 110

Thr Leu Val Thr Val Ser Val
            115
```

( 2 ) INFORMATION FOR SEQ ID NO:9:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Variable region of heavy chain of mutant BR96
        H1-4-3

( i x ) FEATURE:
    ( A ) NAME/KEY: CDS
    ( B ) LOCATION: 1..357

( x i ) SEQUENCE DESCRIPTION: SEQ ID NO:9:

```
GAA GTG AAT CTG GTG GAG TCT GGG GGA GGC TTA GTG CAG CCT GGA GGG       48
Glu Val Asn Leu Val Glu Ser Gly Gly Gly Leu Val Gln Pro Gly Gly
 1               5                  10                  15

TCC CTG AAA GTC TCC TGT GTA ACC TCT GGA TTC CCG TTC GCG TCG TAT       96
Ser Leu Lys Val Ser Cys Val Thr Ser Gly Phe Pro Phe Ala Ser Tyr
            20                  25                  30

TAC ATG TAT TGG GTT CGC CAG ACT CCA GAG AAG AGG CTG GAG TGG GTC      144
Tyr Met Tyr Trp Val Arg Gln Thr Pro Glu Lys Arg Leu Glu Trp Val
        35                  40                  45

GCA TAC ATT AGT CAA GGT GGT GAT ATA ACC GAC TAT CCA GAC ACT GTA      192
Ala Tyr Ile Ser Gln Gly Gly Asp Ile Thr Asp Tyr Pro Asp Thr Val
    50                  55                  60

AAG GGT CGA TTC ACC ATC TCC AGA GAC AAT GCC AAG AAC ACC CTG TAC      240
Lys Gly Arg Phe Thr Ile Ser Arg Asp Asn Ala Lys Asn Thr Leu Tyr
 65                 70                  75                  80

CTG CAA ATG AGC CGT CTG AAG TCT GAG GAC ACA GCC ATG TAT TAC TGT      288
Leu Gln Met Ser Arg Leu Lys Ser Glu Asp Thr Ala Met Tyr Tyr Cys
            85                  90                  95

GCA AGA GGC CTG GCG GAC GGG GCC TGG TTT GCT TAC TGG GGC CAA GGG      336
Ala Arg Gly Leu Ala Asp Gly Ala Trp Phe Ala Tyr Trp Gly Gln Gly
        100                 105                 110

ACT CTG GTC ACG GTC TCT GTA                                          357
Thr Leu Val Thr Val Ser Val
    115
```

( 2 ) INFORMATION FOR SEQ ID NO:10:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Glu Val Asn Leu Val Glu Ser Gly Gly Gly Leu Val Gln Pro Gly Gly
 1               5                  10                  15

Ser Leu Lys Val Ser Cys Val Thr Ser Gly Phe Pro Phe Ala Ser Tyr
            20                  25                  30

Tyr Met Tyr Trp Val Arg Gln Thr Pro Glu Lys Arg Leu Glu Trp Val
        35                  40                  45

Ala Tyr Ile Ser Gln Gly Gly Asp Ile Thr Asp Tyr Pro Asp Thr Val
    50                  55                  60

Lys Gly Arg Phe Thr Ile Ser Arg Asp Asn Ala Lys Asn Thr Leu Tyr
 65                 70                  75                  80

Leu Gln Met Ser Arg Leu Lys Ser Glu Asp Thr Ala Met Tyr Tyr Cys
            85                  90                  95

Ala Arg Gly Leu Ala Asp Gly Ala Trp Phe Ala Tyr Trp Gly Gln Gly
        100                 105                 110

Thr Leu Val Thr Val Ser Val
    115
```

( 2 ) INFORMATION FOR SEQ ID NO:11:

( i ) SEQUENCE CHARACTERISTICS:
        ( A ) LENGTH: 357 base pairs ( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Variable region of heavy chain of mutant BR96
H2+H3

( i x ) FEATURE:
( A ) NAME/KEY: CDS
( B ) LOCATION: 1..357

( x i ) SEQUENCE DESCRIPTION: SEQ ID NO:11:

| GAA | GTG | AAT | CTG | GTG | GAG | TCT | GGG | GGA | GGC | TTA | GTG | CAG | CCT | GGA | GGG | 48 |
| Glu | Val | Asn | Leu | Val | Glu | Ser | Gly | Gly | Gly | Leu | Val | Gln | Pro | Gly | Gly | |
| 1 | | | | 5 | | | | | 10 | | | | | 15 | | |

| TCC | CTG | AAA | GTC | TCC | TGT | GTA | ACC | TCT | GGA | TTC | ACT | TTC | AGT | GAC | TAT | 96 |
| Ser | Leu | Lys | Val | Ser | Cys | Val | Thr | Ser | Gly | Phe | Thr | Phe | Ser | Asp | Tyr | |
| | | | 20 | | | | | 25 | | | | | 30 | | | |

| TAC | ATG | TAT | TGG | GTT | CGC | CAG | ACT | CCA | GAG | AAG | AGG | CTG | GAG | TGG | GTC | 144 |
| Tyr | Met | Tyr | Trp | Val | Arg | Gln | Thr | Pro | Glu | Lys | Arg | Leu | Glu | Trp | Val | |
| | | 35 | | | | | 40 | | | | | 45 | | | | |

| GCA | TAC | ATT | AGT | CAA | GAT | GGT | GAT | ATA | ACC | GAC | TAT | CCA | GAC | ACT | GTA | 192 |
| Ala | Tyr | Ile | Ser | Gln | Asp | Gly | Asp | Ile | Thr | Asp | Tyr | Pro | Asp | Thr | Val | |
| | 50 | | | | | 55 | | | | | 60 | | | | | |

| AAG | GGT | CGA | TTC | ACC | ATC | TCC | AGA | GAC | AAT | GCC | AAG | AAC | ACC | CTG | TAC | 240 |
| Lys | Gly | Arg | Phe | Thr | Ile | Ser | Arg | Asp | Asn | Ala | Lys | Asn | Thr | Leu | Tyr | |
| 65 | | | | | 70 | | | | | 75 | | | | | 80 | |

| CTG | CAA | ATG | AGC | CGT | CTG | AAG | TCT | GAG | GAC | ACA | GCC | ATG | TAT | TAC | TGT | 288 |
| Leu | Gln | Met | Ser | Arg | Leu | Lys | Ser | Glu | Asp | Thr | Ala | Met | Tyr | Tyr | Cys | |
| | | | | 85 | | | | | 90 | | | | | 95 | | |

| GCA | AGA | GGC | CTG | GCG | GAC | GGG | GCC | TGG | TTT | GCT | TAC | TGG | GGC | CAA | GGG | 336 |
| Ala | Arg | Gly | Leu | Ala | Asp | Gly | Ala | Trp | Phe | Ala | Tyr | Trp | Gly | Gln | Gly | |
| | | | 100 | | | | | 105 | | | | | 110 | | | |

| ACT | CTG | GTC | ACG | GTC | TCT | GTA | | | | | | | | | | 357 |
| Thr | Leu | Val | Thr | Val | Ser | Val | | | | | | | | | | |
| | | 115 | | | | | | | | | | | | | | |

( 2 ) INFORMATION FOR SEQ ID NO:12:

( i ) SEQUENCE CHARACTERISTICS:
( A ) LENGTH: 119 amino acids
( B ) TYPE: amino acid
( D ) TOPOLOGY: linear ( i i ) MOLECULE TYPE: protein ( x i ) SEQUENCE DESCRIPTION: SEQ ID NO:12:

| Glu | Val | Asn | Leu | Val | Glu | Ser | Gly | Gly | Gly | Leu | Val | Gln | Pro | Gly | Gly |
| 1 | | | | 5 | | | | | 10 | | | | | 15 | |

| Ser | Leu | Lys | Val | Ser | Cys | Val | Thr | Ser | Gly | Phe | Thr | Phe | Ser | Asp | Tyr |
| | | | 20 | | | | | 25 | | | | | 30 | | |

| Tyr | Met | Tyr | Trp | Val | Arg | Gln | Thr | Pro | Glu | Lys | Arg | Leu | Glu | Trp | Val |
| | | 35 | | | | | 40 | | | | | 45 | | | |

| Ala | Tyr | Ile | Ser | Gln | Asp | Gly | Asp | Ile | Thr | Asp | Tyr | Pro | Asp | Thr | Val |
| | 50 | | | | | 55 | | | | | 60 | | | | |

| Lys | Gly | Arg | Phe | Thr | Ile | Ser | Arg | Asp | Asn | Ala | Lys | Asn | Thr | Leu | Tyr |
| 65 | | | | | 70 | | | | | 75 | | | | | 80 |

| Leu | Gln | Met | Ser | Arg | Leu | Lys | Ser | Glu | Asp | Thr | Ala | Met | Tyr | Tyr | Cys |
| | | | | 85 | | | | | 90 | | | | | 95 | |

| Ala | Arg | Gly | Leu | Ala | Asp | Gly | Ala | Trp | Phe | Ala | Tyr | Trp | Gly | Gln | Gly |
| | | | 100 | | | | | 105 | | | | | 110 | | |

Thr Leu Val Thr Val Ser Val
            115

( 2 ) INFORMATION FOR SEQ ID NO:13:

( i ) SEQUENCE CHARACTERISTICS:
            ( A ) LENGTH: 10 amino acids
            ( B ) TYPE: amino acid
            ( D ) TOPOLOGY: linear ( i i ) MOLECULE TYPE: peptide ( x i ) SEQUENCE DESCRIPTION: SEQ ID NO:13:

Tyr Pro Tyr Asp Val Pro Asp Tyr Ala Ser
    1               5                   10

( 2 ) INFORMATION FOR SEQ ID NO:14:

( i ) SEQUENCE CHARACTERISTICS:
            ( A ) LENGTH: 33 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:14:

AGGGACTCCA GAAAGCTTTT AGGCATAAAT CCA                            33

( 2 ) INFORMATION FOR SEQ ID NO:15:

( i ) SEQUENCE CHARACTERISTICS:
            ( A ) LENGTH: 33 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:15:

GAAGTCATCA GCACGCGTTT AAGTGTAGGT GTT                            33

( 2 ) INFORMATION FOR SEQ ID NO:16:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:16:

GCCCAACCAG CCATGGCCGA TGTTTTGATG ACCCAAAT                       38

( 2 ) INFORMATION FOR SEQ ID NO:17:

( i ) SEQUENCE CHARACTERISTICS:
            ( A ) LENGTH: 54 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:17:

AGATGGCGGG AAGATGAAGA CAGATGGTGC AGCCACAGTC CGTTTTATTT CCAA     54

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GACAGATGGT GCAGCCACAG TCCG                        24

( 2 ) INFORMATION FOR SEQ ID NO:19:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CCTGTGGCAA AAGCCGAAGT GAATCTGGTG GAG            33

( 2 ) INFORMATION FOR SEQ ID NO:20:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

ATGGGCCCTT GGTGGAGGCT ACAGAGACCG TGACCAG      37

( 2 ) INFORMATION FOR SEQ ID NO:21:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

ACCTTGACTA ATGTATGCGA CC                          22

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GTACCATTCT AAAAGCTTTT AAATGATCTG ACT            33

( 2 ) INFORMATION FOR SEQ ID NO:23:

( i ) SEQUENCE CHARACTERISTICS:
        ( A ) LENGTH: 33 base pairs
        ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

AGAAAATCGG TTAAGCTTTT AGATCAGGAG CTG 33

( 2 ) INFORMATION FOR SEQ ID NO:24:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CGAGCCGAAC GTAAGCTTTT ATTGAAAGCA GTA 33

( 2 ) INFORMATION FOR SEQ ID NO:25:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

AACCCAATAC ATACGCGTTT AAGAGGTTAC ACA 33

( 2 ) INFORMATION FOR SEQ ID NO:26:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

AGTGTCTGGA TAACGCGTTT AAATGTATGC GAC 33

( 2 ) INFORMATION FOR SEQ ID NO:27:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CCAGTAAGCA AAACGCGTTT ATCTTGCACA GTA 33

( 2 ) INFORMATION FOR SEQ ID NO:28:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GTACCATTCT AAATAGGTGT TGCCATTATT ATGTACAATG ATCTGACT       48

( 2 ) INFORMATION FOR SEQ ID NO:29:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GTACCATTCT AAMNNMNNMN NMNNMNNMNN MNNMNNAATG ATCTGACT       48

( 2 ) INFORMATION FOR SEQ ID NO:30:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

AGAAAATCGG TTGGAAACTT TGTAGATCAG GAGCTG       36

( 2 ) INFORMATION FOR SEQ ID NO:31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

AGAAAATCGG TTGATCAGGA GCTG       24

( 2 ) INFORMATION FOR SEQ ID NO:32:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CGAGCCGAAC GTGAATGGAA CATGTGAACC TTGAAAGCAG TA       42

( 2 ) INFORMATION FOR SEQ ID NO:33:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CGAGCCGAAC GTMNNMNNMN NMNNMNNMNN TTGAAAGCAG TA       42

( 2 ) INFORMATION FOR SEQ ID NO:34:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:34:

AACCCAATAC ATGTAATAGT CACTGAAAGT GAATCCAGAG GTTACACA   48

( 2 ) INFORMATION FOR SEQ ID NO:35:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:35:

AACCCAATAC ATMNNMNNMN NMNNMNNMNN MNNMNNAGAG GTTACACA   48

( 2 ) INFORMATION FOR SEQ ID NO:36:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:36:

AGTGTCTGGA TAGTCGGTTA TATCACCACC TTGACTAATG TATGCGAC   48

( 2 ) INFORMATION FOR SEQ ID NO:37:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:37:

AGTGTCTGGA TAMNNMNNMN NMNNMNNMNN MNNMNNAATG TATGCGAC   48

( 2 ) INFORMATION FOR SEQ ID NO:38:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:38:

CCAGTAAGCA AACCAGGCCC CGTCGTCCAG GCCTCTTGCA CAGTA   45

( 2 ) INFORMATION FOR SEQ ID NO:39:

( i ) SEQUENCE CHARACTERISTICS:
    ( A ) LENGTH: 45 base pairs
    ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

CCAGTAAGCA AAMNNMNNMN NMNNMNNMNN MNNTCTTGCA CAGTA    45

( 2 ) INFORMATION FOR SEQ ID NO:40:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

CCAGGCCCCG TCCGCCAGGC CTCTTGC    27

( 2 ) INFORMATION FOR SEQ ID NO:41:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

GCTAGACATA TGGAAGTGAA TCTGCTGGAG TCTGGGGGA    39

( 2 ) INFORMATION FOR SEQ ID NO:42:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

GCTAGAGGAT CCTACAGAGA CCGTGACCAG AGTCCCTTG    39

( 2 ) INFORMATION FOR SEQ ID NO:43:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

TACACAAAGC TTGATGTTTT GATGACCCAA ATTCCAGTC    39

( 2 ) INFORMATION FOR SEQ ID NO:44:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

GATCCGGAGG TGGAGGTTCT GGTGGAGGTG GATCTGGAGG TGGAGGTTCT A    51

( 2 ) INFORMATION FOR SEQ ID NO:45:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

AGCTTAGAAC CTCCACCTCC AGATCCACCT CCACCAGAAC CTCCACCTCC G    51

( 2 ) INFORMATION FOR SEQ ID NO:46:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CAGATTCACT TCGGCCATGG CCACAGGG    28

( 2 ) INFORMATION FOR SEQ ID NO:47:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

GGGACTCTGG TCACGGTCTC TTCAGGATCC GGA    33

( 2 ) INFORMATION FOR SEQ ID NO:48:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

TGGGTAGGAT CCACTAGTGC GTTTGATCTC CAGCTTGG    38

( 2 ) INFORMATION FOR SEQ ID NO:49:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

Gly Leu Xaa Asp Gly Ala Trp
    1               5

( 2 ) INFORMATION FOR SEQ ID NO:50:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:50:

Gly Phe Pro Phe Ala Ser Tyr Tyr
1               5

( 2 ) INFORMATION FOR SEQ ID NO:51:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:51:

Gly Phe Thr Phe Ser Asp Tyr Tyr Met Tyr
1               5                   10

( 2 ) INFORMATION FOR SEQ ID NO:52:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:52:

Tyr Ile Ser Gln Xaa Gly Asp Ile Thr Asp Tyr Pro Asp Thr Val Lys
1               5                   10                      15

Gly ( 2 ) INFORMATION FOR SEQ ID NO:53:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:53:

Gly Leu Ala Asp Gly Ala Trp
1               5

( 2 ) INFORMATION FOR SEQ ID NO:54:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:54:

Tyr Ile Ser Gln Asp Gly Asp Ile Thr Asp Tyr Pro Asp Thr Val Lys
1               5                   10                      15

Gly ( 2 ) INFORMATION FOR SEQ ID NO:55:

(i) SEQUENCE CHARACTERISTICS:
  (A) LENGTH: 7 amino acids
  (B) TYPE: amino acid
  (D) TOPOLOGY: linear (ii) MOLECULE TYPE: peptide (xi) SEQUENCE DESCRIPTION: SEQ ID NO:55:

Gly Leu Asp Asp Gly Ala Trp
1               5

(2) INFORMATION FOR SEQ ID NO:56:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:56:

GGCCTGGCGG ACGGGCCTG G                           21

(2) INFORMATION FOR SEQ ID NO:57:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:57:

GGATTCCCGT TCGCGTCGTA T                          21